United States Patent
Adelstein et al.

(10) Patent No.: US 11,814,664 B2
(45) Date of Patent: Nov. 14, 2023

(54) MICROORGANISMS AND METHODS FOR PRODUCING (3R)-HYDROXYBUTYL (3R)-HYDROXYBUTYRATE

(71) Applicant: Genomatica, Inc., San Diego, CA (US)

(72) Inventors: Benjamin Adelstein, San Diego, CA (US); Robin E. Osterhout, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 59 days.

(21) Appl. No.: 14/893,510

(22) PCT Filed: May 23, 2014

(86) PCT No.: PCT/US2014/039322
§ 371 (c)(1),
(2) Date: Nov. 23, 2015

(87) PCT Pub. No.: WO2014/190251
PCT Pub. Date: Nov. 27, 2014

(65) Prior Publication Data
US 2016/0108442 A1 Apr. 21, 2016

Related U.S. Application Data

(60) Provisional application No. 61/887,219, filed on Oct. 4, 2013, provisional application No. 61/827,492, filed on May 24, 2013.

(51) Int. Cl.
| | | |
|---|---|---|
| *C12P 7/62* | (2022.01) | |
| *C12N 9/18* | (2006.01) | |
| *A61K 31/22* | (2006.01) | |
| *A61K 35/66* | (2015.01) | |
| *A61K 36/064* | (2006.01) | |
| *A23L 33/135* | (2016.01) | |

(Continued)

(52) U.S. Cl.
CPC .............. *C12P 7/62* (2013.01); *A23L 33/135* (2016.08); *A61K 31/22* (2013.01); *A61K 35/66* (2013.01); *A61K 36/064* (2013.01); *C07C 69/675* (2013.01); *C12N 1/00* (2013.01); *C12N 1/145* (2021.05); *C12N 1/205* (2021.05); *C12N 9/18* (2013.01); *C12N 15/52* (2013.01); *C12Y 101/011* (2013.01); *C12Y 101/01035* (2013.01); *C12Y 301/01067* (2013.01); *C12Y 301/08001* (2013.01); *A23V 2002/00* (2013.01); *C07B 2200/05* (2013.01); *C12R 2001/00* (2021.05); *C12R 2001/01* (2021.05); *C12R 2001/645* (2021.05); *Y02P 20/10* (2015.11)

(58) Field of Classification Search
CPC .... C12N 15/52; C12N 9/0006; C12N 9/0008; C12N 9/1029; C12N 9/1096; C12N 9/88; C12N 15/70; C12N 15/81; C12N 9/001; C12N 9/12; C12N 9/13; C12N 9/16; C12N 9/18; C12N 9/90; C12N 9/93; C07D 207/273; C07D 405/06; C07D 405/12; C07D 409/06; C07D 409/12; C07D 413/06; C07D 413/12; C07D 417/06; C07D 417/12; C12P 7/18; C12P 7/62; C12Y 101/01157; C12Y 101/01; C12Y 101/01035; C12Y 101/011; C12Y 102/01; C12Y 203/01; C12Y 206/01; C12Y 301/01067; C12Y 301/08001; C12Y 401/01; C12Y 402/01; C12Y 402/01055; C12Y 403/01; A23L 33/135; A23V 2002/00; A61K 31/22; A61K 35/66; A61K 36/064; B01D 3/002; C07B 2200/05; C07C 29/80; C07C 69/675; C12R 1/00; C12R 1/01; C12R 1/645; Y02P 20/127
See application file for complete search history.

(56) References Cited

U.S. PATENT DOCUMENTS

| | | |
|---|---|---|
| 5,958,745 A | 9/1999 | Gruys et al. |
| 7,127,379 B2 | 10/2006 | Palsson et al. |

(Continued)

FOREIGN PATENT DOCUMENTS

| | | |
|---|---|---|
| EP | 1605048 | 12/2005 |
| WO | WO 2002/055995 A2 | 7/2002 |

(Continued)

OTHER PUBLICATIONS

Budin et al. (2018) Bioorganic Chemistry 80: 560-564 (Year: 2018).*

(Continued)

*Primary Examiner* — Blaine Lankford
(74) *Attorney, Agent, or Firm* — Greenberg Traurig, LLP

(57) ABSTRACT

Provided herein are non-naturally occurring microbial organisms having a pathway for production of (3R)-hydroxybutyl (3R)-hydroxybutyrate, wherein the organism can further include a (R)-1,3-butanediol pathway, a (3R)-hydroxybutyrate pathway, a (3R)-hydroxybutyryl-CoA pathway, an acetoacetate pathway, an acetoacetyl-CoA pathway, a (3R)-hydroxybutyl-ACP pathway, or an acetoacetyl-ACP pathway. Additionally provided are methods and processes for producing and isolating (3R)-hydroxybutyl (3R)-hydroxybutyrate using the microbial organisms, and various compositions having the (3R)-hydroxybutyl (3R)-hydroxybutyrate. Still further provided are methods of treating or preventing a disease, disorder or condition using the (3R)-hydroxybutyl (3R)-hydroxybutyrate produced by the microbial organisms of the invention.

6 Claims, 4 Drawing Sheets

(51) Int. Cl.
| | |
|---|---|
| C12N 1/00 | (2006.01) |
| C12N 1/14 | (2006.01) |
| C12N 1/20 | (2006.01) |
| C07C 69/675 | (2006.01) |
| C12N 15/52 | (2006.01) |
| C12R 1/00 | (2006.01) |
| C12R 1/01 | (2006.01) |
| C12R 1/645 | (2006.01) |

(56) References Cited

U.S. PATENT DOCUMENTS

| | | | |
|---|---|---|---|
| 7,901,915 | B2 | 3/2011 | Symes et al. |
| 8,048,661 | B2 | 11/2011 | Burgard et al. |
| 8,420,597 | B2 | 4/2013 | Cho et al. |
| 2002/0012939 | A1 | 1/2002 | Palsson |
| 2002/0168654 | A1 | 11/2002 | Maranas et al. |
| 2003/0059792 | A1 | 3/2003 | Palsson et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2005/0221466 | A1 | 10/2005 | Liao et al. |
| 2009/0047719 | A1 | 2/2009 | Burgard et al. |
| 2010/0203614 | A1 | 8/2010 | Wahlen et al. |
| 2010/0330635 | A1 | 12/2010 | Burgard et al. |
| 2011/0003355 | A1 | 1/2011 | Clark et al. |
| 2011/0207203 | A1 | 8/2011 | Reppas et al. |
| 2011/0237666 | A1 | 9/2011 | Clarke et al. |
| 2012/0064611 | A1* | 3/2012 | Robertson .................. C12P 7/62 435/280 |
| 2012/0276606 | A1 | 11/2012 | Okabayashi et al. |
| 2012/0329113 | A1 | 12/2012 | Burgard et al. |
| 2018/0195096 | A1* | 7/2018 | Veech .................... C07C 51/09 |

FOREIGN PATENT DOCUMENTS

| | | |
|---|---|---|
| WO | WO 2003/046159 A1 | 6/2003 |
| WO | WO 2003/091423 A1 | 11/2003 |
| WO | WO 2003/106998 A1 | 12/2003 |
| WO | WO 2007/141208 A2 | 12/2007 |
| WO | WO 2012/177619 A2 | 12/2012 |
| WO | WO 2013/048557 A1 | 4/2013 |

OTHER PUBLICATIONS

Aberhart and Hsu, "Stereospecific hydrogen loss in the conversion of [2H7] isobutyrate to β-hydroxyisobutyrate in Pseudomonas putida. The stereochemistry of β-hydroxyisobutyrate dehydrogenase," *J. Chem. Soc. [Perkin1]*, 6:1404-1406 (1979).
Aharoni et al., "Directed evolution of mammalian paraoxonases PON1 and PON3 for bacterial expression and catalytic specialization," *Proc. Natl. Acad. Sci. USA*, 101(2):482-487 (2004).
Alber et al., "Malonyl-Coenzyme A reductase in the modified 3-hydroxypropionate cycle for autotrophic carbon fixation in archaeal Metallosphaera and Sulfolobus spp.," *J. Bacteriol.*, 188(24):8551-8559 (2006).
Alber et al., "Study of an alternate glyoxylate cycle for acetate assimilation by Rhodobacter sphaeroides," *Mol. Microbiol.*, 61(2):297-309 (2006).
Aragon and Lowenstein, "A survey of enzymes which generate or use acetoacetyl thioesters in rat liver," *J. Biol. Chem.*, 258(8):4725-4733 (1983).
Barker et al., "Butyryl-CoA: acetoacetate CoA-transferase from a lysine-fermenting clostridium," *J. Biol. Chem.*, 253(4):1219-25 (1978).
Barker et al., "Pathway of lysine degradation in fusobacterium nucleatum," *J. Bacteriol.*, 152(1):201-7 (1982).
Berg et al., "A 3-Hydroxypropionate/4-Hydroxybutyrate Autotrophic Carbon Dioxide Assimilation Pathway in Archaea," *Science*, 318(5857) 1782-1786 (2007).

Bergquist and Gibbs, "Degenerate oligonucleotide gene shuffling," *Meth. Mol. Biol.*, 352:191- 204 (2007).
Bergquist et al., "Degenerate oligonucleotide gene shuffling (DOGS) and random drift mutagenesis (RNDM): Two complementary techniques for enzyme evolution," *Biomol. Eng.*, 22:63-72 (2005).
Billecke et al., "Human serum paraoxonase (PON1) isozymes Q and R hydrolyze lactones and cyclic carbonate esters," *Drug Metab. Dispos.*, 28(11):1335-1342 (2000).
Binstock and Schulz, "Fatty acid oxidation complex from *Escherichia coli*," *Methods Enzymol.*, 71(Pt C):403-411 (1981).
Bonner and Bloch, "Purification and properties of fatty acyl thioesterase I from *Escherichia coli*," *J. Biol. Chem.*, 247(10):3123-3133 (1972).
BrÄsen and Schönheit, "Unusual ADP-forming acetyl-Coenzyme A synthetases from the mesophilic halophilic euryarchaeon Haloarcula marismortui and from the hyperthermophilic crenarchaeon Pyrobaculum aerophilum," *Arch. Microbiol.*, 182(4):277-287 (2004).
Bravo et al., "Reliable, sensitive, rapid and quantitative enzyme-based assay for gamma- hydroxybutyric acid (GHB)," *J. Forensic Sci.*, 49:379-387 (2004).
Breitkreuz et al., "A novel γ-hydroxybutyrate dehydrogenase: Identification and expression of an *Arabidopsis* cDNA and potential role under oxygen deficiency," *J. Biol. Chem.*, 278:41552-41556 (2003).
Burgard et al., "Minimal Reaction Sets for *Escherichia coli* Metabolism under Different Growth Requirements and Uptake Environments," *Biotechnol. Prog.*, 17:791-797 (2001).
Burgard et al., "Optknock: a bilevel programming framework for identifying gene knockout strategies for microbial strain optimization," *Biotechnol. Bioeng.*, 84(6):647-657 (2003).
Buu et al., "Functional characterization and localization of acetyl-CoA hydrolase, Ach1p, in *Saccharomyces cerevisiae*," *J. Biol. Chem.*, 278:17203-17209 (2003).
Cabre et al., "Purification and properties of bovine liver aldehyde oxidase; comparison with xanthine oxidase," *Biochem. Soc. Trans.*, 15:882-883 (1987).
Choi et al, "β-ketoacyl-acyl carrier protein synthase III (FabH) is a determining factor in branched- chain fatty acid biosynthesis," *J. Bacteriol.*, 182:365-370 (2000).
Chowdhury et al., "Cloning and Overexpression of the 3-Hydroxyisobutyrate Dehydrogenase Gene from Pseudomonas putida E23," *Biosci. Biotechnol. Biochem.*, 67:438-441 (2003).
Chowdhury et al., "3-Hydroxyisobutyrate dehydrogenase from Pseudomonas putida E23: purification and characterization," *Biosci. Biotechnol. Biochem.*, 60(12):2043-2047 (1996).
Coco et al., "DNA shuffling method for generating highly recombined genes and evolved enzymes," *Nat. Biotechnol.*, 19:354-359 (2001).
Colby and Chen, "Purification and properties of 3-hydroxybutyryl-Coenzyme A dehydrogenase from Clostridium beijerinckii ("Clostridium butylicum") NRRL B593," *Appl. Environ. Microbiol.*, 58:3297-3302 (1992).
Colonna et al., "Synthesis and radiocarbon evidence of terephthalate polyesters completely prepared from renewable resources," *Green Chemistry*, 13:2543-2548 (2011).
Corthesy-Theulaz et al., "Cloning and characterization of helicobacter pylori succinyl CoA:acetoacetate CoA-transferase, a novel prokaryotic member of the CoA-transferase family," *J. Biol. Chem.*, 272(41):25659-25667 (1997).
Currie et al., "Authentication and dating of biomass components of industrial materials; links to sustainable technology," *Nuclear Instruments and Methods in Physics Research B*, 172:281-287 (2000).
Dartois et al., "Cloning, nucleotide sequence expression in *Escherichia coli* of a lipase gene from *Bacillus subtilis* 168," *Biochim. Biophys. Acta*, 1131:253-260 (1992).
Davis et al., "Overproduction of acetyl-CoA carboxylase activity increases the rate of fatty acid biosynthesis in *Escherichia coli*," *J. Biol. Chem.*, 275:28593-28598 (2000).
Deana, "Substrate specificity of a dicarboxyl-CoA: dicarboxylic acid Coenzyme A transferase from rat liver mitochondria," *Biochem. Int.*, 26(4):767-773 (1992).
Dehesh et al, "Two novel thioesterases are key determinants of the bimodal distribution of Acyl chain length of cuphea palustris seed oil," *Plant Physiol.*, 110:203-210 (1996).

(56) References Cited

OTHER PUBLICATIONS

Draganov et al., "Human paraoxonases (PON1, PON2, and PON3) are lactonases with overlapping and distinct substrate specificities," *J. Lipid Res.*, 46:1239-1247 (2005).
Drake, "Acetogenesis, acetogenic bacteria, and the acetyl-CoA "Wood/Ljungdahl" pathway: past and current perspectives," in *Acetogenesis*, DrakeH., ed., Chapman & Hall, New York, NY, pp. 3-60 (1994).
Du et al, "Lactococcus lactis fabH, encoding beta-ketoacyl-acyl carrier protein synthase, can be functionally replaced by the Plasmodium falciparum congener," *Appl. Microbiol. Biotechnol.*, 76(12):3959-3966 (2010).
Efe et al., "Options for biochemical production of 4-hydroxybutyrate and its lactone as a substitute for petrochemical production," *Biotechnol. Bioeng.*, 99(6):1392-1406 (2008).
Fernandes and Kolattukudy, "Cloning, sequencing and characterization of a fatty acid synthase-encoding gene from *Mycobacterium tuberculosis* var. bovis BCG," *Gene*, 170:95-99 (1996).
Fishbein and Bessman, "Purification and properties of an enzyme in human blood and rat liver microsomes catalyzing the formation and hydrolysis of γ-lactones. I. Tissue localization, stoichiometry, specificity, distinction from esterase," *J. Biol. Chem.*, 241(21):4835-4841 (1966).
Fishbein and Bessman, "Purification and properties of an enzyme in human blood and rat liver microsomes catalyzing the formation and hydrolysis of γ-lactones. II. Metal ion effects, kinetics, and equilibria," *J. Biol. Chem.*, 241(21):4842-4847 (1966).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.*, 184:821-830 (2002).
Ford et al., "Molecular properties of the lyst1+ gene and the regulation of α-aminoadipate reductase in Schizosaccharomyces pombe," *Curr. Genet.*, 28:131-137 (1995).
Fujii et al., "Error-prone rolling circle amplification: the simplest random mutagenesis protocol," _*Nat. Protoc.*, 1:2493-2497 (2006).
Fujii et al., "One-step random mutagenesis by error-prone rolling circle amplification," *Nucleic Acids Res.*, 32:e145 (2004).
Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics*, 68:144-151 (2000).
Garattini et al., "Mammalian aldehyde oxidases: genetics, evolution and biochemistry," *Cell. Mol. Life Sci.*, 65:1019-1048 (2008).
Gibbs et al., "Degenerate olignucleotide gene shuffling (DOGS): a method for enhancing the frequence of recombination with family shuffling." *Gene*, 271:13-20 (2001).
Gruez et al., "Crystal structure and kinetics identify *Escherichia coli* YdcW gene product as a medium-chain aldehyde dehydrogenase," *J. Mol. Biol.*, 343:29-41 (2004).
Guengerich, "Epoxide hydrolase: properties and metabolic roles," in *Reviews in Biochemical Toxicology*, 4th edition, Hodgson et al., (eds.), Elsevier Biomedical, New York, NY, pp. 5-30 (1982).
Guo and Bhattacharjee, "Posttranslational activation, site-directed mutation and phylogenetic analyses of the lysine biosynthesis enzymes a-aminoadipate reductase Lys1p (AAR) and the phosphopantetheinyl transferase Lys7p (PPTase) from Schizosaccharomyces pombe," *Yeast*, 21:1279-1288 (2004).
Guo and Bhattacharjee, "Site-directed mutational analysis of the novel catalytic domains of a- aminoadipate reductase (Lys2p) from Candida albicans," *Mol. Gen. Gemonics*, 269:271-279 (2003).
Gurvitz, "The essential mycobacterial genes, fabG1 and fabG4, encode 3-oxoacyl-thioester reductases that are functional in yeast mitochondrial fatty acid synthase type 2," *Mol. Genet. Genomics*, 282(4):407-416 (2009).
Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.*, 60:555-563 (2006).

Hanai et al., "Engineered synthetic pathway for isopropanol production in *Escherichia coli*," *Appl. Environ. Microbiol.*, 73(24):7814-7818 (2007).
Hawes et al., "Mammalian 3-hydroxyisobutyrate dehydrogenase," *Methods Enzymol.*, 324:218-228 (2000).
Hayes et al., "Combining computational and experimental screening for rapid optimization of protein properties," *Proc. Natl. Acad. Sci. U.S.A.*, 99(25):15926-15931 (2002).
Haywood et al., "Characterization of two 3-ketothiolases possessing differing substrate specificities in the polyhydroxyalkanoate synthesizing organism Alcaligenes eutrophus," *FEMS Microbiol. Lett.*, 52:91-96 (1988).
Hesslinger et al., "Novel keto acid formate-lyase and propionate kinase enzymes are components of an anaerobic pathway in *Escherichia coli* that degrades L-threonine to propionate," *Mol. Microbiol.*, 27:477-492 (1998).
Hibbert et al., "Directed evolution of biocatalytic processes," *Biomol. Eng.*, 22:11-19 (2005).
Hijarrubia et al., "Domain Structure Characterization of the Multifunctional α-Aminoadipate Reductase from Penicillium chrysogenum by Limited Proteolysis," *J. Biol. Chem.*, 278(10):8250-8256 (2003).
Hillmer and Gottschalk, "Solubilization and partial characterization of particulate dehydrogenases from Clostridium kluyveri," *Biochim. Biophys. Acta.*, 334:12-23 (1974).
Hiser et al., "ERG10 from *Saccharomyces cerevisiae* encodes acetoacetyl-CoA thiolase," *J. Biol. Chem.*, 269:31383-31389 (1994).
Hoffmeister et al., "Mitochondrial trans-2-enoyl-COA reductase of wax ester fermentation from Euglena gracilis defines a new family of enzymes involved in lipid synthesis," *J. Biol. Chem.*, 280(6):4329-4338 (2005).
Holtzapple and Schmidt-Dannert, "Biosynthesis of isoprenoid wax ester in marinobacter hydrocarbonoclasticus DSM 8798: identification and characterization of isoprenoid coenzyme a synthetase and wax ester synthases," *J. Bacteriol.*, 189(10):3804-3812 (2007).
Huang et al., "Identification and characterization of a second butyrate kinase from clostridium acetobutylicum ATCC 824," *J. Mol. Microbiol. Biotechnol.*,2(1):33-38 (2000).
Hugler et al., "Malonyl-Coenzyme A Reductase from Chloroflexus aurantiacus, a Key Enzyme of the 3-Hydroxypropionate Cycle for Autotrophic CO2 Fixation," *J. Bacteriol.*, 184(9):2404-2410 (2002).
Huisman and Lalonde, "Enzyme evolution for chemical process applications," In R.N. Patel (ed.), Biocatalysis in the pharmaceutical and biotechnology industries, CRC Press, p. 717-742 (2007).
Ishige et al., "Wax ester production from n-alkanes by Acinetobacter sp. strain M-1: ultrastructure of cellular inclusions and role of acyl Coenzyme A reductase," *Appl. Environ. Microbiol.*, 68(3):1192-1195 (2002).
Jeon et al., "Heterologous expression of the alcohol dehydrogenase (adhI) gene from geobacillus thermoglucosidasius strain M10EXG," *J. Biotechnol.*, 135:127-133 (2008).
Jojima et al., "Production of isopropanol by metabolically engineered *Escherichia coli*," *Appl. Microbiol. Biotechnol.*, 77:1219-1224 (2008).
Kalscheuer and Steinbuchel, "A novel bifunctional wax ester synthase/acyl-CoA:diacylglycerol acyltransferase mediates wax ester and triacylglycerol biosynthesis in acinetobacter calcoaceticus ADP1," *J. Biol. Chem.*, 278(10):8075-8082 (2003).
Kalscheuer et al., "Analysis of storage lipid accumulation in alcanivorax borkumensis: evidence for alternative triacylglycerol biosynthesis routes in bacteria," *J. Bacteriol.*, 189(3):918-928 (2007).
Kapatral et al., "Genome sequence and analysis of the oral bacterium fusobacterium nucleatum strain ATCC 25586," *J. Bact.*, 184(7) 2005-2018 (2002).
Karlen et al., "Absolute determination of the activity of two C14 dating standards," in *Arkiv For Geofysik*, 4:465-471 (1968).
Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.*, 43(1):43-55 (1972).
Kessler et al., "Pyruvate-formate-lyase-deactivase and acetyl-CoA reductase activities of *Escherichia coli* reside on a polymeric protein particle encoded by adhE," *FEBS Lett.*, 281(1-2):59-63 (1991).

(56) References Cited

OTHER PUBLICATIONS

Khalameyzer et al., "Screening, nucleotide sequence, and biochemical characterization of an esterase from pseudomonas fluorescens with high activity towards lactones," Appl. Environ. Microbiol., 65(2):477-482 (1999).

Kinoshita, "Purification of two alcohol dehydrogenases from Zymomonas mobilis and their properties," Appl. Microbiol. Biotechnol., 22:249-254 (1985).

Klatt et al., "Comparative genomics provides evidence for the 3-hydroxypropionate autotrophic pathway in filamentous anoxygenic phototrophic bacteria and in hot spring microbial mats," Environ. Microbiol., 9:2067-2078 (2007).

Knutzon et al, "Isolation and characterization of two safflower oleoyl-acyl carrier protein thioesterase cDNA clones," Plant Physiol., 100:1751-1758 (1992).

Koo et al., "Cloning and characterization of the bifunctional alcohol/acetaldehyde dehydrogenase gene (adhE) in Leuconostoc mesenteroides isolated from kimchi," Biotechnol. Lett., 27(7):505-510 (2005).

Kosaka et al., "Characterization of the sol operon in butanol-hyperproducing Clostridium saccharoperbutylacetonicum strain N1-4 and its degeneration mechanism," Biosci. Biotechnol. Biochem., 71:58-68 (2007).

Kreimeyer et al., "Identification of the Last Unknown Genes in the Fermentation Pathway of Lysine," J. Biol. Chem., 282(10):7191-7197 (2007).

Kretz et al., "Gene Site Saturation Mutagenesis: A Comprehensive Mutagenesis Approach," Methods Enzymol., 388:3-11 (2004).

Kuznetsova et al., "Enzyme genomics: Application of general enzymatic screens to discover new enzymes," FEMS Microbiol. Rev., 29(2):263-279 (2005).

Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," Biochem. J., 395(1):147-155 (2006).

Lardizabel et al., "Purification of a jojoba embryo wax synthase, cloning of its cDNA, and production of high levels of wax in seeds of transgenic arabidopsis," Plant Physiology, 122:645-655 (2000).

Leduc et al., "The hotdog thioesterase EntH (YbdB) plays a role in vivo in optimal enterobactin biosynthesis by interacting with the ArCP domain of EntB," J. Bacteriol., 189(19):7112-7126 (2007).

Lee et al., "A new approach to directed gene evolution by recombined extension on truncated templates (RETT)," J. Molec. Catalysis, 26:119-129 (2003).

Lee et al., "Biosynthesis of enantiopure (S)-3-hydroxybutyric acid in metabolically engineered Eschericha coli," Appl. Microbiol. Biotechnol., 79:633-641 (2008).

Leuchs and Greiner, "Alcohol dehydrogenase from lactobacillus brevis: a versatile robust catalyst for enantioselective transformations," Chem. Biochem. Eng. Quarterly, 25(2):267-281 (2011).

Lin et al., "Fed-batch culture of a metabolically engineered Escherichia coli strain designed for high-level succinate production and yield under aerobic conditions," Biotechnol. Bioeng., 90:775-779 (2005).

Lobo et al, "A streptomyces collinus thiolase with novel acetyl-CoA:Acyl carrier protein transacylase activity," Biochem., 40:11955-11964 (2001).

Lokanath et al., "Crystal structure of novel NADP-dependent 3-hydroxyisobutyrate dehydrogenase from Thermus thermophilus HB8," J. Mol. Biol., 352(4):905-917 (2005).

Lomakin et al., "The crystal structure of yeast fatty acid synthase, a cellular machine with eight active sites working together," Cell, 129(2):319-332 (2007).

Louis et al., "Restricted distribution of the butyrate kinase pathway among butyrate-producing bacteria from the human colon," J. Bacteriol., 186(7):2099-2106 (2004).

Low et al., "Mimicking somatic hypermutation: affinity maturation of antibodies displayed on baceriophage using a bacterial mutator strain," J. Mol. Biol., 260(3):359-368 (1996).

Lutz et al., "Creating multiple-crossover DNA libraries independent of sequence identity," Proc. Natl. Acad. Sci. U.S.A., 98:11248-11253 (2001).

Lutz et al., "Rapid generation of incremental truncation libraries for protein engineering using α-phosphothioate nucleotides," Nucleic Acids Res., 29:E16 (2001).

Mack and Buckel, "Conversion of glutaconate CoA-transferase from Acidaminococcus fermentans into an acyl-CoA hydrolase by site-directed mutagenesis," FEBS Lett., 405(2):209-212 (1997).

Mann, "An International Reference Material for Radiocarbon Dating," Radiocarbon, 25(2):519-527 (1983).

Manning and Pollitt, "Tracer studies of the interconversion of R- and S-methylmalonic semialdehydes in man," Biochem. J., 231(2):481-484 (1985).

Martínez-Blanco, et al, "Purification and biochemical characterization of phenylacetyl-CoA ligase from Pseudomonas putida. A specific enzyme for the catabolism of phenylacetic acid," J. Biol. Chem., 265(12):7084-7090 (1990).

Mason and Dufour, "Alcohol acetyltransferases and the significance of ester synthesis in yeast," Yeast, 16:1287-1298 (2000).

Matsumoto et al, "A new pathway for poly(3-hydroxybutyrate) production in Escherichia coli and corynebacterium glutamicum by functional expression of a new acetoacetyl-coenzyme a synthase," Biosci. Biotech. Biochem., 75:364-366 (2011).

Merilainen et al., "The thiolase reaction mechanism: the importance of Asn316 and His348 for stabilizing the enolate intermediate of the claisen condensation," Biochem., 48:1111-11025 (2009).

Metz et al., "Purification of a jojoba embryo fatty acyl-Coenzyme A reductase and expression of its cDNA in high erucic acid rapeseed," Plant Phys., 122:635-644 (2000).

Moore et al., "Advances in the enzymatic reduction of ketones," Acc. Chem. Res., 40(12):1412-1419 (2007).

Morris and Jinks-Robertson, "Nucleotide sequence of the LYS2 gene of Saccharomyces cerevisiae: homology to Bacillus brevis tyrocidine synthetase 1," Gene, 98:141-145 (1991).

Muller et al., "Nucleotide exchange and excisiion technology (NExT) DNA shuffling; a robust method for DNA fragmentation and directed evolution," Nucleic Acids Res., 33:e117 (2005).

Musfeldt and Schönheit, "Novel type of ADP-forming acetyl Coenzyme A synthetase in hyperthermophilic archaea: heterologous expression and characterization of isoenzymes from the sulfate reducer Archaeoglobus fulgidus and the methanogen Methanococcus jannaschii," J. Bacteriol., 184(3):636-644 (2002).

Naggert et al., "Cloning, sequencing, and characterization of Escherichia coli thioesterase II," J. Biol. Chem.,nag 266(17):11044-11050 (1991).

Nardi et al., "The EstA esterase is responsible for the main capacity of lactococcus lactis to synthesize short chain fatty acid esters in vitro," J. Appl. Microbiol., 93:994-1002 (2002).

Navarro-Avino et al., "A proposal for nomeclature of aldehyde dehydrogenases in Saccharaomyces cerevisiae and characterization of the stress-inducible ALD2 and ALD3 genes," Yeast, 15:829-842 (1999).

Ness et al., "Synthetic shuffling expands functional protein diversity by allowing amino acids to recombine independently," Nat. Biotechnol., 20:1251-1255 (2002).

Nguyen et al., "Fatty acid synthase impacts the pathobiology of Candida parapsilosis in vitro and during mammalian infection," PLoS One, 4(12):e8421 (2009).

Noichinda et al., "Subcellular localization of alcohol acetyltransferase in strawberry fruit," Food Sci. Technol. Res., 5(3):239-242 (1999).

Ohgami et al., "Expression of acetoacetyl-CoA synthetase, a novel cytosolic ketone body-utilizing enzyme, in human brain," Biochem. Pharmacol., 65:989-994 (2003).

Okamura et al, "Unprecedented acetoacetyl-coenzyme A synthesizing enzyme of the thiolase superfamily involved in the mevalonate pathway," Proc. Natl. Acad. Sci. USA, 107:11265-70 (2010).

Ostermeier et al., "A Combinatorial approach to hybrid enzymes independent of DNA homology," Nat. Biotechnol., 17:1205-1209 (1999).

Ostermeier et al., "Combinatorial protein engineering by incremental truncation," Proc. Natl. Acad. Sci. U.S.A., 96:3562-3567 (1999).

Otten and Quax, "Directed evolution: selecting today's biocatalysts," Biomol. Eng. (22):1-9 (2005).

Perez et al., "Escherichia coli YqhD exhibits aldehyde reductase activity and protects from the harmful effect of lipid peroxidation-derived aldehydes," J. Biol. Chem., 283(12):7346-7353 (2008).

(56) References Cited

OTHER PUBLICATIONS

Ploux et al., "The NADPH-linked acetoacetyl-COA reductase from Zoogloea ramigera, Characterization and mechanistic studies of the cloned enzyme over-produced in *Escherichia coli*," *Eur. J. Biochem.*, 174:177-182 (1988).
Powlowski et al., "Purification and properties of the physically associated meta-cleavage pathway enzymes 4-hydroxy-2-ketovalerate aldolase and aldehyde dehydrogenase (acylating) from Pseudomonas sp. strain CF600," *J. Bacteriol.* 175(2):377-385 (1993).
Preisig-Muller et al., "Domains of the tetrafunctional protein acting in glyoxysomal fatty acid beta-oxidation. Demonstration of epimerase and isomerase activities on a peptide lacking hydratase activity," *J. Biol. Chem.*, 269(32):20475-2081 (1994).
Pritchard et al., "A general model of error-prone Pcr," *J. Theor. Biol.*, 234:497-509 (2005).
Quash et al., "Novel competitive irreversible inhibitors of aldehyde dehydrogenase (ALDH1): restoration of chemosensitivity of L1210 cells overexpressing ALDH1 and induction of apoptosis in BAF$_3$ cells overexpressing bcl$_2$," *Biochem. Pharmacol.*, 64:1279-1292 (2002).
Rajpai et al., "A general method for greatly improving the affinity of antibodies by using combinatorial libraries," *Proc. Natl. Acad. Sci. U.S.A.*, 102:8466-8471 (2005).
Reetz and Carballeira, "Iterative saturation mutagenesis (ISM) for rapid directed evolution of functional enzymes," *Nat. Protoc.*, 2:891-903 (2007).
Reetz et al., "Directed Evolution of an Enantioselective Enzyme through Combinatorial Multiple- Cassette Mutagenesis," *Angew. Chem. Int. Ed. Engl.*, 40:3589-3591 (2001).
Reetz et al., "Iterative saturation mutagenesis on the basis of B factors as a strategy for incresing protein thermostability," *Angew. Chem. Int. Ed,.* 45:7745-7751 (2006).
Reidhaar-Olson and Sauer, "Combinatorial cassette mutagenesis as a probe of the informational content of protein sequences," *Science*, 241:53-57 (1988).
Reidhaar-Olson et al., "Random mutagenesis of protein sequences using oligonucleotide cassettes," *Methods Enzymol.*, 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase," *J. Bacteriol.*, 179(9):2969-2975 (1997).
Riviere et al., "Acetyl:succinate CoA-transferase in procyclic Trypanosoma brucei. Gene identification and role in carbohydrate metabolism." *J. Biol. Chem.*, 279:45337-45346 (2004).
Rochu et al., "Stabilization of the active form(s) of human paraoxonase by human phosphate-binding protein," *Biochem. Soc. Trans.*, 35(6):1616-1620 (2007).
Rodriguez-Zavala et al., "Characterization of *E. coli* tetrameric aldehyde dehydrogenases with atypical properties compared to other aldehyde dehydrogenases," *Protein Sci.*, 15:1387-1396 (2006).
Salas et al., "Characterization of substrate specificity of plant FatA and FatB acyl-ACP thioesterases," *Arch. Biochem. Biophys.*, 403(1):25-34 (2002).
Schirmer et al, "Microbial biosynthesis of alkanes," *Science*, 329:559-562 (2010).
Seedorf et al., "The genome of Clostridium kluyveri, a strict anaerobe with unique metabolic features," *Proc. Natl. Acad. Sci. U.S.A.*, 105:2128-2133 (2008).
Sekimoto et al., "Cloning and molecular characterization of plant aldehyde oxidase," *J. Biol. Chem.*, 272(24):15280-15285 (1997).
Selifonova et al., "Rapid evolution of novel traits in microorganisms," *Appl. Environ. Microbiol.*, 67:3645-3649 (2001).
Sen et al., "Developments in directed evolution for improving enzyme functions," *Appl. Biochem. Biotechnol.*, 143:212-223 (2007).
Shao et al., "Random-priming in vitro recombination: an effective tool for directed evolution," *Nucleic Acids Res.*, 26:681-683 (1998).
Shimakata et al, "Purification of plant acetyl-CoA:acyl carrier protein transacylase," *Methods Enzymol.*, 122:53-59 (1986).

Shimomura et al., "3-hydroxyisobutyryl-CoA-hydrolase," *Methods Enzymol.*, 324:229-240 (2000).
Shimomura et al., "Purification and partial characterization of 3-hydroxyisobutyryl-Coenzyme A hydrolase of rat liver," *J. Biol. Chem.*, 269(19): 14248-14253 (1994).
Sieber et al., "Libraries of hybrid proteins from distantly related sequences," *Nat. Biotechnol.*, 19:456-460 (2001).
Simon et al., "cDNA cloning of *Brassica napus* malonyl-CoA:ACP transacylase (MCAT) (fab D) and complementation of an *E. coli* MCAT mutant," *FEBS Letts.*, 435:204-206 (1998).
Skarstedt and Silverstein, "n *Escherichia coli* acetate kinase mechanism studied by net initial rate, equuilibrium, and independent isotopic exchange kinetics," *J. Biol. Chem.* 251:6775-6783 (1976).
Smith et al, "Structural and functional organization of the animal fatty acid synthase," *Prog. Lipid Res.*, 42:289-317 (2003).
Smith et al., "Purification and characteristics of a γ-glutamyl kinase involved in *Escherichia coli* proline biosynthesis," *J. Bacteriol.*, 157(2):545-551 (1984).
Smith, "The animal fatty acid synthase: one gene, one polypeptide, seven enzymes," *FASEB J.*, 8(15):1248-1259 (1994).
Snell et al., "YfcX enables medium-chain-length poly(3-hydroxyalkanoate) formation from fatty acids in recombinant *Escherichia coli* fadB strains," *J. Bacteriol.*, 184(20):5696-5705 (2002).
Söhling and Gottschalk, "Molecular analysis of the anaerobic succinate degradation pathway in Clostridium kluyveri," *J. Bacteriol.*, 178:871-880 (1996).
Song et al., "Structure, function, and mechanism of the phenylacetate pathway hot dog-fold thioesterase PaaI," *J. Biol. Chem.*, 281(16):11028-11038 (2006).
Soubrier et al., "Cloning and primary structure of the wide-spectrum amidase from Brevibacterium sp. R312: high homology to the amiE product from Pseudomonas aeruginosa," *Gene*, 116(1):99-104 (1992).
Stemmer, "DNA shuffling by random fragmentation and reassembly: in vitro recombination for molecular evolution," *Proc. Natl. Acad. Sci. U.S.A.*, 91:10747-10751 (1994).
Stemmer, "Rapid evolution of a protein in vitro by DNA shuffling," *Nature*, 370:389-391 (1994).
Stols et al., "New vectors for co-expression of proteins: Structure of *Bacillus subtilis* ScoAB obtained by High-throughput protocols," *Protein Expr. Purif.*, 53:396-403 (2007).
Strauss and Fuchs, "Enzymes of a novel autotrophic CO2 fixation pathway in the phototrophic bacterium Chloroflexus aurantiacus, the 3-hydroxypropionate cycle," *Eur. J. Biochem.*, 215:633-643 (1993).
Suematsu et al., "Molecular cloning and functional expression of rat liver cytosolic acetyl-CoA hydrolase," *Eur. J. Biochem.*, 268:2700-2709 (2001).
Sulzenbacher et al., "Crystal structure of *E.coli* alcohol dehydrogenase YqhD: evidence of a covalently modified NADP Coenzyme," *J. Mol. Biol.*, 342(2):489-502 (2004).
Sumper, "Acetyl-CoA carboxylase from yeast," *Methods Enzymol.*, 71(Pt. C):34-37 (1981).
Suzuki et al., "GriC and GriD Constitute a carboxylic acid reductase involved in grixazone biosynthesis in streptomyces griseus," *J. Antibiot.*, 60(6):380-387 (2007).
Suzuki, "Phosphotransacetylase of *Escherichia coli* B, Activation by Pyruvate and Inhibition by NADH and Certain Nucleotides," *Biochim. Biophys. Acta*, 191:559-569 (1969).
Takahashi and Yamada, "Metabolic pathways for cytoxic and end product formation from glutamate- and aspartate-containing peptides by Porphyromonas gingivalis," *J. Bacteriol.* 182:4704-4710 (2000).
Tan and Miller, "Cloning, expression, and nucleotide sequence of a lipase gene from pseudomonas fluorescens B52," *Appl. Environ. Microbiol.*, 58(4):1402-1407 (1992).
Tanaka et al., "Cloning and characterization of a human orthologue of testis-specific succinyl CoA: 3-oxo acid CoA transferase (Scot-t) cDNA," *Mol. Hum. Reprod.*, 8:16-23 (2002).
Tani et al., "Thermostable NADP+-dependent medium-chain alcohol dehydrogenase from Acinetobacter sp. strain M-1: purification and characterization and gene expression in *Escherichia coli*," *Appl. Environ. Microbiol.*, 66(12):5231-5235 (2000).

(56) References Cited

OTHER PUBLICATIONS

Thauer, "Microbiology. A Fifth Pathway of Carbon Fixation," *Science* 318:1732-1733 (2007).
Thiery et al., "Acyltransferase activity of the wide spectrum amidase of brevibacterium sp. R312," *J. Gen. Microbiol.*, 132:2205-2208 (1986).sou.
Toth et al., "The ald Gene, Encoding a Coenzyme A—Acylating Aldehyde Dehydrogenase, Distinguishes Clostridium beijerinckii and Two Other Solvent-Producing Clostridia from Clostridium acetobutylicum," *App. Environ. Microbiol.*, 65(11):4973-4980 (1999).
Tseng et al., "Metabolic engineering of *Escherichia coli* for enhanced production of (R)- and (S)-3- hydroxybutyrate," *Appl. Environ. Microbiol.*, 75(1):3137-3145 (2009).
Vamecq et al., "The microsomal dicarboxylyl-CoA synthetase," *Biochem. J.*, 230(3):683-693 (1985).
Van Grinsven et al., "Acetate:succinate CoA-transferase in the hydrogenosomes of Trichomonas vaginalis: identification and characterization," *J. Biol. Chem.*, 283:1411-1418 (2008).
Vazquez et al., "Phosphotransbutyrylase expression in *Bacillus megaterium*," *Curr. Microbiol.*, 42:345-349 (2001).
Venkitasubramanian et al. in *Biocatalysis in the Pharmaceutical and Biotechnology Industires*, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.*, 282(1):478-485 (2007).
Verwoert et al, "Cloning, nucleotide sequence, and expression of the *Escherichia coli* fabD gene, encoding malonyl coenzyme A—Acyl carrier protein transacylase," *J. Bacteriol.*, 174:2851-2857 (1992).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27:e18 (1999).
Wahlen et al., "Purification, characterization, and potential bacterial wax production role of an NADPH-dependent fatty aldehyde reductase from Marinobacter aquacolei VT8," *Appl. Environ. Microbiol.*, 75(9):2758-2764 (2009).
Wakil et al., "Studies on the fatty acid oxidizing system of animal tissues. VI. β-Hydroxyacyl Coenzyme A dehydrogenase," *J. Biol. Chem.*, 207(2):631-638 (1954).
Walter et al., "Molecular characterization of two Clostridium acetobutylicum ATCC 824 butanol dehydrogenase isozyme genes," *J. Bacteriol.*, 174(22):7149-7158 (1992).
Walter et al., "Sequence and arrangement of two genes of the butyrate-synthesis pathway of clostridium acetobutylicum ATCC 824," *Gene*, 134:107-111 (1993).
Wang et al, "Molecular cloning and functional identification of a novel phenylacetyl-CoA ligase gene from Penicillium chrysogenum," *Biochem. Biopyhs. Res. Commun.*, 360(2):453-458 (2007).

Westin et al., "The identification of a succinyl-CoA thioesterase suggests a novel pathway for succinate production in peroxisomes," *J. Biol. Chem.*, 280(46):38125-38132 (2005).
Wiesenborn et al., "Coenzyme A Transferase from clostridium acetobutylicum ATCC 824 and Its Role in the Uptake of Acids," *Appl. Environ. Microbiol.*, 55(2):323-329 (1989).
Winzer et al., "Differential regulation of two thiolase genes from Clostridium acetobutylicum DSM 792," *J. Mol. Microbiol. Biotechnol.*, 2(4):531-541 (2000).
Wolff and Kenealy, "Purification and characterization of the oxygen-sensitive 4-hydroxybutanoate dehydrogenase from Clostridium kluyveri," *Protein Expr. Purif.*, 6:206-212 (1995).
Wong et al., "Sequence saturation mutagenesis (SeSaM): a novel method for directed evolution," *Nucleic Acids Res.*, 32:e26 (2004).
Wong et al., "Sequence saturation mutagenesis with tunable mutation frequencies," *Anal. Biochem.*. 341:187-189 (2005).
Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3:74-82 (2008).
Yang and Elzinga, "Association of both enoyl coenzyme A hydratase and 3-hydroxyacyl coenzyme A epimerase with an active site in the amino-terminal domain of the multifunctional fatty acid oxidation protein from *Escherichia coli*," *J. Biol. Chem.*, 268(9):6588-6592 (1993).
Yilmaz et al., "Enhanced stress tolerance in *Escherichia coli* and nicotiana tabacum expressing a betaine aldehyde dehydrogenase/choline dehydrogenase fusion protein," *Biotechnol.*, 18:1176-1182 (2002).
Yoshioka and Hashimoto, "Ester formation by alcohol acetyltransferase from brewer's yeast," *Agric. Biol. Chem.*, 45(10):2183-2190 (1981).
Youngleson et al., "Homology between hydroxybutyryl and hydroxyacyl Coenzyme A dehydrogenase enzymes from Clostridium acetobutylicum fermentation and vertebrate fatty acid β-oxidation pathways," *J. Bacteriol.*, 171(12):6800-6807 (1989).
Zaccai et al., "Crystal structure of a 3-oxoacyl-(acylcarrier protein) reductase (BA3989) from *Bacillus anthracis* at 2.4—A resolution," *Proteins*, 70(2):562-567 (2008).
Zeiher and Randall, "Identification and characterization of Mitochondrial Acetyl-Coenzyme A Hydrolase from Pisum sativum L. Seedlings," *Plant. Physiol.*, 94:20-27 (1990).
Zhang et al., "Isolation and properties of a levo-lactonase from Fusarium proliferatum ECU2002: a robust biocatalyst for production of chiral lactones," *Appl. Microbiol. Biotechnol.*, 75(5):1087-1094 (2007).
Zhang et al., "Key residues responsible for acyl carrier protein and beta-ketoacyl-acyl carrier protein reductase (FabG) interaction," *J. Biol. Chem.*, 278(52):52935-52943 (2003).
Zhao et al., "Molecular evolution by staggered extension process (StEP) in vitro recombination," *Nat. Biotechnol.*, 16:258-261 (1998).
Zhuang et al., "The YbgC protein encoded by the ybgC gene of the tol-pal gene cluster of haemophilus influenzae catalyzes acyl-coenzyme A thioester hydrolysis," *FEBS Letts.*, 516:161-163 (2002).

\* cited by examiner

MICROORGANISMS AND METHODS FOR PRODUCING (3R)-HYDROXYBUTYL (3R)-HYDROXYBUTYRATE

This application is a 371 national stage application of PCT/US2014/039322, filed on May 23, 2014, which in turn claims the benefit of priority of U.S. Provisional Application Ser. No. 61/887,219, filed Oct. 4, 2013, and U.S. Provisional Application Ser. No. 61/827,492, filed May 24, 2013, the entire contents of which are each incorporated herein by reference and for all purposes.

BACKGROUND

The present application relates generally to biosynthetic production of (3R)-hydroxybutyl (3R)-hydroxybutyrate, and more specifically to non-naturally occurring microbial organisms having pathways for production of (3R)-hydroxybutyl (3R)-hydroxybutyrate, methods and processes for producing (3R)-hydroxybutyl (3R)-hydroxybutyrate using the microbial organisms, bioderived (3R)-hydroxybutyl (3R)-hydroxybutyrate, compositions having bioderived (3R)-hydroxybutyl (3R)-hydroxybutyrate, and methods of treating or preventing a disease, disorder or condition using the bioderived (3R)-hydroxybutyl (3R)-hydroxybutyrate.

Ketone bodies are chemical compounds which are produced when fatty acids are metabolized by the body for energy, which can in turn lead to the ketone bodies themselves being used for energy. Metabolization of fatty acids generally occurs during mild ketosis. Mild ketosis can be induced in an individual who consumes a high fat, low carbohydrate diet, commonly termed a "ketogenic diet." The ketogenic diet generally includes four parts fat to one part protein with minimal carbohydrate intake. Induction of mild ketosis through use of such a ketogenic has been suggested as a possible treatment for several diseases.

Moreover, ketone bodies have been shown as being suitable for reducing the levels of free fatty acids circulating in the plasma of an individual. Ingestion of ketone bodies can lead to various clinical benefits, including an enhancement of physical and cognitive performance and treatment of cardiovascular conditions, diabetes and treatment of mitochondrial dysfunction disorders and in treating muscle fatigue and impairment. However, direct administration of ketone bodies is impractical and dangerous. For example, direct administration of either (R)-3-hydroxybutyrate can result in significant acidosis following rapid absorption from the gastrointestinal tract. Administration of the sodium salt of these compounds is also unsuitable due to a potentially dangerous sodium overload that would accompany administration of therapeutically relevant amounts of these compounds. Administration of (R)-3-hydroxybutyrate derivatives in oligomeric form has been used to circumvent this problem.

The intake of compounds and compositions containing (R)-3-hydroxybutyrate derivatives, e.g. (3R)-hydroxybutyl (3R)-hydroxybutyrate, have been shown to boost the levels of ketone bodies in the blood. To gain desirable therapeutic and other benefits, the ketone body generally needs to be present in the blood plasma of an individual at a threshold level, for example at least 1 mM.

Synthesis of steriogenic mixtures of 3-hydroxybutyl 3-hydroxybutyrate has been previously shown. Because the (3R,3'R) isomer is the most effective precursor of (3R)-hydroxybutyrate, and is a ketone body biosynthesized and utilized in vivo, various synthetic approaches have been developed for the production of the desired (3R,3'R) isomeric rich product. However, low yields, the production of impure product, and impracticability on a large scale have hindered production. For example, a classical synthesis, from poly[(3R)-hydroxybutyric acid], gives pure product, but involves six chemical steps.

Accordingly, there exists a need to produce a stereogenic purified product of (3R)-hydroxybutyl (3R)-hydroxybutyrate on a large scale. The present invention satisfies this need and provides related advantages as well.

SUMMARY

In one embodiment, provided herein is a non-naturally occurring microbial organism having a pathway for production of (3R)-hydroxybutyl (3R)-hydroxybutyrate, wherein the organism includes at least one exogenous nucleic acid encoding a (3R)-hydroxybutyl (3R)-hydroxybutyrate pathway enzyme disclosed herein that is expressed in a sufficient amount to produce (3R)-hydroxybutyl (3R)-hydroxybutyrate. These microbial organisms can further include a (R)-1,3-butanediol pathway, a (3R)-hydroxybutyrate pathway, a (3R)-hydroxybutyryl-CoA pathway, an acetoacetate pathway, an acetoacetyl-CoA pathway, a (3R)-hydroxybutyl-ACP pathway, an acetoacetyl-ACP pathway or any combination thereof.

Also provided herein are methods and processes for producing (3R)-hydroxybutyl (3R)-hydroxybutyrate using the microbial organisms. The bioderived (3R)-hydroxybutyl (3R)-hydroxybutyrate produced by the microbial organisms of the invention can be formulated into various compositions having bioderived (3R)-hydroxybutyl (3R)-hydroxybutyrate. Still further provided are methods of treating or preventing a disease, disorder or condition using the bioderived (3R)-hydroxybutyl (3R)-hydroxybutyrate produced by the microbial organisms of the invention.

DETAILED DESCRIPTION

Figure 1:
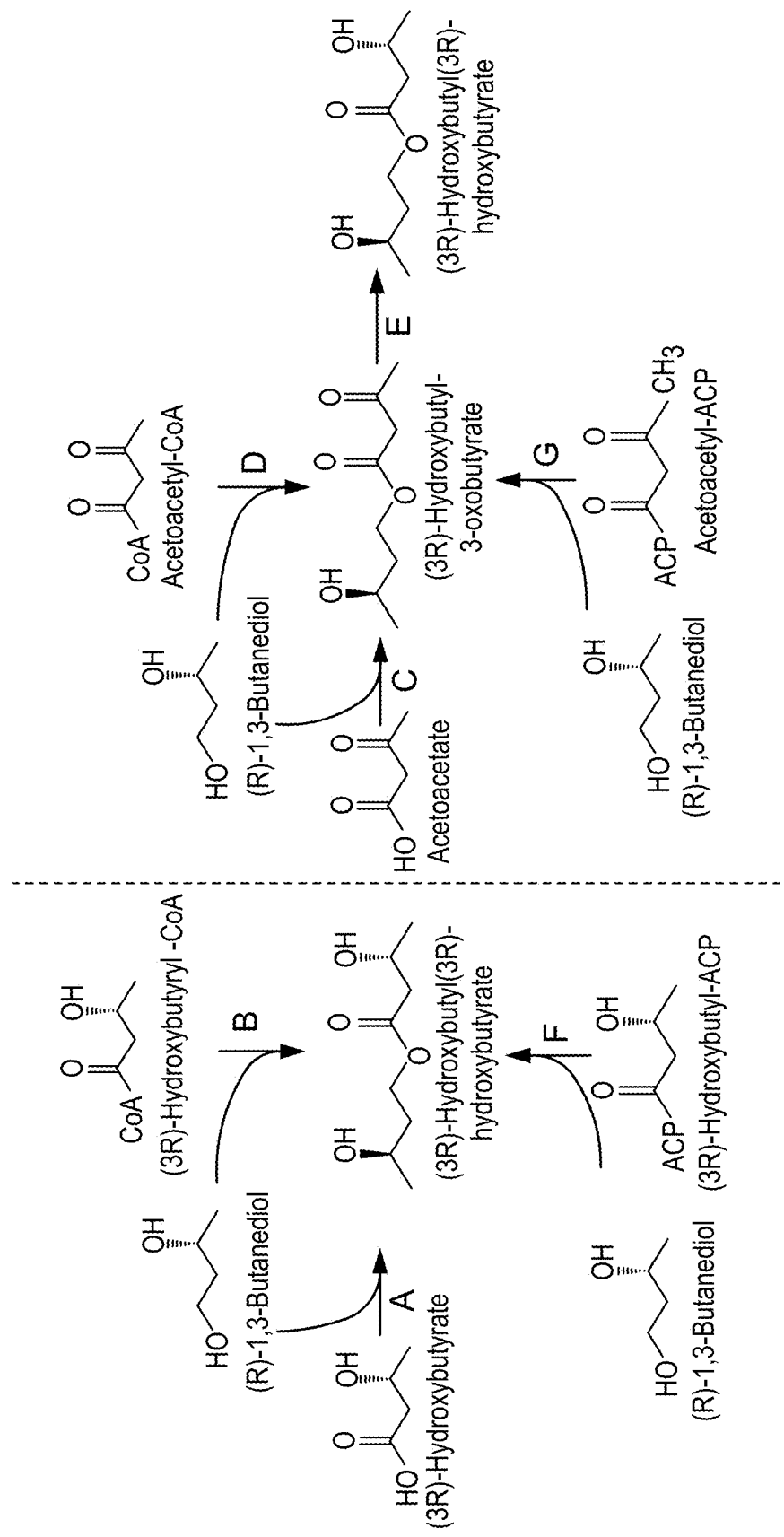
FIG. 1 shows exemplary pathways for the production of (3R)-hydroxybutyl (3R)-hydroxybutyrate from (R)-1,3-butanediol and (3R)-hydroxybutyryl-CoA, (3R)-hydroxybutyrate, (3R)-hydroxybutyl-ACP, acetoacetate, acetoacetyl-CoA or acetoacetyl-ACP. Enzymes are: A. (3R)-hydroxybutyl (3R)-hydroxybutyrate ester forming enzyme or non-enzymatic, B. (3R)-hydroxybutyryl-CoA:(R)-1,3-butanediol alcohol transferase, C. (3R)-hydroxybutyl 3-oxobutyrate ester forming enzyme or non-enzymatic, D. acetoacetyl-CoA:(R)-1,3-butanediol alcohol transferase, E. (3R)-hydroxybutyl 3-oxobutyrate reductase, F. (3R)-hydroxybutyryl-ACP:(R)-1,3-butanediol ester synthase, and G. acetoacetyl-ACP:(R)-1,3-butanediol ester synthase.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a (3R)-hydroxybutyl (3R)-hydroxybutyrate biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the term "purified" when used in reference to a compound is intended to mean a compound that is substantially free of at least one component as the referenced compound is found in nature or as the referenced compound is found in a non-naturally occurring environment, e.g. in a non-naturally occurring microbial organism or the culture medium wherein the compound is biosynthesized as described herein. The term also includes a compound that is removed from some or all components from which it is found. Thus, the term purified includes a compound that is removed from some or all components as the compound is found in a non-naturally occurring environment. A purified compound can be partly or completely separated from other substances as it is found in nature or as it is found, synthesized, accumulated or stored in non-naturally occurring environments. Specific examples of purified compounds include partially pure compounds, substantially pure compound and compounds present in a culture medium that is non-naturally occurring, from which the cell mass of a microbial organism described herein has been removed.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "ACP" or "acyl carrier protein" refers to any of the relatively small acidic proteins that are associated with the fatty acid synthase system of many organisms, from bacteria to plants. ACPs can contain one 4'-phosphopantetheine prosthetic group bound covalently by a phosphate ester bond to the hydroxyl group of a serine residue. The sulfhydryl group of the 4'-phosphopantetheine moiety serves as an anchor to which acyl intermediates are (thio)esterified during fatty-acid synthesis. An example of an ACP is *Escherichia coli* ACP, a separate single protein, containing 77 amino-acid residues (8.85 kDa), wherein the phosphopantetheine group is linked to serine 36.

As used herein, the term "(3R)-hydroxybutyl (3R)-hydroxybutyrate" refers to a compound of formula (I):

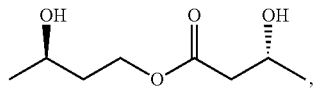

as depicted in FIG. 1. The term (3R)-hydroxybutyl (3R)-hydroxybutyrate is used interchangeably throughout with the terms (R)—(R)-3-hydroxybutyl 3-hydroxybutanoate, (3R)-hydroxybutyl(3R)-hydroxybutyrate, and (R)-3-hydroxybutyl (R)-3hydroxybutanoate.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acid refers to the referenced encoding nucleic acid or biosynthetic activity, as discussed above. It is further understood, as disclosed herein, that such more than one exogenous nucleic acid can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli, and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3'exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having (3R)-hydroxybutyl (3R)-hydroxybutyrate biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The term "condition" refers to a state of ill health or sickness.

The term "disease" refers a condition characterized by functional impairment, structural change, and the presence of specific signs and symptoms.

The term "disorder," in contrast to disease, denotes a condition characterized by functional impairment without structural change. While certain disorders or categories of disorders might be accompanied by specific signs and symptoms, their presence is not required for a condition to be termed a disorder.

A "food product" is an edible material composed primarily of one or more macronutrients such as protein, carbohydrate or fat, which is used in the body of an organism to sustain growth, repair damage, aid vital processes or furnishes energy. A food product can also contain one or more micronutrients such as vitamins or minerals, or additional dietary ingredients such as flavorants and colorants. Non-limiting examples of food products into which the (3R)-hydroxybutyl (3R)-hydroxybutyrate of the invention can be incorporated as an additive include snack bars, meal replacement bars, cereals, confectionery and probiotic formulations including yoghurts.

A "beverage" refers to a liquid suitable for consumption. Non-limiting examples of a beverage include soft beverages, energy drinks, nutritional beverages, meal or food replacement drinks, compositions for rehydration (formulated to consumption during or after exercise), and herbal teas for infusion or herbal blends for decoction in water.

A "drink," as used herein, refers to a beverage that includes alcohol, such as, a mixed-drink, beer, or wine.

A "nutraceutical" refers to a food ingredient that is considered to provide a medical or health benefit, including the prevention and treatment of a disease, disorder or condition. A nutraceutical can be specifically adapted to confer a particular health benefit on the consumer. A nutraceutical can also include a micronutrient as mentioned above at a higher level than would be found in a corresponding regular food product. That level is can selected to optimize the intended health benefit of the nutraceutical when taken either as a single serving or as part of a diet regimen or course of nutritional therapy. The level of micronutrients of the compositions of the present invention can be a level effective to reduce plasma levels of fatty acids.

A "dietary supplement" refers to a non-food substance intended to supplement an organism's diet by providing nutrients, such as vitamins, minerals, fiber, fatty acids, or amino acids that may be missing or may not be consumed in sufficient quantities.

A "functional food" is a food that is marketed as providing a health benefit beyond that of supplying pure nutrition to the consumer. A functional food can incorporate an ingredient such as a micronutrient as mentioned above, which confers a specific medical or physiological benefit other than a nutritional effect. A functional food can carry a health claim on the packaging.

A "pharmaceutical composition" refers to a composition that combines the (3R)-hydroxybutyl (3R)-hydroxybutyrate of the invention with a pharmaceutically acceptable carrier, inert or active, for example, sterile water, an iso-osmotic solution, a solid excipient, or a solid support, making the composition suitable for therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Remington: The Science and Practice of Pharmacy, Lippincott Williams & Wilkins, Twenty-First edition (May 19, 2005).

An "effective amount" is an amount sufficient to effect beneficial or desired results.

The term "nutritionally effective amount" refers to an amount that facilitates or allows an organism to assimilate food or to grow.

The term "therapeutically effective amount" refers to an amount that is sufficient to reduce the symptoms of, arrest or reduce the progression of, treat or prevent a disease, disorder or condition.

It is understood that an effective amount, nutritionally effective amount or a therapeutically effective amount can be administered in one or more administrations, applications or dosages. Such delivery is dependent on a number of variables including the time period for which the individual dosage unit is to be used, the bioavailability of the compound of the invention, the route of administration, etc. It is also understood that specific dose levels of the compound of the present invention for any particular subject can depend upon factors such as the age, body weight, general health, sex, and diet of the subject, the time of administration, the rate of excretion, the drug combination, and the severity of the particular disease, disorder or condition being treated or prevented and form of administration. Dosage-effect relationships from in vitro and/or in vivo tests initially can be used to provide useful guidance on the proper doses for administration.

A "flavoring" refers to a substance that assists in providing a palatable product by altering or enhancing the taste of a composition.

The term "treating" or "treatment," as it is used herein is intended to mean an amelioration of a clinical symptom indicative of a disease, disorder or condition. Amelioration of a clinical symptom can include a decrease or reduction in at least one symptom of the disease, disorder or condition in a treated individual compared to pretreatment levels or compared to an individual having the same disease, disorder or condition.

The term "preventing" or "prevention," as it is used herein is intended to mean a forestalling of a clinical symptom indicative of a disease, disorder or condition. Such forestalling can include the maintenance of normal physiological indicators in an individual prior to developing overt symptoms of the disease, disorder or condition or prior to diagnosis of the disease, disorder or condition. Therefore, preventing can include the prophylactic treatment of individuals to guard them from the occurrence of a disease, disorder or condition. Preventing a disease, disorder or condition in an individual also is intended to include inhibiting or arresting the development of a disease, disorder or condition.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

The compound (3R)-hydroxybutyl (3R)-hydroxybutyrate produced by the non-naturally occurring microbial organisms of the invention have a number of therapeutic and nutritional uses. For example the compound of the invention may be used to reduce the level of free fatty acids circulating in the plasma of a subject. As such it may be used to treat a condition which is caused by, exacerbated by or associated with elevated plasma levels of free fatty acids in a human or animal subject. A subject may therefore be treated by a method which comprises the administration thereto of a compound of the invention as defined herein. The disease, disorder or condition of the subject can thereby be improved or ameliorated.

Diseases, disorder or conditions which are caused by, exacerbated by or associated with elevated plasma levels of free fatty acids include, but are not limited to, neurodegenerative diseases or disorders, for instance Alzheimer's disease, Parkinson's disease, Huntington's chorea; hypoxic states, for instance angina pectoris, extreme physical exertion, intermittent claudication, hypoxia, stroke and myocardial infarction; insulin resistant states, for instance infection, stress, obesity, diabetes and heart failure; and inflammatory states including infection and autoimmune disease.

In addition to reducing plasma levels of fatty acids, the (3R)-hydroxybutyl (3R)-hydroxybutyrate produced by the non-naturally occurring microbial organisms of the invention can act on the appetite centers of the brain. For example, the (3R)-hydroxybutyl (3R)-hydroxybutyrate of the invention can increase the levels of various anorexigenic neuropeptides and metabolites associated with decreased appetite and food intake. Therefore further provided herein are methods for treating a condition where weight loss or weight gain is implicated. For example, the compound may be used in suppressing appetite, treating obesity, promoting weight loss, maintaining a healthy weight or decreasing the ratio of fat to lean muscle in a subject. The subject in each case may be a healthy subject or a compromised subject. A healthy subject may be, for instance, an individual of healthy weight for whom physical performance and/or physical appearance is important. A compromised subject may be an individual of non-healthy weight, for instance an individual who is overweight, clinically obese or clinically very obese. A compromised subject may alternatively be an individual of healthy or non-healthy weight who is suffering from a clinical condition, for instance a condition described herein.

In addition to reducing plasma levels of fatty acids and acting on the appetite centre in the brain, the (3R)-hydroxybutyl (3R)-hydroxybutyrate produced by the non-naturally occurring microbial organisms of the invention can increase brain metabolic efficiency, thereby (a) promoting alertness and improved cognitive function, and (b) inhibiting neurodegeneration. Provided herein is a compound as defined in this application for use in promoting alertness or improving cognitive function, or in treating cognitive dysfunction.

In certain embodiments, provided herein is a non-naturally occurring microbial organism having a (3R)-hydroxybutyl (3R)-hydroxybutyrate pathway. In certain embodiments, the organism comprises at least one exogenous nucleic acid encoding a (3R)-hydroxybutyl (3R)-hydroxybutyrate pathway enzyme expressed in a sufficient amount to produce (3R)-hydroxybutyl (3R)-hydroxybutyrate, wherein said (3R)-hydroxybutyl (3R)-hydroxybutyrate pathway comprises a pathway selected from: (1) 1A; (2) 1B; (3) 1C and 1E; (4) 1D and 1E; (5) 1F; and (6) 1G and 1E, wherein 1A is a (3R)-hydroxybutyl (3R)-hydroxybutyrate ester forming enzyme, wherein 1B is a (3R)-hydroxybutyryl-CoA:(R)-1,3-butanediol alcohol transferase, wherein 1C is a (3R)-hydroxybutyl 3-oxobutyrate ester forming enzyme, wherein 1D is an acetoacetyl-CoA:(R)-1,3-butanediol alcohol transferase, wherein 1E is a (3R)-hydroxybutyl 3-oxobutyrate reductase, wherein 1F is a (3R)-hydroxybutyryl-ACP:(R)-1,3-butanediol ester synthase, wherein 1G is an acetoacetyl-ACP:(R)-1,3-butanediol ester synthase.

In one embodiment, the (3R)-hydroxybutyl (3R)-hydroxybutyrate pathway comprises (1) 1A. In one embodiment, the (3R)-hydroxybutyl (3R)-hydroxybutyrate pathway comprises (2) 1B. In one embodiment, the (3R)-hydroxybutyl (3R)-hydroxybutyrate pathway comprises (3) 1C and 1E. In one embodiment, the (3R)-hydroxybutyl (3R)-hydroxybutyrate pathway comprises (4) 1D and 1E. In one embodiment, the (3R)-hydroxybutyl (3R)-hydroxybutyrate pathway comprises (5) 1F. In one embodiment, the (3R)-hydroxybutyl (3R)-hydroxybutyrate pathway comprises (6) 1G and 1E.

In one aspect, the microbial organism includes one or two exogenous nucleic acids each encoding a (3R)-hydroxybutyl (3R)-hydroxybutyrate pathway enzyme. In another aspect, the microbial organism includes exogenous nucleic acids encoding each of the enzymes of at least one of the (3R)-hydroxybutyl (3R)-hydroxybutyrate pathways selected from (1)-(6) above.

In certain embodiments, a microbial organism having one or more of the (3R)-hydroxybutyl (3R)-hydroxybutyrate pathways described herein further comprises an (R)-1,3-butanediol pathway. In certain embodiments, the organism comprises at least one exogenous nucleic acid encoding an (R)-1,3-butanediol pathway enzyme expressed in a sufficient amount to produce (R)-1,3-butanediol, wherein said (R)-1,3-butanediol pathway comprises a pathway selected from: (1) 2B, 2C, and 2D; (2) 2B, 2H, 2I, and 2D; (3) 2J, 2K, 2C, and 2D; (4) 2J, 2K, 2H, 2I, and 2D; (5) 2A, 2B, 2C, and 2D; (6) 2A, 2B, 2H, 2I, and 2D; (7) 2A, 2J, 2K, 2C, and 2D; (8) 2A, 2J, 2K, 2H, 2I, and 2D; (9) 2E, 2F, 2B, 2C, and 2D; (10) 2E, 2F, 2B, 2H, 2I, and 2D; (11) 2E, 2F, 2J, 2K, 2C, and 2D; (12) 2E, 2F, 2J, 2K, 2H, 2I, and 2D; (13) 3A, 3B, and 3E; (14) 3A, 3C, 2B, 2C, and 2D; (15) 3A, 3C, 2B, 2H, 2I, and 2D; (16) 3A, 3C, 2J, 2K, 2C, and 2D; (17) 3A, 3C, 2J, 2K, 2H, 2I, and 2D; (18) 3A, 3B, 3D, 2C, and 2D; (19) 3A, 3B, 3D, 2H, 2I, and 2D; (20) 3A, 3B, 3G, 2I, and 2D; and (21) 3A, 3B, 3F, and 2D, wherein 2A is an acetoacetyl-CoA thiolase, wherein 2B is a (3R)-hydroxybutyryl-CoA dehydrogenase, wherein 2C is a (3R)-hydroxybutyryl-CoA reductase, wherein 2D is a (3R)-hydroxybutyraldehyde reductase, wherein 2E is an acetyl-CoA carboxylase, wherein 2F is an acetoacetyl-CoA synthase, wherein 2H is a (3R)-hydroxybutyryl-CoA transferase, a (3R)-hydroxybutyryl-CoA synthetase, or a (3R)-hydroxybutyryl-CoA hydrolase, wherein 2I is a (3R)-hydroxybutyraldehyde dehydrogenase, (3R)-hydroxybutyraldehyde oxidase or (3R)-hydroxybutyrate reductase, wherein 2J is a (3S)-hydroxybutyryl-CoA dehydrogenase, wherein 2K is a 3-hydroxybutyryl-CoA epimerase, wherein 3A is a 3-ketoacyl-ACP synthase, wherein 3B is an acetoacetyl-ACP reductase, wherein 3C is an acetoacetyl-CoA:ACP transferase, wherein 3D is a (3R)-hydroxybutyryl-CoA:ACP transferase, wherein 3E is a (3R)-hydroxybutyryl-ACP reductase (alcohol forming), wherein 3F is a (3R)-hydroxybutyryl-ACP reductase (aldehyde forming), wherein 3G is a (3R)-hydroxybutyryl-ACP thioesterase.

In one embodiment, the (R)-1,3-butanediol pathway comprises (1) 2B, 2C, and 2D. In one embodiment, the (R)-1,3-butanediol pathway comprises (2) 2B, 2H, 2I, and 2D. In one embodiment, the (R)-1,3-butanediol pathway comprises (3) 2J, 2K, 2C, and 2D. In one embodiment, the (R)-1,3-butanediol pathway comprises (4) 2J, 2K, 2H, 2I, and 2D. In one embodiment, the (R)-1,3-butanediol pathway comprises (5) 2A, 2B, 2C, and 2D. In one embodiment, the (R)-1,3-butanediol pathway comprises (6) 2A, 2B, 2H, 2I, and 2D. In one embodiment, the (R)-1,3-butanediol pathway comprises (7) 2A, 2J, 2K, 2C, and 2D. In one embodiment, the (R)-1,3-butanediol pathway comprises (8) 2A, 2J, 2K, 2H, 2I, and 2D. In one embodiment, the (R)-1,3-butanediol pathway comprises (9) 2E, 2F, 2B, 2C, and 2D. In one embodiment, the (R)-1,3-butanediol pathway comprises (10) 2E, 2F, 2B, 2H, 2I, and 2D. In one embodiment, the (R)-1,3-butanediol pathway comprises (11) 2E, 2F, 2J, 2K, 2C, and 2D. In one embodiment, the (R)-1,3-butanediol pathway comprises (12) 2E, 2F, 2J, 2K, 2H, 2I, and 2D. In one embodiment, the (R)-1,3-butanediol pathway comprises (13) 3A, 3B, and 3E. In one embodiment, the (R)-1,3-butanediol pathway comprises (14) 3A, 3C, 2B, 2C, and 2D. In one embodiment, the (R)-1,3-butanediol pathway comprises (15) 3A, 3C, 2B, 2H, 2I, and 2D. In one embodiment, the (R)-1,3-butanediol pathway comprises (16) 3A, 3C, 2J, 2K, 2C, and 2D. In one embodiment, the (R)-1,3-butanediol pathway comprises (17) 3A, 3C, 2J, 2K, 2H, 2I, and 2D. In one embodiment, the (R)-1,3-butanediol pathway comprises (18) 3A, 3B, 3D, 2C, and 2D. In one embodiment, the (R)-1,3-butanediol pathway comprises (19) 3A, 3B, 3D, 2H, 2I, and 2D. In one embodiment, the (R)-1,3-butanediol pathway comprises (20) 3A, 3B, 3G, 2I, and 2D. In one embodiment, the (R)-1,3-butanediol pathway comprises and (21) 3A, 3B, 3F, and 2D.

In certain embodiments, a microbial organism having said (3R)-hydroxybutyl (3R)-hydroxybutyrate pathway (1) described herein further comprises a (3R)-hydroxybutyrate pathway. In certain embodiments, the organism comprises at least one exogenous nucleic acid encoding a (3R)-hydroxybutyrate pathway enzyme expressed in a sufficient amount to produce (3R)-hydroxybutyrate, wherein said (3R)-hydroxybutyrate pathway comprises a pathway selected from: (1) 2B, 2C, and 2I; (2) 2B, and 2H; (3) 2J, 2K, 2C, and 2I; (4) 2J, 2K, and 2H; (5) 2A, 2B, 2C, and 2I; (6) 2A, 2B, and 2H; (7) 2A, 2J, 2K, 2C, and 2I; (8) 2A, 2J, 2K, and 2H; (9) 2E, 2F, 2B, 2C, and 2I; (10) 2E, 2F, 2B, and 2H; (11) 2E, 2F, 2J, 2K, 2C, and 2I; (12) 2E, 2F, 2J, 2K, and 2H; (13) 3A, 3B, and 3G; (14) 3A, 3C, 2B, and 2H; (15) 3A, 3C, 2B, 2C, and 2I; (16) 3A, 3C, 2J, 2K, and 2H; and (17) 3A, 3C, 2J, 2K, 2C, and 2I, wherein 2A is an acetoacetyl-CoA thiolase, wherein 2B is a (3R)-hydroxybutyryl-CoA dehydrogenase, wherein 2C is a (3R)-hydroxybutyryl-CoA reductase, wherein 2E is an acetyl-CoA carboxylase, wherein 2F is an acetoacetyl-CoA synthase, wherein 2G is an acetoacetyl-CoA transferase, an acetoacetyl-CoA synthetase or an acetoacetyl-CoA hydrolase, wherein 2H is a (3R)-hydroxybutyryl-CoA transferase, a (3R)-hydroxybutyryl-CoA synthetase, or a (3R)-hydroxybutyryl-CoA hydrolase, wherein 2I is a (3R)-hydroxybutyraldehyde dehydrogenase, a (3R)-hydroxybutyraldehyde oxidase or a (3R)-hydroxybutyrate reductase, wherein 2J is a (3S)-hydroxybutyryl-CoA dehydrogenase, wherein 2K is a 3-hydroxybutyryl-CoA epimerase, wherein 3A is a 3-ketoacyl-ACP synthase, wherein 3B is an acetoacetyl-ACP reductase, wherein 3C is an acetoacetyl-CoA:ACP transferase, wherein 3G is an (3R)-hydroxybutyryl-ACP thioesterase.

In one embodiment, the (3R)-hydroxybutyrate pathway comprises (1) 2B, 2C, and 2I. In one embodiment, the (3R)-hydroxybutyrate pathway comprises (2) 2B, and 2H. In one embodiment, the (3R)-hydroxybutyrate pathway comprises (3) 2J, 2K, 2C, and 2I. In one embodiment, the (3R)-hydroxybutyrate pathway comprises (4) 2J, 2K, and 2H. In one embodiment, the (3R)-hydroxybutyrate pathway comprises (5) 2A, 2B, 2C, and 2I. In one embodiment, the (3R)-hydroxybutyrate pathway comprises (6) 2A, 2B, and 2H. In one embodiment, the (3R)-hydroxybutyrate pathway comprises (7) 2A, 2J, 2K, 2C, and 2I. In one embodiment, the (3R)-hydroxybutyrate pathway comprises (8) 2A, 2J, 2K, and 2H. In one embodiment, the (3R)-hydroxybutyrate pathway comprises (9) 2E, 2F, 2B, 2C, and 2I. In one embodiment, the (3R)-hydroxybutyrate pathway comprises (10) 2E, 2F, 2B, and 2H. In one embodiment, the (3R)-hydroxybutyrate pathway comprises (11) 2E, 2F, 2J, 2K, 2C, and 2I. In one embodiment, the (3R)-hydroxybutyrate pathway comprises (12) 2E, 2F, 2J, 2K, and 2H. In one embodiment, the (3R)-hydroxybutyrate pathway comprises (13) 3A, 3B, and 3G. In one embodiment, the (3R)-hydroxybutyrate pathway comprises (14) 3A, 3C, 2B, and 2H. In one embodiment, the (3R)-hydroxybutyrate pathway comprises (15) 3A, 3C, 2B, 2C, and 2I. In one embodiment, the (3R)-hydroxybutyrate pathway comprises (16) 3A, 3C, 2J, 2K, and 2H. In one embodiment, the (3R)-hydroxybutyrate pathway comprises (17) 3A, 3C, 2J, 2K, 2C, and 2I.

In certain embodiments, a microbial organism having said (3R)-hydroxybutyl (3R)-hydroxybutyrate pathway (2) described herein further comprises a (3R)-hydroxybutyryl-CoA pathway. In certain embodiments, the organism comprises at least one exogenous nucleic acid encoding a (3R)-hydroxybutyryl-CoA pathway enzyme expressed in a sufficient amount to produce (3R)-hydroxybutyryl-CoA, wherein said (3R)-hydroxybutyryl-CoA pathway comprises a pathway selected from: (1) 2B; (2) 2J and 2K; (3) 2A and 2B; (4) 2A, 2J, and 2K; (5) 2E, 2F, and 2B; (6) 2E, 2F, 2J, and 2K; (7) 3A, 3B, and 3D; (8) 3A, 3C, and 2B; and (9) 3A, 3C, 2J, and 2K, wherein 2A is an acetoacetyl-CoA thiolase, wherein 2B is a (3R)-hydroxybutyryl-CoA dehydrogenase, wherein 2E is an acetyl-CoA carboxylase, wherein 2F is an acetoacetyl-CoA synthase, wherein 2G is an acetoacetyl-CoA transferase, an acetoacetyl-CoA synthetase or an acetoacetyl-CoA hydrolase, wherein 2J is a (3S)-hydroxybutyryl-CoA dehydrogenase, wherein 2K is a 3-hydroxybutyryl-CoA epimerase, wherein 3A is 3-ketoacyl-ACP synthase, wherein 3B is an acetoacetyl-ACP reductase, wherein 3C is an acetoacetyl-CoA:ACP transferase, wherein 3D is a (3R)-hydroxybutyryl-CoA:ACP transferase.

In one embodiment, the (3R)-hydroxybutyryl-CoA pathway comprises (1) 2B. In one embodiment, the (3R)-hydroxybutyryl-CoA pathway comprises (2) 2J and 2K. In one embodiment, the (3R)-hydroxybutyryl-CoA pathway comprises (3) 2A and 2B. In one embodiment, the (3R)-hydroxybutyryl-CoA pathway comprises (4) 2A, 2J, and 2K. In one embodiment, the (3R)-hydroxybutyryl-CoA pathway comprises (5) 2E, 2F, and 2B. In one embodiment, the (3R)-hydroxybutyryl-CoA pathway comprises (6) 2E, 2F, 2J, and 2K. In one embodiment, the (3R)-hydroxybutyryl-CoA pathway comprises (7) 3A, 3B, and 3D. In one embodiment, the (3R)-hydroxybutyryl-CoA pathway comprises (8) 3A, 3C, and 2B. In one embodiment, the (3R)-hydroxybutyryl-CoA pathway comprises (9) 3A, 3C, 2J, and 2K.

In certain embodiments, a microbial organism having said (3R)-hydroxybutyl (3R)-hydroxybutyrate pathway (3) described herein further comprises an acetoacetate pathway. In certain embodiments, the organism comprises at least one exogenous nucleic acid encoding an acetoacetate pathway enzyme expressed in a sufficient amount to produce acetoacetate, wherein said acetoacetate pathway comprises a pathway selected from: (1) 2A and 2G; (2) 2E, 2F, and 2G; and (3) 3A, 3C, and 2G, wherein 2A is an acetoacetyl-CoA thiolase, wherein 2E is an acetyl-CoA carboxylase, wherein 2F is an acetoacetyl-CoA synthase, wherein 2G is an acetoacetyl-CoA transferase, an acetoacetyl-CoA synthetase or an acetoacetyl-CoA hydrolase, wherein 3A is an 3-ketoacyl-ACP synthase, wherein 3C is an acetoacetyl-CoA:ACP transferase.

In one embodiment, the acetoacetate pathway comprises (1) 2A and 2G. In one embodiment, the acetoacetate pathway comprises (2) 2E, 2F, and 2G. In one embodiment, the acetoacetate pathway comprises (3) 3A, 3C, and 2G.

In certain embodiments, a microbial organism having said (3R)-hydroxybutyl (3R)-hydroxybutyrate pathway (4) described herein further comprises an acetoacetyl-CoA pathway. In certain embodiments, the organism comprises at least one exogenous nucleic acid encoding an acetoacetyl-CoA pathway enzyme expressed in a sufficient amount to produce acetoacetyl-CoA, wherein said acetoacetyl-CoA pathway comprises a pathway selected from: (1) 2A; (2) 2E and 2F; and (3) 3A and 3C, wherein 2A is an acetoacetyl-CoA thiolase, wherein 2E is an acetyl-CoA carboxylase, wherein 2F is an acetoacetyl-CoA synthase, wherein 3A is a 3-ketoacyl-ACP synthase, wherein 3C is an acetoacetyl-CoA:ACP transferase.

In one embodiment, the acetoacetyl-CoA pathway comprises (1) 2A. In one embodiment, the acetoacetyl-CoA pathway comprises (2) 2E and 2F. In one embodiment, the acetoacetyl-CoA pathway comprises (3) 3A and 3C.

In certain embodiments, a microbial organism having said (3R)-hydroxybutyl (3R)-hydroxybutyrate pathway (5) described herein further comprises a (3R)-hydroxybutyl-ACP pathway. In certain embodiments, the organism comprises at least one exogenous nucleic acid encoding a (3R)-hydroxybutyl-ACP pathway enzyme expressed in a sufficient amount to produce (3R)-hydroxybutyl-ACP, wherein said (3R)-hydroxybutyl-ACP pathway comprises 3A and 3B, wherein 3A is a 3-ketoacyl-ACP synthase, wherein 3B is an acetoacetyl-ACP reductase.

In certain embodiments, a microbial organism having said (3R)-hydroxybutyl (3R)-hydroxybutyrate pathway (6) described herein further comprises an acetoacetyl-ACP pathway. In certain embodiments, the organism comprises at least one exogenous nucleic acid encoding an acetoacetyl-ACP pathway enzyme expressed in a sufficient amount to produce acetoacetyl-ACP, wherein said acetoacetyl-ACP pathway comprises 3A, wherein 3A is a 3-ketoacyl-ACP synthase.

In an additional embodiment, a non-naturally occurring microbial organism is provided having a (3R)-hydroxybutyl (3R)-hydroxybutyrate pathway, wherein the non-naturally occurring microbial organism comprises at least one exogenous nucleic acid encoding an enzyme or protein that converts a substrate to a product selected from the group consisting of (R)-1,3-butanediol and (3R)-hydroxybutyrate to (3R)-hydroxybutyl (3R)-hydroxybutyrate, (R)-1,3-butanediol and (3R)-hydroxybutyryl-CoA to (3R)-hydroxybutyl (3R)-hydroxybutyrate, (R)-1,3-butanediol and (3R)-hydroxybutyl-ACP to (3R)-hydroxybutyl (3R)-hydroxybutyrate, (R)-1,3-butanediol and acetoacetate to (3R)-hydroxybutyl 3-oxobutyrate, (R)-1,3-butanediol and acetoacetyl-CoA to (3R)-hydroxybutyl 3-oxobutyrate, (R)-

1,3-butanediol and acetoacetyl-ACP to (3R)-hydroxybutyl 3-oxobutyrate, (3R)-hydroxybutyl 3-oxobutyrate to (3R)-hydroxybutyl (3R)-hydroxybutyrate, acetyl-CoA to malonyl-CoA, malonyl-CoA to acetoacetyl-CoA, acetyl-CoA to acetoacetyl-CoA, acetoacetyl-CoA to acetoacetate, acetoacetyl-CoA to (3S)-hydroxybutyryl-CoA, (3S)-hydroxybutyryl-CoA to (3R)-hydroxybutyryl-CoA, (3R)-hydroxybutyryl-CoA to (3R)-hydroxybutyrate, (3R)-hydroxybutyryl-CoA to (3R)-hydroxybutyraldehyde, (3R)-hydroxybutyrate to (3R)-hydroxybutyraldehyde, (3R)-hydroxybutyraldehyde to (R)-1,3-butanediol, malonyl-ACP to acetoacetyl-ACP, acetoacetyl-ACP to acetoacetyl-CoA, acetoacetyl-ACP to (3R)-hydroxybutyryl-ACP, (3R)-hydroxybutyryl-ACP to (3R)-hydroxybutyryl-CoA, (3R)-hydroxybutyryl-ACP to (3R)-hydroxybutyrate, (3R)-hydroxybutyryl-ACP to (3R)-hydroxybutyraldehyde, and (3R)-hydroxybutyryl-ACP to (R)-1,3-butanediol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a (3R)-hydroxybutyl (3R)-hydroxybutyrate pathway, such as that shown in FIGS. 1-3.

While generally described herein as a microbial organism that contains a (3R)-hydroxybutyl (3R)-hydroxybutyrate pathway, it is understood that the invention additionally provides a non-naturally occurring microbial organism comprising at least one exogenous nucleic acid encoding a (3R)-hydroxybutyl (3R)-hydroxybutyrate pathway enzyme [or protein if non-enzyme]expressed in a sufficient amount to produce an intermediate of a (3R)-hydroxybutyl (3R)-hydroxybutyrate pathway. For example, as disclosed herein, a (3R)-hydroxybutyl (3R)-hydroxybutyrate pathway is exemplified in FIGS. 1-3. Therefore, in addition to a microbial organism containing a (3R)-hydroxybutyl (3R)-hydroxybutyrate pathway that produces (3R)-hydroxybutyl (3R)-hydroxybutyrate, the invention additionally provides a non-naturally occurring microbial organism comprising at least one exogenous nucleic acid encoding a (3R)-hydroxybutyl (3R)-hydroxybutyrate pathway enzyme, where the microbial organism produces a (3R)-hydroxybutyl (3R)-hydroxybutyrate pathway intermediate, for example, (R)-1,3-butanediol, (3R)-hydroxybutyrate, (3R)-hydroxybutyryl-CoA, (3R)-hydroxybutyl-ACP, acetoacetate, acetoacetyl-CoA, (3R)-hydroxybutyl 3-oxobutyrate, malonyl-CoA, (3S)-hydroxybutyryl-CoA, (3R)-hydroxybutyraldehyde, acetoacetyl-ACP, or (3R)-hydroxybutyryl-ACP.

Figure 2:
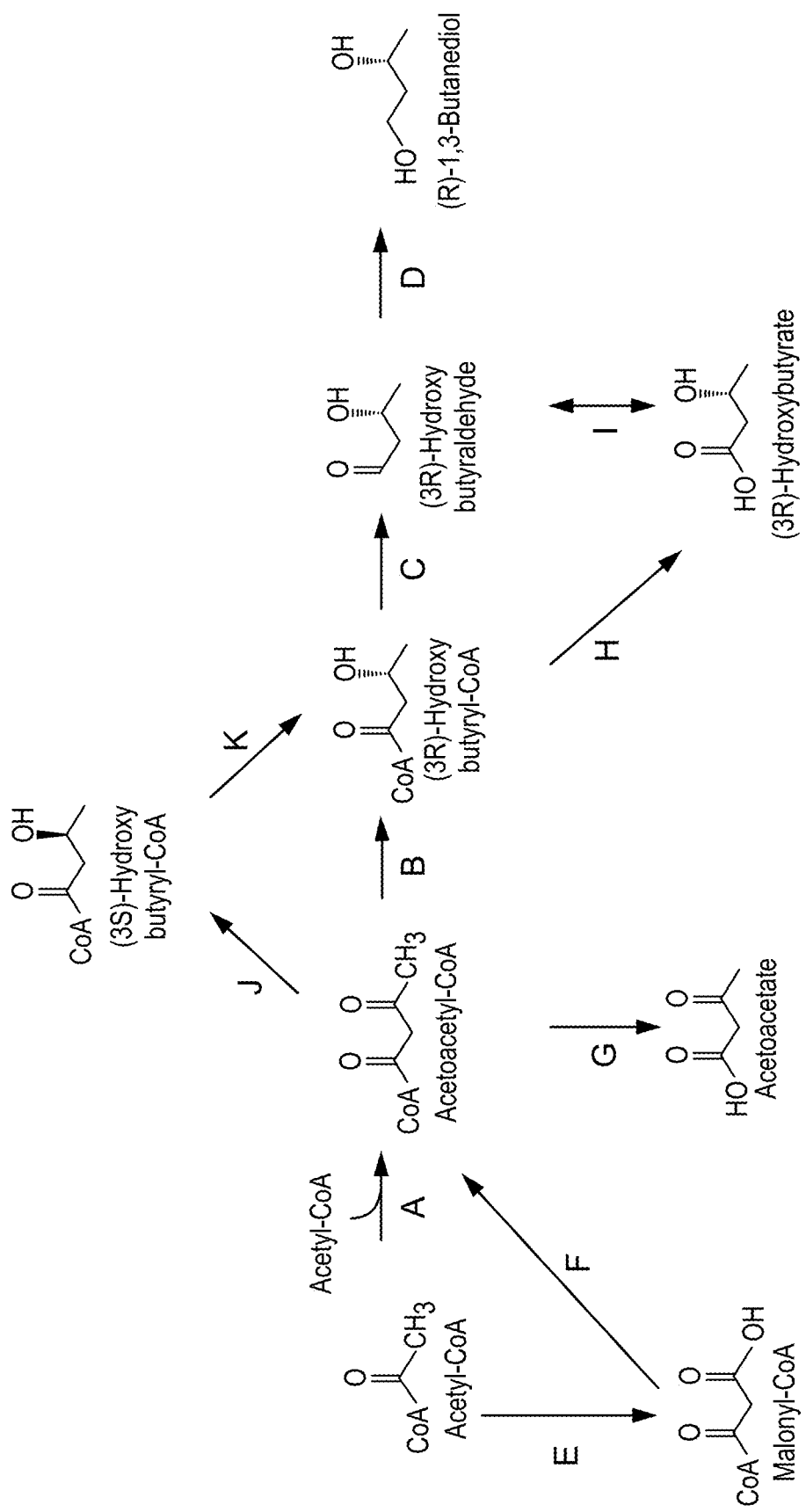
FIG. 2 shows exemplary pathways for the production of (3R)-hydroxybutyl (3R)-hydroxybutyrate precursors (R)-1,3-butanediol, (3R)-hydroxybutyrate, (3R)-hydroxybutyryl-CoA, acetoacetyl-CoA and acetoacetate. Enzymes are: A. acetoacetyl-CoA thiolase, B. (3R)-hydroxybutyryl-CoA dehydrogenase, C. (3R)-hydroxybutyryl-CoA reductase, D. (3R)-hydroxybutyraldehyde reductase, E. acetyl-CoA carboxylase, F. acetoacetyl-CoA synthase, G. acetoacetyl-CoA transferase, synthetase or hydrolase, H. (3R)-hydroxybutyryl-CoA transferase, synthetase, or hydrolase, I. (3R)-hydroxybutyraldehyde dehydrogenase, (3R)-hydroxybutyraldehyde oxidase or (3R)-hydroxybutyrate reductase, J. (3S)-hydroxybutyryl-CoA dehydrogenase and K. 3-hydroxybutyryl-CoA epimerase.
Figure 3:
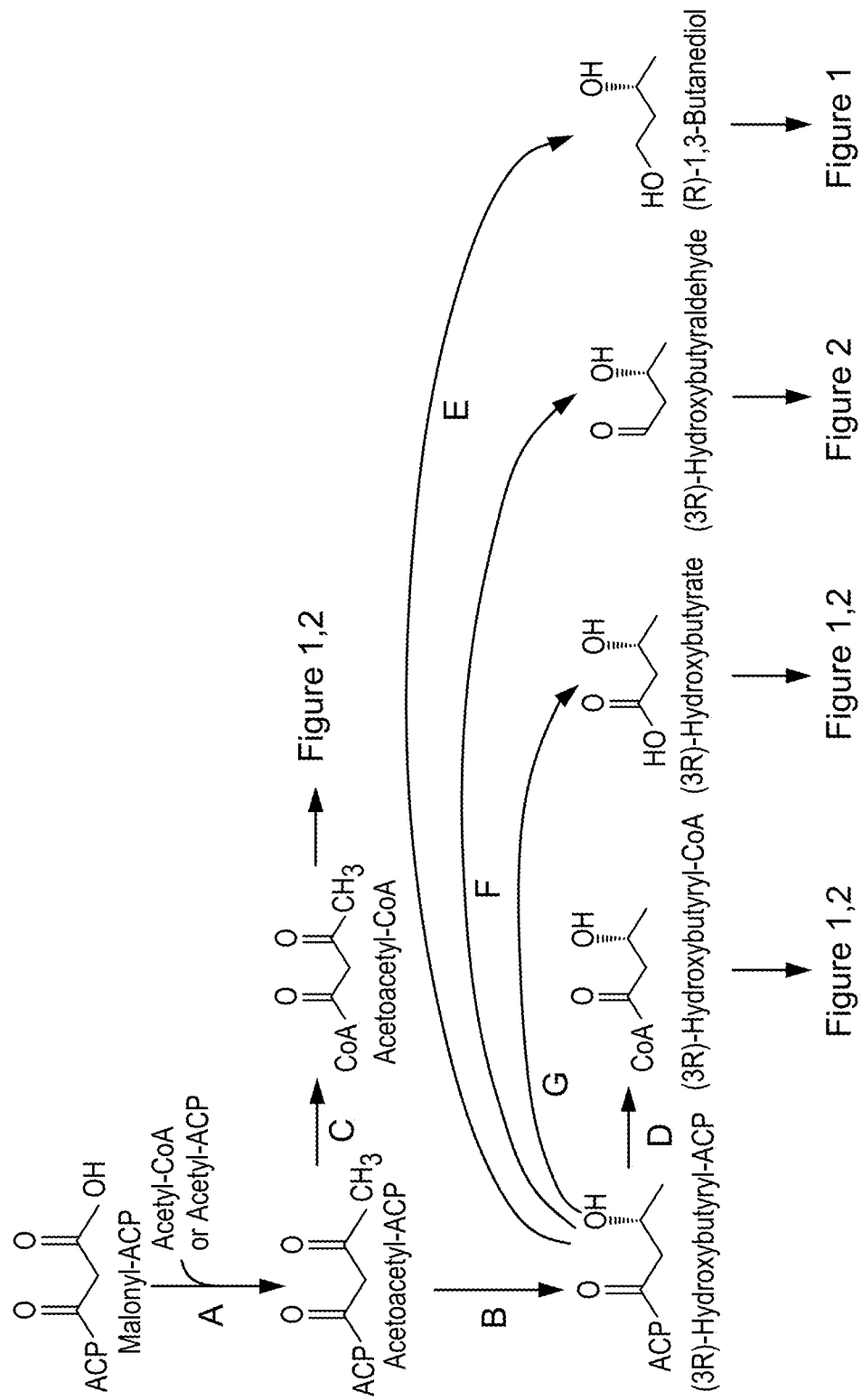
FIG. 3 shows exemplary pathways for formation of acetoacetyl-ACP, acetoacetyl-CoA, (3R)-hydroxybutyryl- CoA, (3R)-hydroxybutyryl-ACP, (3R)-hydroxybutyrate, (3R)-hydroxybutyraldehyde and (R)-1,3-butanediol. Enzymes are: A. 3-ketoacyl-ACP synthase, B. acetoacetyl-ACP reductase, C. acetoacetyl-CoA:ACP transferase, D. (3R)-hydroxybutyryl-CoA:ACP transferase, E. (3R)-hydroxybutyryl-ACP reductase (alcohol forming), F. (3R)-hydroxybutyryl-ACP reductase (aldehyde forming), G. (3R)-hydroxybutyryl-ACP thioesterase. ACP is acyl carrier protein.

It is understood that any of the pathways disclosed herein, as described in the Examples and exemplified in the Figures, including the pathways of FIGS. 1-3, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a (3R)-hydroxybutyl (3R)-hydroxybutyrate pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the product (3R)-hydroxybutyl (3R)-hydroxybutyrate and intermediates acetoacetate and (3R)-hydroxybutyrate, are carboxylic acids, which can occur in various ionized forms, including fully protonated, partially protonated, and fully deprotonated forms.

Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl (3R)-hydroxybutyl (3R)-hydroxybutyrate, ethyl (3R)-hydroxybutyl (3R)-hydroxybutyrate, and n-propyl (3R)-hydroxybutyl (3R)-hydroxybutyrate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more (3R)-hydroxybutyl (3R)-hydroxybutyrate biosynthetic pathways. Depending on the host microbial organism chosen for biosynthesis, nucleic acids for some or all of a particular (3R)-hydroxybutyl (3R)-hydroxybutyrate biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve (3R)-hydroxybutyl (3R)-hydroxybutyrate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as (3R)-hydroxybutyl (3R)-hydroxybutyrate.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida.*

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica,* and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the (3R)-hydroxybutyl (3R)-hydroxybutyrate biosynthetic pathway constituents of a selected host microbial organism, the non-naturally occurring microbial organisms of the invention will include at least one exogenously expressed (3R)-hydroxybutyl (3R)-hydroxybutyrate pathway-encoding nucleic acid and up to all encoding nucleic acids for one or more (3R)-hydroxybutyl (3R)-hydroxybutyrate biosynthetic pathways. For example, (3R)-hydroxybutyl (3R)-hydroxybutyrate biosynthesis can be established in a host deficient in a pathway enzyme or protein through exogenous expression of the corresponding encoding nucleic acid. In a host deficient in all enzymes or proteins of a (3R)-hydroxybutyl (3R)-hydroxybutyrate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of (3R)-hydroxybutyl (3R)-hydroxybutyrate can be included, such as a (3R)-hydroxybutyl (3R)-hydroxybutyrate ester forming enzyme, a (3R)-hydroxybutyryl-CoA dehydrogenase, a (3R)-hydroxybutyryl-CoA reductase, a (3R)-hydroxybutyraldehyde reductase, a (3R)-hydroxybutyraldehyde dehydrogenase, a 3-ketoacyl-ACP synthase, acetoacetyl-CoA:ACP transferase (FIG. 1, Step A, FIG. 2, Steps B, C and I, and FIG. 3, Steps A and C).

Given the teachings and guidance provided herein, those skilled in the art will understand that the number of encoding nucleic acids to introduce in an expressible form will, at least, parallel the (3R)-hydroxybutyl (3R)-hydroxybutyrate pathway deficiencies of the selected host microbial organism. Therefore, a non-naturally occurring microbial organism of the invention can have one, two, three, four, five, six, seven, eight, nine, ten, up to all nucleic acids encoding the enzymes or proteins constituting a (3R)-hydroxybutyl (3R)-hydroxybutyrate biosynthetic pathway disclosed herein. In some embodiments, the non-naturally occurring microbial organisms also can include other genetic modifications that facilitate or optimize (3R)-hydroxybutyl (3R)-hydroxybutyrate biosynthesis or that confer other useful functions onto the host microbial organism. One such other functionality can include, for example, augmentation of the synthesis of one or more of the (3R)-hydroxybutyl (3R)-hydroxybutyrate pathway precursors such as (R)-1,3-butanediol, (3R)-hydroxybutyrate, (3R)-hydroxybutyryl-CoA, (3R)-hydroxybutyl-ACP, acetoacetate, acetoacetyl-CoA, (3R)-hydroxybutyl 3-oxobutyrate, acetyl-CoA, malonyl-CoA, (3S)-hydroxybutyryl-CoA, (3R)-hydroxybutyraldehyde, malonyl-ACP, acetoacetyl-ACP, or (3R)-hydroxybutyryl-ACP. Generally, a host microbial organism is selected such that it produces the precursor of a (3R)-hydroxybutyl (3R)-hydroxybutyrate pathway, either as a naturally produced molecule or as an engineered product that either provides de novo production of a desired precursor or increased production of a precursor naturally produced by the host microbial organism. For example, acetoacetate, acetoacetyl-CoA, acetoacetyl-ACP, acetyl-CoA, malonyl-CoA, and malonyl-ACP are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a (3R)-hydroxybutyl (3R)-hydroxybutyrate pathway.

In some embodiments, a non-naturally occurring microbial organism of the invention is generated from a host that contains the enzymatic capability to synthesize (3R)-hydroxybutyl (3R)-hydroxybutyrate. In this specific embodiment it can be useful to increase the synthesis or accumulation of a (3R)-hydroxybutyl (3R)-hydroxybutyrate pathway product to, for example, drive (3R)-hydroxybutyl (3R)-hydroxybutyrate pathway reactions toward (3R)-hydroxybutyl (3R)-hydroxybutyrate production. Increased synthesis or accumulation can be accomplished by, for example, overexpression of nucleic acids encoding one or more of the above-described (3R)-hydroxybutyl (3R)-hydroxybutyrate pathway enzymes or proteins. Overexpression of the enzyme or enzymes and/or protein or proteins of the (3R)-hydroxybutyl (3R)-hydroxybutyrate pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing (3R)-hydroxybutyl (3R)-hydroxybutyrate, through overexpression of one, two, three, four, five, six, seven, eight, nine, ten, that is, up to all nucleic acids encoding (3R)-hydroxybutyl (3R)-hydroxybutyrate biosynthetic pathway enzymes or proteins. In addition, a non-naturally occurring organism can be generated by mutagenesis of an endogenous gene that results in an increase in activity of an enzyme in the (3R)-hydroxybutyl (3R)-hydroxybutyrate biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a (3R)-hydroxybutyl (3R)-hydroxybutyrate biosynthetic pathway onto the microbial organism. Alternatively, encoding nucleic acids can be introduced to produce an intermediate microbial organism having the biosynthetic capability to catalyze some of the required reactions to confer (3R)-hydroxybutyl (3R)-hydroxybutyrate biosynthetic capability. For example, a non-naturally occurring microbial organism having a (3R)-hydroxybutyl (3R)-hydroxybutyrate biosynthetic pathway can comprise at least two exogenous nucleic acids encoding desired enzymes or proteins, such as the combination of a (3R)-hydroxybutyl (3R)-hydroxybutyrate ester forming enzyme and a (3R)-hydroxybutyraldehyde reductase, or alternatively a (3R)-hydroxybutyryl-ACP:(R)-1,3-butanediol ester synthase and an acetoacetyl-ACP reductase, or alternatively a (3R)-hydroxybutyl 3-oxobutyrate ester forming enzyme and a (3R)-hydroxybutyl 3-oxobutyrate reductase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, an acetoacetyl-CoA:(R)-1,3-butanediol alcohol transferase, a (3R)-hydroxybutyl 3-oxobutyrate reductase, and an acetoacetyl-CoA thiolase, or alternatively an acetoacetyl-ACP:(R)-1,3-butanediol ester synthase, a (3R)-hydroxybutyl 3-oxobutyrate reductase, and a (3R)-hydroxybutyraldehyde reductase, and so forth, as desired, so long as the combination of enzymes and/or proteins of the desired biosynthetic pathway results in production of the corresponding desired product. Similarly, any combination of four, five, six, seven, eight, nine, ten or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of (3R)-hydroxybutyl (3R)-hydroxybutyrate as described herein, the non-naturally occurring microbial organisms and methods of the invention also can be utilized in various combinations with each other and/or with other microbial organisms and methods well known in the art to achieve product biosynthesis by other routes. For example, one alternative to produce (3R)-hydroxybutyl (3R)-hydroxybutyrate other than use of the (3R)-hydroxybutyl (3R)-hydroxybutyrate producers is through addition of another microbial organism capable of converting a (3R)-hydroxybutyl (3R)-hydroxybutyrate pathway intermediate to (3R)-hydroxybutyl (3R)-hydroxybutyrate. One such procedure includes, for example, the fermentation of a microbial organism that produces a (3R)-hydroxybutyl (3R)-hydroxybutyrate pathway intermediate. The (3R)-hydroxybutyl (3R)-hydroxybutyrate pathway intermediate can then be used as a substrate for a second microbial organism that converts the (3R)-hydroxybutyl (3R)-hydroxybutyrate pathway intermediate to (3R)-hydroxybutyl (3R)-hydroxybutyrate. The (3R)-hydroxybutyl (3R)-hydroxybutyrate pathway intermediate can be added directly to another culture of the second organism or the original culture of the (3R)-hydroxybutyl (3R)-hydroxybutyrate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, (3R)-hydroxybutyl (3R)-hydroxybutyrate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of (3R)-hydroxybutyl (3R)-hydroxybutyrate can be accomplished by constructing a microbial organism that contains biosynthetic pathways for conversion of one pathway intermediate to another pathway intermediate or the product. Alternatively, (3R)-hydroxybutyl (3R)-hydroxybutyrate also can be biosynthetically produced from microbial organisms through co-culture or co-fermentation using two organisms in the same vessel, where the first microbial organism produces a (3R)-hydroxybutyl (3R)-hydroxybutyrate intermediate and the second microbial organism converts the intermediate to (3R)-hydroxybutyl (3R)-hydroxybutyrate.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce (3R)-hydroxybutyl (3R)-hydroxybutyrate.

Sources of encoding nucleic acids for a (3R)-hydroxybutyl (3R)-hydroxybutyrate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acidaminococcus fermentans, Acinetobacter baylyi, Acinetobacter calcoaceticus, Acinetobacter* sp. ADP1, *Acinetobacter* sp. strain M-1, *Alcanivorax borkumensis* SK2, *Anabaena variabilis* ATCC 29413, *Arabidopsis thaliana, Archaeoglobus fulgidus* DSM 4304, *Aspergillus niger, Bacillus anthracis, Bacillus cereus* ATCC 14579, *Bacillus megaterium, Bacillus selenitireducens* MLS10, *Bacillus subtilis, Bos taurus, Brassica napsus,* butyrate-producing bacterium L2-50, *Candida albicans, Candida antarctica, Carthamus tinctorius, Citrobacter koseri* ATCC BAA-895, *Clostridium acetobutylicum, Clostridium beijerinckii, Clostridium kluyveri, Clostridium kluyveri* DSM 555, *Clostridium saccharoperbutylacetonicum, Cucumis sativus, Cuphea hookeriana, Cuphea palustris, Cupriavidus taiwanensis,* Cyanobium PCC7001, *Cyanothece* sp. PCC 7425, *Desulfatibacillum alkenivorans* AK-01, *Dictyostelium discoideum* AX4, *Erythrobacter* sp. NAP1, *Fragaria x ananassa, Fusarium proliferatum, Fusobacterium nucleatum, Geobacillus thermoglucosidasius* M10EXG, *Hahella chejuensis, Haloarcula marismortui* ATCC 43049, *Helicobacter pylori, Homo sapiens, Kluyveromyces lactis, Lactobacillus brevis, Lactobacillus brevis* ATCC 367, *Lactococcus lactis, Leuconostoc mesenteroides, Lyngbya* sp. PCC 8106, marine gamma proteobacterium HTCC2080, *Marinobacter adhaerens* HP15, *Marinobacter algicola* DG893, *Marinobacter aquaeolei, Marinobacter hydrocarbonoclasticus, Marinobacter santoriniensis, Marinobacter* sp. BSs20148, *Marinobacter* sp. ELB 7, *Metallosphaera sedula, Mus musculus, Mycobacterium avium* subsp. paratuberculosis K-10, *Mycobacterium bovis* BCG, *Mycobacterium marinum* M, *Mycobacterium smegmatis* MC2 155, *Mycobacterium tuberculosis, Nocardia farcinica* IFM 10152, *Nocardia iowensis* (sp. NRRL 5646), *Nodularia spumigena* CCY9414, *Nostoc azollae, Nostoc* sp. PCC 7120, *Oceanobacter* sp. RED65, *Ogataea wickerhamii, Oryctolagus cuniculus, Penicillium chrysogenum, Plasmodium falciparum, Porphyromonas gingivalis, Porphyromonas gingivalis* W83, *Prochlorococcus marinus* MIT 9312, *Pseudomonas aeruginosa, Pseudomonasfluorescens, Pseudomonas putida, Pseudomonas* sp, *Pyrobaculum aerophilum* str. IM2, *Ralstonia eutropha, Ralstonia eutropha* H16, *Rattus norvegicus, Rhodobacter sphaeroides, Rhodococcus erythropolis,* Rosa hybrid cultivar, *Roseiflexus castenholzii, Saccharomyces cerevisiae, Saccharomyces cerevisiae* s288c, *Salmonella enterica, Salmonella enterica Typhimurium, Salmonella typhimurium, Schizosaccharomyces pombe, Simmondsia chinensis, Streptomyces avermitillis, Streptomyces griseus* subsp. *griseus* NBRC 13350, *Sulfolobus acidocaldarius, Sulfolobus solfataricus, Sulfolobus tokodaii, Synechococcus elongatus* PCC 6301, *Synechococcus elongatus* PCC7942, *Thermoanaerobacter tengcongensis* MB4, *Thermomyces lanuginosus, Thermus thermophilus, Trichomonas vaginalis* G3, *Trypanosoma brucei, Tsukamurella paurometabola* DSM 20162, *Umbellularia californica, Xanthomonas campestris, Yarrowia lipolytica, Zea mays, Zoogloea ramigera, Zymomonas mobilis,* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite (3R)-hydroxybutyl (3R)-hydroxybutyrate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of (3R)-hydroxybutyl (3R)-hydroxybutyrate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative (3R)-hydroxybutyl (3R)-hydroxybutyrate biosynthetic pathway exists in an unrelated species, (3R)-hydroxybutyl (3R)-hydroxybutyrate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize (3R)-hydroxybutyl (3R)-hydroxybutyrate.

A nucleic acid molecule encoding a (3R)-hydroxybutyl (3R)-hydroxybutyrate pathway enzyme or protein of the invention can also include a nucleic acid molecule that hybridizes to a nucleic acid disclosed herein by GenBank and/or GI number or a nucleic acid molecule that hybridizes to a nucleic acid molecule that encodes an amino acid sequence disclosed herein by GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be disclosed as having a certain percent sequence identity to a nucleic acid disclosed herein by GenBank and/or GI number or a nucleic acid molecule that hybridizes to a nucleic acid molecule that encodes an amino acid sequence described herein by GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity, or be identical, to a nucleic acid described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., Molecular Cloning: A Laboratory Manual, Third Ed. Cold Spring Harbor Laboratory, New York (2001); and Ausubel et al., Current Protocols in Molecular Biology, John Wiley and Sons, Baltimore, Md. (1999).

A nucleic acid molecule encoding a (3R)-hydroxybutyl (3R)-hydroxybutyrate pathway enzyme or protein of the invention can have at least a certain sequence identity to a nucleotide sequence disclosed herein. According, in some aspects of the invention, a nucleic acid molecule encoding a (3R)-hydroxybutyl (3R)-hydroxybutyrate pathway enzyme or protein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity to a nucleic acid described herein by GenBank and/or GI number or a nucleic acid molecule that hybridizes to a nucleic acid molecule that encodes an amino acid sequence described herein by GenBank and/or GI number.

Sequence identity (also known as homology or similarity) refers to sequence similarity between two nucleic acid molecules or between two polypeptides. Identity can be determined by comparing a position in each sequence which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., Current Protocols in Molecular Biology, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

Methods for constructing and testing the expression levels of a non-naturally occurring (3R)-hydroxybutyl (3R)-hydroxybutyrate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of (3R)-hydroxybutyl (3R)-hydroxybutyrate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more (3R)-hydroxybutyl (3R)-hydroxybutyrate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In another embodiment, provided herein is a method for producing (3R)-hydroxybutyl (3R)-hydroxybutyrate comprising culturing the non-naturally occurring microbial organism of having a (3R)-hydroxybutyl (3R)-hydroxybutyrate pathway as described herein under conditions and for a sufficient period of time to produce (3R)-hydroxybutyl (3R)-hydroxybutyrate. In certain embodiments, the microbial organism also has a (R)-1,3-butanediol pathway, a (3R)-hydroxybutyrate pathway, a (3R)-hydroxybutyryl-CoA pathway, an acetoacetate pathway, an acetoacetyl-CoA pathway, a (3R)-hydroxybutyl-ACP pathway, an acetoacetyl-ACP pathway or any combination described herein. In certain embodiments, the microbial organism comprises at least one exogenous nucleic acid encoding a (3R)-hydroxybutyl (3R)-hydroxybutyrate pathway enzyme expressed in a sufficient amount to produce (3R)-hydroxybutyl (3R)-hydroxybutyrate. In certain embodiments, the organism is cultured in a substantially anaerobic culture medium.

In another embodiment, provided herein is a process for producing (3R)-hydroxybutyl (3R)-hydroxybutyrate comprising: (a) culturing a non-naturally occurring microbial organism having an (R)-1,3-butanediol pathway under conditions and for a sufficient period of time to produce (R)-1,3-butanediol in culture medium; (b) culturing a non-naturally occurring microbial organism having a (3R)-hydroxybutyrate pathway under conditions and for a sufficient period of time to produce (3R)-hydroxybutyrate in culture medium; and (c) reacting the (R)-1,3-butanediol produced in step (a) and the (3R)-hydroxybutyrate produced in step (b) with a chemical catalyst or an enzyme to produce (3R)-hydroxybutyl (3R)-hydroxybutyrate. In certain aspects, said enzyme is a (3R)-hydroxybutyl (3R)-hydroxybutyrate ester forming enzyme. In certain aspects, said enzyme is secreted by said non-naturally occurring microbial organism having an (R)-1,3-butanediol pathway or said non-naturally occurring microbial organism having a (3R)-hydroxybutyrate pathway. In still another aspect, said chemical catalyst is a dehydrating agent.

In certain embodiments, the microbial organism used in the process of the invention also has a (R)-1,3-butanediol pathway, a (3R)-hydroxybutyrate pathway or any combination described herein. In certain embodiments, the microbial organism comprises at least one exogenous nucleic acid encoding a (3R)-hydroxybutyl (3R)-hydroxybutyrate pathway enzyme expressed in a sufficient amount to produce (3R)-hydroxybutyl (3R)-hydroxybutyrate. In certain embodiments, the organism is cultured in a substantially anaerobic culture medium.

In certain embodiments, the non-naturally occurring microbial organism having an (R)-1,3-butanediol pathway and said non-naturally occurring microbial organism having a (3R)-hydroxybutyrate pathway are cultured in the same culture medium. In another embodiment, the non-naturally occurring microbial organism having an (R)-1,3-butanediol pathway and said non-naturally occurring microbial organism having a (3R)-hydroxybutyrate pathway are cultured in separate culture medium.

In certain embodiments, the (R)-1,3-butanediol or the (3R)-hydroxybutyrate is at least partially purified prior to step (c) described above. Methods for purifying (R)-1,3-butanediol or (3R)-hydroxybutyrate from the culture medium are well known in the art, and any one of which can be sued in the process of the invention. In certain aspects of the invention process, the pH of the culture medium can be adjusted to favor producing (3R)-hydroxybutyl (3R)-hydroxybutyrate in step (c) described above.

In certain embodiments, the process of the invention can include in step (c) heating a liquid medium comprising said (R)-1,3-butanediol produced in step (a) and/or (3R)-hydroxybutyrate produced in step (b).

In another embodiment, provided herein is a process for producing (3R)-hydroxybutyl (3R)-hydroxybutyrate comprising: (a) culturing a non-naturally occurring microbial organism having an (R)-1,3-butanediol pathway under conditions and for a sufficient period of time to produce (R)-1, 3-butanediol in culture medium; (b) culturing a non-naturally occurring microbial organism having an acetoacetate pathway under conditions and for a sufficient period of time to produce acetoacetate in culture medium; (c) reacting the (R)-1,3-butanediol produced in step (a) and the acetoacetate produced in step (b) with a chemical catalyst or an enzyme to produce (3R) hydroxybutyl 3-oxobutyrate; and (d) reacting said (3R)-hydroxybutyl 3-oxobutyrate with an enzyme to produce (3R) hydroxybutyl (3R)-hydroxybutyrate. In one aspect, said enzyme to produce (3R)-hydroxybutyl (3R)-hydroxybutyrate is a (3R) hydroxybutyl 3-oxobutyrate reductase. In another aspect, said enzyme to produce (3R)-hydroxybutyl 3-oxobutyrate is a (3R) hydroxybutyl 3-oxobutyrate ester forming enzyme. In certain aspects, said enzyme to produce (3R)-hydroxybutyl (3R)-hydroxybutyrate or said enzyme to produce (3R)-hydroxybutyl 3-oxobutyrate is secreted by said non-naturally occurring microbial organism having an (R)-1,3-butanediol pathway or said non-naturally occurring microbial organism having a (3R)-hydroxybutyrate pathway. In still another aspect, said chemical catalyst is a dehydrating agent.

In certain embodiments, the microbial organism used in the process as provided herein has a (R)-1,3-butanediol pathway, an acetoacetate pathway or any combination described herein. In certain embodiments, the microbial organism comprises at least one exogenous nucleic acid encoding a (3R)-hydroxybutyl (3R)-hydroxybutyrate pathway enzyme expressed in a sufficient amount to produce (3R)-hydroxybutyl (3R)-hydroxybutyrate. In certain embodiments, the organism is cultured in a substantially anaerobic culture medium.

In certain embodiments, the non-naturally occurring microbial organism having an (R)-1,3-butanediol pathway and the non-naturally occurring microbial organism having an acetoacetate pathway are cultured in the same culture medium. In certain embodiments, the non-naturally occurring microbial organism having an (R)-1,3-butanediol pathway and the non-naturally occurring microbial organism having an acetoacetate pathway are cultured in separate culture medium.

In certain embodiments, the (R)-1,3-butanediol or said acetoacetate is at least partially purified prior to step (c) described above. Methods for purifying (R)-1,3-butanediol or acetoacetate from the culture medium are well known in the art, and any one of which can be sued in the process of the invention. In certain aspects of the invention process, the pH of said culture medium is adjusted to favor producing (3R)-hydroxybutyl 3-oxobutyrate in step (c).

In certain embodiments, the process of the invention can include in step (c) heating a liquid medium comprising said (R)-1,3-butanediol produced in step (a) and/or acetoacetate produced in step (b).

Suitable purification and/or assays to test for the production of (3R)-hydroxybutyl (3R)-hydroxybutyrate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The (3R)-hydroxybutyl (3R)-hydroxybutyrate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the (3R)-hydroxybutyl (3R)-hydroxybutyrate producers can be cultured for the biosynthetic production of (3R)-hydroxybutyl (3R)-hydroxybutyrate. Accordingly, in some embodiments, the invention provides culture medium having the (3R)-hydroxybutyl (3R)-hydroxybutyrate or (3R)-hydroxybutyl (3R)-hydroxybutyrate pathway intermediate described herein. In some aspects, the culture medium can also be separated from the non-naturally occurring microbial organisms of the invention that produced the (3R)-hydroxybutyl (3R)-hydroxybutyrate or (3R)-hydroxybutyl (3R)-hydroxybutyrate pathway intermediate. Methods for separating a microbial organism from culture medium are well known in the art. Exemplary methods include filtration, flocculation, precipitation, centrifugation, sedimentation, and the like.

For the production of (3R)-hydroxybutyl (3R)-hydroxybutyrate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high (3R)-hydroxybutyl (3R)-hydroxybutyrate yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example: sugars such as glucose, xylose, arabinose, galactose, mannose, fructose, sucrose and starch; or glycerol, including crude glycerol, and it is understood that a carbon source can be used alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of (3R)-hydroxybutyl (3R)-hydroxybutyrate.

In addition to renewable feedstocks such as those exemplified above, the (3R)-hydroxybutyl (3R)-hydroxybutyrate microbial organisms of the invention also can be modified for growth on syngas as its source of carbon. In this specific embodiment, one or more proteins or enzymes are expressed in the (3R)-hydroxybutyl (3R)-hydroxybutyrate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)).

This can be summarized by the following equation:

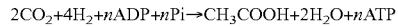

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a (3R)-hydroxybutyl (3R)-hydroxybutyrate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate as described in U.S. Pat. No. 8,048,661 (issued Nov. 1, 2011) and U.S. Publication No. 2012-0329113 (published Dec. 27, 2012), which are herein incorporated by reference. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the (3R)-hydroxybutyl (3R)-hydroxybutyrate precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a (3R)-hydroxybutyl (3R)-hydroxybutyrate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, (3R)-hydroxybutyl (3R)-hydroxybutyrate and any of the intermediate metabolites in the (3R)-hydroxybutyl (3R)-hydroxybutyrate pathway. All that is required is to engineer in one or more of the required enzyme or protein activities to achieve biosynthesis of the desired compound or intermediate including, for example, inclusion of some or all of the (3R)-hydroxybutyl (3R)-hydroxybutyrate biosynthetic pathways. Accordingly, the invention provides a non-naturally occurring microbial organism that produces and/or secretes (3R)-hydroxybutyl (3R)-hydroxybutyrate when grown on a carbohydrate or other carbon source and produces and/or secretes any of the intermediate metabolites shown in the (3R)-hydroxybutyl (3R)-hydroxybutyrate pathway when grown on a carbohydrate or other carbon source. The (3R)-hydroxybutyl (3R)-hydroxybutyrate producing microbial organisms of the invention can initiate synthesis from an intermediate, for example, (R)-1,3-butanediol, (3R)-hydroxybutyrate, (3R)-hydroxybutyryl-CoA, (3R)-hydroxybutyl-ACP, acetoacetate, acetoacetyl-CoA, (3R)-hydroxybutyl 3-oxobutyrate, acetyl-CoA, malonyl-CoA, (3S)-hydroxybutyryl-CoA, (3R)-hydroxybutyraldehyde, malonyl-ACP, acetoacetyl-ACP, or (3R)-hydroxybutyryl-ACP.

The non-naturally occurring microbial organisms of the invention are constructed using methods well known in the art as exemplified herein to exogenously express at least one nucleic acid encoding a (3R)-hydroxybutyl (3R)-hydroxybutyrate pathway enzyme or protein in sufficient amounts to produce (3R)-hydroxybutyl (3R)-hydroxybutyrate. It is understood that the microbial organisms of the invention are cultured under conditions sufficient to produce (3R)-hydroxybutyl (3R)-hydroxybutyrate. Following the teachings and guidance provided herein, the non-naturally occurring microbial organisms of the invention can achieve biosynthesis of (3R)-hydroxybutyl (3R)-hydroxybutyrate resulting in intracellular concentrations between about 0.1-200 mM or more. Generally, the intracellular concentration of (3R)-hydroxybutyl (3R)-hydroxybutyrate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the (3R)-hydroxybutyl (3R)-hydroxybutyrate producers can synthesize (3R)-hydroxybutyl (3R)-hydroxybutyrate at intracellular concentrations of 5-10 mM or more as well as all other concentrations exemplified herein. It is understood that, even though the above description refers to intracellular concentrations, (3R)-hydroxybutyl (3R)-hydroxybutyrate producing microbial organisms can produce (3R)-hydroxybutyl (3R)-hydroxybutyrate intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of (3R)-hydroxybutyl (3R)-hydroxybutyrate can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylsulfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of (3R)-hydroxybutyl (3R)-hydroxybutyrate includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of (3R)-hydroxybutyl (3R)-hydroxybutyrate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of (3R)-hydroxybutyl (3R)-hydroxybutyrate. Generally, and as with non-continuous culture procedures, the continuous and/or near-continuous production of (3R)-hydroxybutyl (3R)-hydroxybutyrate will include culturing a non-naturally occurring (3R)-hydroxybutyl (3R)-hydroxybutyrate producing organism of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of (3R)-hydroxybutyl (3R)-hydroxybutyrate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the (3R)-hydroxybutyl (3R)-hydroxybutyrate producers of the invention for continuous production of substantial quantities of (3R)-hydroxybutyl (3R)-hydroxybutyrate, the (3R)-hydroxybutyl (3R)-hydroxybutyrate producers also can be, for example, simultaneously subjected to chemical synthesis and/or enzymatic procedures to convert the product to other compounds or the product can be separated from the fermentation culture and sequentially subjected to chemical and/or enzymatic conversion to convert the product to other compounds, if desired.

One example of chemical conversion is an esterification reaction. Esterification reactions can be used to react an alcohol with a carboxylic acid to form an ester and water. Esterification reactions can include the use of a catalyst. In certain embodiments, the culture medium containing (3R)-hydroxybutyl (3R)-hydroxybutyrate can include (R)-1,3-butanediol and (R)-3-hydroxybutyric acid. In certain embodiments, the culture medium can be subjected to an esterification reaction in the presence of a catalyst. For example, in the esterification reaction, (R)-1,3-butanediol and (R)-3-hydroxybutyric acid can react in the presence of a catalyst to form (3R)-hydroxybutyl (3R)-hydroxybutyrate and water. In certain embodiments, the catalyst can be an enzyme or an acid catalyst. The enzyme catalyst can be from the culture medium, or can be added to the culture medium prior to, or during, the esterification reaction. The acid catalyst can be a mineral acid, an organic acid or mixtures thereof. The acid catalyst can be added prior to the esterification reaction or added during the esterification reaction. Non-limiting examples of acids can be sulfuric acid, hydrochloric acid, hydrobromic acid, phosphoric acid, trichloroacetic acid, methanesulfonic acid, benzenesulfonic acid, p-toluenesulfonic acid. The esterification reaction can be at ambient temperature, or can be at elevated temperatures from 30° C. to 100° C., 30° C. to 80° C., 30° C. to 60° C., 30° C. to 50° C., 40° C. to 100° C., 40° C. to 80° C., 40° C. to 60° C., 40° C. to 50° C., 50° C. to 100° C. or 50° C. to 80° C. In certain embodiments, the esterification reaction temperature is between about 40° C. to about 90° C.

In certain embodiments, the culture medium subjected to esterification contains (R)-1,3-butanediol and (R)-3-hydroxybutyric acid, each of which is in greater abundance in the culture medium prior to esterification than (3R)-hydroxybutyl (3R)-hydroxybutyrate. In some embodiments, the culture medium subjected to esterification contains (R)-1,3-butanediol and (R)-3-hydroxybutyric acid with negligible (e.g., less than 0.1 mM, less than 0.010 mM, less than 0.001 mM, less than 0.1 micromolar, less than 10 nanomolar or less than 1 nanomolar), or no detectable, (3R)-hydroxybutyl (3R)-hydroxybutyrate. In certain embodiments, the culture medium subjected to esterification is a combination of two culture media, one having (R)-1,3-butanediol and the other (R)-3-hydroxybutyric acid, and which is subjected to an esterification reaction in the presence of a catalyst. It will be understood that, in certain embodiments, the culture medium subjected to an esterification reaction can, for example, be subjected to centrifugation, filtration, salt removal, evaporation, and/or other procedures as described herein, prior to being subjected to esterification.

In certain embodiments, simultaneous or nearly simultaneous with the esterification reaction, the culture medium can be subjected to liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the (3R)-hydroxybutyl (3R)-hydroxybutyrate. For example, as the (3R)-hydroxybutyl (3R)-hydroxybutyrate forms during the esterification reaction, the (3R)-hydroxybutyl (3R)-hydroxybutyrate can be extracted into the organic solvent to help drive the reaction to the ester product, (3R)-hydroxybutyl (3R)-hydroxybutyrate. The product (3R)-hydroxybutyl (3R)-hydroxybutyrate can then be recovered from the organic solvent by methods well known in the art such as, for example, vacuum distillation or stripping (see, e.g., FIG. 4).

Figure 4:
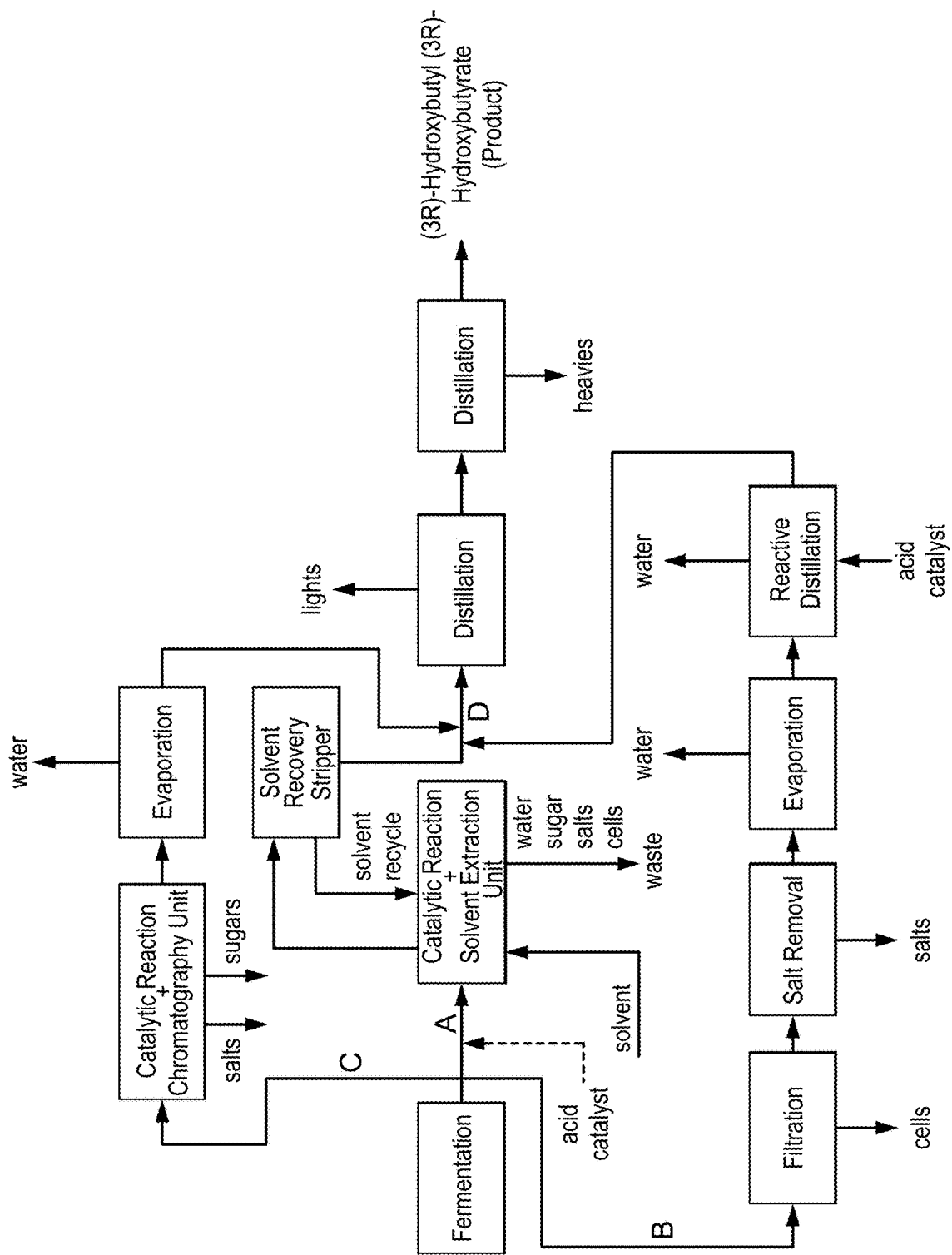
FIG. 4 is a flow diagram depicting alternate schemes labeled "A," "B" and "C" for the production and isolation (3R)-hydroxybutyl (3R)-hydroxybutyrate.

In some embodiments where the culture medium is subjected to liquid-liquid extraction using a water-immiscible organic solvent, the organic solvent ("extractant") is recycled to the liquid-liquid extraction vessel or column to minimize solvent loss (see, e.g., FIG. 4, scheme A).

In certain embodiments, after the esterification reaction, the culture medium can be subjected to liquid-liquid extraction using a water immiscible organic solvent to provide an organic solution of the (3R)-hydroxybutyl (3R)-hydroxybutyrate. In certain embodiments, before the esterification reaction, the culture medium can be subjected to liquid-liquid extraction using a water immiscible organic solvent to provide an organic solution of the (3R)-hydroxybutyl (3R)-hydroxybutyrate.

In certain embodiments, the culture medium can be subjected to the esterification reaction and liquid-liquid extraction one time, two times, three times, four times or more. During each time, the liquid-liquid extraction can be simultaneous or nearly simultaneous with, before or after the esterification reaction.

In certain embodiments, the esterification reaction and simultaneous or nearly simultaneous liquid-liquid extraction occur in a stirred tank reactor. In certain embodiments, the esterification reaction and simultaneous or nearly simultaneous liquid-liquid extraction occur in a continuous extractor. In certain embodiments, the continuous extractor can be operated under countercurrent flow, or can be operated under parallel flow conditions. The extraction operation may be performed continuously or batchwise using any of the following equipment well known in the art, which may be used individually or in any combination: packed column, plate column, mechanically agitated or pulsed column. In certain embodiments, the extraction operation can be performed stagewise in vessels such as mixer-settlers or in centrifugal extractors.

In certain embodiments, the organic solution of the (3R)-hydroxybutyl (3R)-hydroxybutyrate from the liquid-liquid extraction can be subjected to a solvent evaporation step to produce a (3R)-hydroxybutyl (3R)-hydroxybutyrate product and an evaporated solvent, which can be condensed and collected as recovered solvent. In certain embodiments, the solvent evaporation step occurs at elevated temperatures and/or reduced pressures. The temperatures of solvent evaporation step can be from 30° C. to 90° C., 30° C. to 60° C., 30° C. to 50° C., 30° C. to 40° C., 40° C. to 80° C., 40° C. to 70° C., 40° C. to 60° C., 40° C. to 50° C., or 50° C. to 80° C., for example. The pressures of the solvent evaporation step can be less than atmospheric, 500 mmHg, 200 mmHg, 100 mmHg, 50 mmHg, 40 mmHg, 30 mmHg, 20 mmHg, 15 mmHg, 10 mmHg, or 5 mmHg, for example. In certain embodiments, the evaporated solvent from the evaporative solvent step can be collected. In certain embodiments, the recovered solvent from the evaporative solvent step can be recycled and/or reused in the solvent-solvent extraction.

Separation of the impurities from a product into separate liquid solutions can be achieved by chromatography, either batchwise, partially continuous or continuous, including liquid chromatography, gas chromatography, gas-liquid chromatography, and supercritical chromatography. Various forms of chromatography can be used that are known to one of skill in the art, including, for example, those using a fixed-bed solid phase, those using a fluidized-bed solid phase, and those using supercritical fluids. The chromatography procedure separates materials based on a selective interaction with the solid phase. The chromatography procedure can be, for example, adsorption chromatography, size exclusion chromatography, ion exchange chromatography, reversed-phase chromatography, affinity chromatography or expanded bed adsorption. The solid phase can be a resin or can be a porous solid. For example, the solid phase can be silica gel, cellulose, kieselguhr, alumina, polymeric resin made of styrene crosslinked with divinyl benzene (DVB). In certain embodiments, the chromatography procedure can use multiple beds of solid phase that can be arranged in a parallel or serial fashion. In parallel fashion, one bed can be used for the separation while another bed can be reconditioned for reuse. The multiple beds can contain the same solid phase, or can have different solid phases. Flow rates in chromatography can be from 1 bed volume per hour (BV/h) to 50 BV/h, 2 BV/h to 40 BV/h, 2 BV/h to 30 BV/h, 4 BV/h to 40 BV/h, 4 BV/h to 30 BV/h, 4 BV/h to 20 BV/h, 4 BV/h to 10 BV/h or 10 BV/h to 30 BV/h.

In certain embodiments, chromatography, for instance, ion exchange chromatography, can be utilized for both catalyzing the esterification reaction and for separating reaction components. In some embodiments, a strong acid ion exchange resin is used to catalyze the esterification reaction by providing a low pH environment in a chromatography column. Simultaneously, organic acids, waters, sugars and inorganic ions can be separated in the chromatography column on the basis of size and/or charge. Typical resins are made with styrene DVB (polymer) backbones with sulfonated functional groups capable of exchanging H+ ions with the solution. The resins can, for example, be of a microporous or macroporous type. In a continuous ion exchange system, the ester is continuously removed to force the equilibrium to product formation. A subsequent water removal step such as evaporation/distillation to continuously remove the water will also shift the equilibrium towards the acetate product (see, e.g., FIG. 4, scheme C).

Reactive distillation is a procedure that can use a distillation column to remove a product as it forms from a reaction occurring in the distillation column to drive the reaction to products. For some reactive distillation procedures, a catalyst can be present. In certain embodiments, a material subjected to reactive distillation can include an alcohol and a carboxylic acid. For example, in a reactive distillation, an esterification reaction between an alcohol and a carboxylic acid, which can include a catalyst, can occur in the distillation column in the reactive distillation to form an ester and water, and the water from the esterification reaction can be removed by the distillation column as it is formed (see, e.g., FIG. 4, scheme B). In certain embodiments, the water is removed from the top or overhead of the distillation column in the reactive distillation. In certain embodiments, the ester product is removed from the base or bottom of the distillation column in the reactive distillation. In certain embodiments, the amount of unreacted alcohol in material removed from the distillation column in the reactive distillation, can be less than 50%, 40%, 30%, 25%, 20%, 15%, 10%, 9%, 8%, 7%, 6%, 5%, 4%, 3%, 2%, 1% (by weight, volume or moles), of that amount of alcohol that was in the material subjected to a reactive distillation. In certain embodiments, the amount of unreacted carboxylic acid in material removed from the distillation column in the reactive distillation, can be less than 50%, 40%, 30%, 25%, 20%, 15%, 10%, 9%, 8%, 7%, 6%, 5%, 4%, 3%, 2%, 1% (by weight, volume or moles), of that amount of carboxylic acid that was in the material subjected to a reactive distillation.

In certain embodiments, the esterification reaction can be the reaction of (R)-1,3-butanediol with (R)-3-hydroxybutyric acid to form (3R)-hydroxybutyl (3R)-hydroxybutyrate and water, and the water from the esterification reaction can be removed by the distillation column as it is formed. In certain embodiments, the culture medium containing (3R)-hydroxybutyl (3R)-hydroxybutyrate can include (R)-1,3-butanediol and (R)-3-hydroxybutyric acid. In certain embodiments, the culture medium can be subjected to reactive distillation. In certain embodiments, the culture medium that can include (R)-1,3-butanediol and (R)-3-hydroxybutyric acid can be subjected to reactive distillation.

In certain embodiments, a catalyst is added to the reactive distillation. In certain embodiments, the catalyst is added to a feed material in the reactive distillation. In certain embodiments, the catalyst is added to the distillation column in the reactive distillation. For example, the catalyst can be added (or fed) to the distillation column in the reactive distillation at a feed point below, or a feed point above, the feed point of the material that is to be subjected to reactive distillation. In certain embodiments, the catalyst can be an acid catalyst. For example, the acid catalyst can be a mineral acid, an organic acid or mixtures thereof. The acid catalyst can be added prior to the reactive distillation or added during the reactive distillation. Non-limiting examples of acids can be sulfuric acid, phosphoric acid, trichloroacetic acid, methanesulfonic acid, benzenesulfonic acid, or p-toluenesulfonic acid. In certain embodiments, the acid catalyst can be a solid acid catalyst. In certain embodiments, the solid acid catalyst can be a zeolite, a clay, a resin, a silica gel or an alumina. In certain embodiments, the solid acid catalyst can be present in the distillation column. In certain embodiments, the solid acid catalyst can be part of the distillation column packing. In certain embodiments, the solid acid catalyst can be connected to or suspended from the distillation column packing or plates.

In certain embodiments, water can be removed from the top or overhead of the distillation column in the reactive distillation. In certain embodiments, an ester can be removed from the bottom or base of the distillation column in the reactive distillation. In certain embodiments, (3R)-hydroxybutyl (3R)-hydroxybutyrate can be removed from the bottom or base of the distillation column in the reactive distillation in a high boilers stream. In certain embodiments, the high boilers stream can have less than 50%, 40%, 30%, 25%, 20%, 15%, 10%, 9%, 8%, 7%, 6%, 5%, 4%, 3%, 2%, 1% of the amount of the (R)-1,3-butanediol that was in the culture medium containing (3R)-hydroxybutyl (3R)-hydroxybutyrate subjected to reactive distillation. In certain embodiments, the high boilers stream can have less than 50%, 40%, 30%, 25%, 20%, 15%, 10%, 9%, 8%, 7%, 6%, 5%, 4%, 3%, 2%, 1% of the amount of the (R)-3-hydroxybutyric acid that was in the culture medium containing (3R)-hydroxybutyl (3R)-hydroxybutyrate subjected to reactive distillation. The distillation column in a reactive distillation can be operated at pressures other than atmospheric pressure (ambient), including pressures less than atmospheric pressure (vacuum) or pressures greater than atmospheric pressure. Reduced operating pressures can be less than atmospheric pressure, or less than 500 mmHg, 200 mmHg, 100 mmHg, 50 mmHg, 40 mmHg, 30 mmHg, 20 mmHg, 15 mmHg, 10 mmHg, or 5 mmHg, for example.

For example, in an exemplary reactive distillation, a culture medium containing (3R)-hydroxybutyl (3R)-hydroxybutyrate which includes (R)-1,3-butanediol and (R)-3-hydroxybutyric acid is fed to a distillation column about a quarter of the way from the top of the distillation column. An acid catalyst, is then fed at near the midpoint of the distillation column. The column is operated at conditions that water, and other low boilers are removed from the top of the distillation column as a low boilers stream, and. a (3R)-hydroxybutyl (3R)-hydroxybutyrate product is removed from the base of the distillation column as a high boilers stream. The amount of unreacted (R)-1,3-butanediol and (R)-3-hydroxybutyric acid in material removed from the distillation column in the reactive distillation, in the low and high boilers stream, can, for example, be less than 10% (by weight) of the (R)-1,3-butanediol and (R)-3-hydroxybutyric acid that was in the culture material fed ot the reactive distillation column.

Distillation columns can, for example, be operated under vacuum (approximately 50 mbar) and a reflux ratio <0.5 to suppress degradation reactions of impurities and/or product in the feed which typically result in yield loss or color formation, and ensure adequate product recovery.

In certain embodiments, in an exemplary reactive distillation, the culture medium has been subjected to centrifugation, filtration, salt removal, evaporation or other procedure prior to reactive distillation. In some embodiments, the culture medium prior to being subjected to reactive distillation contains (R)-1,3-butanediol and (R)-3-hydroxybutyric acid, with negligible or no detectable (3R)-hydroxybutyl (3R)-hydroxybutyrate, as discussed above.

Centrifugation can be used to provide a (3R)-hydroxybutyl (3R)-hydroxybutyrate product substantially free of solids, including cell mass. Depending on the centrifuge configuration and size, operating speeds can vary from less than 500 rpm, generally from 500 rpm to 12,000 rpm or more than 12,000 rpm. The rpm from 500 to 12,000 can produce a centrifugal force of up to and over 15,000 times the force of gravity. Many centrifuge configurations for removal of cells and solids from a culture medium are known in the art and can be employed in the process of the invention. Such configurations include, for example, a disc-stack centrifuge and a decanter, or solid bowl centrifuge. Centrifugation can occur batch-wise or in a continuous fashion. All combinations of centrifugation configurations well known in the art can be employed in the process of the invention.

In certain embodiments, the process for isolating a (3R)-hydroxybutyl (3R)-hydroxybutyrate product includes subjecting the culture medium containing (3R)-hydroxybutyl (3R)-hydroxybutyrate to centrifugation. For example, the cells and solids can be separated by multiple centrifugations to increase the yield of (3R)-hydroxybutyl (3R)-hydroxybutyrate. Multiple centrifugations can it include centrifugation two times, three times, four times, and five times or more times, for example. Intermediate underflow streams can be diluted with water and passed through additional centrifugation to further increase recovery of the liquid product. Any combination of configurations can also be used to perform multiple centrifugations, such as combinations of the disc-stack and decanter centrifugations described above.

Microfiltration, for example, involves a low-pressure membrane process for separating colloidal and suspended particles in the range of about 0.05-10 microns. Useful configurations include cross-flow filtration using spiral-wound, hollow fiber, or flat sheet (cartridge) microfiltration elements. Microfiltration includes filtering through a membrane having pore sizes from about 0.05 microns to about 10.0 microns. Microfiltration membranes can have nominal molecular weight cut-offs (MWCO) of about 20,000 Daltons and higher. The term molecular weight cut-off is used to denote the size of particle, including polypeptides, or aggregates of peptides, that will be approximately 90% retained by the membrane. Polymeric, ceramic, or steel microfiltration membranes can be used to separate cells. Ceramic or steel microfiltration membranes have long operating lifetimes including up to or over 10 years. Microfiltration can be used in the clarification of culture medium. For example, microfiltration membranes can have pore sizes from about 0.05 microns to 10 micron, or from about 0.05 microns to 2 microns, about 0.05 microns to 1.0 micron, about 0.05 microns to 0.5 microns, about 0.05 microns to 0.2 microns, about 1.0 micron to 10 microns, or about 1.0 micron to 5.0 microns, or membranes can have a pore size of about 0.05 microns, about 0.1 microns, or about 0.2 microns For example, microfiltration membranes can have a MWCO from about 20,000 Daltons to 500,000 Daltons, about 20,000 Daltons to 200,000 Daltons, about 20,000 Daltons to 100,000 Daltons, about 20,000 Daltons to 50,000 Daltons, or with about 50,000 Daltons to 300,000 Daltons; or with a MWCO of about 20,000 Daltons, about 50,000 Dalton, about 100,000 Daltons or about 300,000 Daltons can be used in separating cell and solids from the culture medium. In certain embodiments, the process for isolating a (3R)-hydroxybutyl (3R)-hydroxybutyrate product includes subjecting the culture medium containing (3R)-hydroxybutyl (3R)-hydroxybutyrate to microfiltration.

Ultrafiltration is a selective separation process through a membrane using pressures up to about 145 psi (10 bar). Useful configurations include cross-flow filtration using spiral-wound, hollow fiber, or flat sheet (cartridge) ultrafiltration elements. These elements consist of polymeric or ceramic membranes with a molecular weight cut-off of less than about 200,000 Daltons. Ceramic ultrafiltration membranes are also useful since they have long operating lifetimes of up to or over 10 years. Ceramics have the disadvantage of being much more expensive than polymeric membranes. Ultrafiltration concentrates suspended solids and solutes of molecular weight greater than about 1,000 Daltons. Ultrafiltration includes filtering through a membrane having nominal molecular weight cut-offs (MWCO) from about 1,000 Daltons to about 200,000 Daltons (pore sizes of about 0.005 to 0.1 microns). For example, ultrafiltration membranes can have pore sizes from about 0.005 microns to 0.1 micron, or from about 0.005 microns to 0.05 microns, about 0.005 microns to 0.02 micron, or about 0.005 microns to 0.01 microns. For example, ultrafiltration membranes can have a MWCO from about 1,000 Daltons to 200,000 Daltons, about 1,000 Daltons to 50,000 Daltons, about 1,000 Daltons to 20,000 Daltons, about 1,000 Daltons to 5,000 Daltons, or with about 5,000 Daltons to 50,000 Daltons. Using ultrafiltration the permeate liquid will contain low-molecular-weight organic solutes, such as (3R)-hydroxybutyl (3R)-hydroxybutyrate, media salts, and water. The captured solids can include, for example, residual cell debris, DNA, and proteins. Diafiltration techniques well known in the art can be used to increase the recovery of (3R)-hydroxybutyl (3R)-hydroxybutyrate in the ultrafiltration step. In certain embodiments, the process for isolating a (3R)-hydroxybutyl (3R)-hydroxybutyrate product includes subjecting the culture medium containing (3R)-hydroxybutyl (3R)-hydroxybutyrate to ultrafiltration.

Another filtration procedure called nanofiltration can be used to separate out certain materials by size and charge, including carbohydrates, inorganic and organic salts, residual proteins and other high molecular weight impurities that remain after the previous filtration step. This procedure can allow the recovery of certain salts without prior evaporation of water, for example. Nanofiltration can separate salts, remove color, and provide desalination. In nanofiltration, the permeate liquid generally contains monovalent ions and low-molecular-weight organic compounds as exemplified by (3R)-hydroxybutyl (3R)-hydroxybutyrate. Nanofiltration includes filtering through a membrane having nominal molecular weight cut-offs (MWCO) from about 100 Daltons to about 2,000 Daltons (pore sizes of about 0.0005 to 0.005 microns). For example, nanofiltration membranes can have a MWCO from about 100 Daltons to 500 Daltons, about 100 Daltons to 300 Daltons, or about 150 Daltons to 250 Daltons. The mass transfer mechanism in nanofiltration is diffusion. The nanofiltration membrane allows the partial diffusion of certain ionic solutes (such as sodium and chloride), predominantly monovalent ions, as well as water. Larger ionic species, including divalent and multivalent ions, and more complex molecules are substantially retained (rejected). Larger non-ionic species, such as carbohydrates are also substantially retained (rejected). Nanofiltration is generally operated at pressures from 70 psi to 700, psi, from 200 psi to 650 psi, from 200 psi to 600 psi, from 200 psi to 450 psi, from 70 psi to 400 psi, of about 400 psi, of about 450 psi or of about 500 psi.

In certain embodiments, the process for isolating a (3R)-hydroxybutyl (3R)-hydroxybutyrate product includes subjecting the culture medium containing (3R)-hydroxybutyl (3R)-hydroxybutyrate to nanofiltration. One embodiment of a nanofiltration has a membrane with a molecular weight cut off of about 200 Daltons that rejects, for example, about 99% of divalent salts such as magnesium sulfate. A certain embodiment would have a nanofiltration membrane with a molecular weight cut off of about 150-300 Daltons for uncharged organic molecules.

Multiple filtration membranes can be used serially with gradually increasing refinement of the size of the solids, and/or charge of the solids, that are retained. Multiple filtrations can be useful to reduce fouling of membranes and aid in recovering individual components of the culture medium for recycle. For example, the multiple filtrations can be microfiltration followed by ultrafiltation followed by nanofiltration; microfiltration followed by nanofiltration; or ultrafiltration followed by nanofiltration. The invention includes all combinations and permutations of centrifugation, microfiltration, ultrafiltration and nanofiltration.

In certain embodiments, the process for isolating a (3R)-hydroxybutyl (3R)-hydroxybutyrate product includes subjecting the culture medium containing (3R)-hydroxybutyl (3R)-hydroxybutyrate to a separation procedure. In certain embodiments, subjecting the culture medium containing (3R)-hydroxybutyl (3R)-hydroxybutyrate to a separation procedure includes subjecting the culture medium containing (3R)-hydroxybutyl (3R)-hydroxybutyrate to one or more of the procedures of biomass deactivation, centrifugation, microfiltration, ultrafiltration and nanofiltration.

Ion exchange can be used to remove salts from a mixture, such as for example, a culture medium. Ion exchange elements can take the form of resin beads as well as membranes. Frequently, the resins can be cast in the form of porous beads. The resins can be cross-linked polymers having active groups in the form of electrically charged sites. At these sites, ions of opposite charge are attracted, but can be replaced by other ions depending on their relative concentrations and affinities for the sites. Ion exchange resins can be cationic or anionic, for example. Factors that determine the efficiency of a given ion exchange resin include the favorability for a given ion, and the number of active sites available. To maximize the active sites, large surface areas can be useful. Thus, small porous particles are useful because of their large surface area per unit volume.

Ion exchange resins can be anion exchange resins or cation exchange resins. The anion exchange resins can be strongly basic or weakly basic anion exchange resins, and the cation exchange resin can be strongly acidic or weakly acidic cation exchange resin. Non-limiting examples of ion-exchange resin that are strongly acidic cation exchange resins include AMBERJET™ 1000 Na, AMBERLITE™ IR10 or DOWEX™ 88; weakly acidic cation exchange resins include AMBERLITE™ IRC86 or DOWEX™ MAC3; strongly basic anion exchange resins include AMBERJET™ 4200 C1 or DOWEX™ 22; and weakly basic anion exchange resins include AMBERLITE™ IRA96, DOWEX™ 66 or DOWEX™ Marathon WMA. Ion exchange resins can be obtained from a variety of manufacturers such as Dow, Purolite, Rohm and Haas, Mitsubishi or others.

An ion exchange can be utilized for the removal of salts. The ion exchange can include, for example, both a cation exchange or an anion exchange, or a mixed cation-anion exchange, which include both cation exchange and anion exchange resins. In certain embodiments, ion exchange can be cation exchange and anion exchange in any order. In some embodiments, the ion exchange is an anion exchange followed by a cation exchange, or a cation exchange followed by an anion exchange, or a mixed cation-anion exchange. In certain embodiments, the ion exchange is an anion exchange, or a cation exchange. More than one ion exchange of a given type, can be used in the ion exchange. For example, the ion exchange can include a cation exchange, followed by an anion exchange, followed by a cation exchange and finally followed by an anion exchange.

In certain embodiments, the ion exchange uses a strongly acidic cation exchange and a weakly basic anion exchange Ion exchange can be carried out at temperatures from 20° C. to 60° C., from 30° C. to 60° C., 30° C. to 50° C., 30° C. to 40° C. or 40° C. to 50° C.; or at about 30° C., about 40° C., about 50° C., or about 60° C. Flow rates in ion exchange, such as ion exchange, can be from 1 bed volume per hour (BV/h) to 10 BV/h, 2 BV/h to 8 BV/h, 2 BV/h to 6 BV/h, 2 BV/h to 4 BV/h, 4 BV/h to 6 BV/h, 4 BV/h to 8 BV/h, 4 BV/h to 10 BV/h or 6 BV/h to 10 BV/h.

An evaporative crystallizer can be used to generate precipitated salts which can be removed by centrifugation, filtration or other mechanical means. In the process of isolating (3R)-hydroxybutyl (3R)-hydroxybutyrate, an evaporative crystallizer can serve for the removal of water from the culture medium and simultaneously cause supersaturation of the salts in the culture medium, and subsequent crystallization of the salts, which can then be removed. In some embodiments, the salts have a sufficiently low solubility in (3R)-hydroxybutyl (3R)-hydroxybutyrate that the separated (3R)-hydroxybutyl (3R)-hydroxybutyrate is about 98% salt-free. Examples of evaporative crystallizers can be a forced circulation crystallizer, a turbulence or draft-tube and baffle crystallizer, an induced circulation crystallizer, or an Oslo-type (also known as "growth-", "fluid-bed-" or "Krystal-" type) crystallizer.

Many of the evaporative crystallization apparatus allow for controlled crystal growth. In the removal of crystallization salts from a (3R)-hydroxybutyl (3R)-hydroxybutyrate product, the exact crystal morphology, size, and the like are generally inconsequential. Hence, removal of amorphous salts can be sufficient in the crystallization procedure. Thus, in some embodiments, other evaporation methods can be utilized that do not control crystal growth per se.

When salts are removed by nanofiltration and/or ion exchange, a reverse osmosis (RO) membrane filtration can be used to remove a portion of the water prior to evaporation. Water permeates the RO membrane while (3R)-hydroxybutyl (3R)-hydroxybutyrate is retained. In some embodiments, an RO membrane can concentrate a product, such as (3R)-hydroxybutyl (3R)-hydroxybutyrate to about 20%. One skilled in the art will recognize that the osmotic pressure from the (3R)-hydroxybutyl (3R)-hydroxybutyrate increases to a point where further concentration using an RO membrane can no longer be viable. Nonetheless, the use of an RO membrane is a useful low energy input method for concentrating (3R)-hydroxybutyl (3R)-hydroxybutyrate prior to the more energy intensive water evaporation process. Thus, on large scale, employing a RO membrane can be particularly useful.

There are many types and configurations of evaporators well known to those skilled in the art that are available for water removal. An evaporator is a heat exchanger in which a liquid is boiled to give a vapor that is also a low pressure steam generator. This steam can be used for further heating in another evaporator called another "effect." Removing water is accomplished by evaporation with an evaporator system which includes one or more effects. In some embodiments, a double- or triple-effect evaporator system can be used to separate water from (3R)-hydroxybutyl (3R)-hydroxybutyrate. Any number of multiple-effect evaporator systems can be used in the removal of water. A triple effect evaporator, or other evaporative apparatus configuration, can include dedicated effects that are evaporative crystallizers for salt recovery, for example the final effect of a triple effect configuration. Alternatively, mechanical vapor recompression or thermal vapor recompression evaporators can be utilized to reduce the energy required for evaporating water beyond what can be achieved in standard multiple effect evaporators.

Examples of evaporators include a falling film evaporator (which can be a short path evaporator), a forced circulation evaporator, a plate evaporator, a circulation evaporator, a fluidized bed evaporator, a rising film evaporator, a counterflow-trickle evaporator, a stirrer evaporator and a spiral tube evaporator.

In certain embodiments, the process for isolating a (3R)-hydroxybutyl (3R)-hydroxybutyrate product includes subjecting a (3R)-hydroxybutyl (3R)-hydroxybutyrate product to salt removal, water removal, or both salt removal and water removal. Removing salts from the separated (3R)-hydroxybutyl (3R)-hydroxybutyrate product can be achieved before or after removal of some or substantially all of the water from the separated (3R)-hydroxybutyl (3R)-hydroxybutyrate product. In certain embodiments of the process provided, salt removal is achieved through subjecting a (3R)-hydroxybutyl (3R)-hydroxybutyrate product to an ion exchange procedure. In certain embodiments of the process provided, salt removal includes crystallization. In certain embodiments of the process provided, water removal is achieved through subjecting a (3R)-hydroxybutyl (3R)-hydroxybutyrate product to evaporation. In certain embodiments of the process provided, water removal is achieved through subjecting a (3R)-hydroxybutyl (3R)-hydroxybutyrate product to reverse osmosis.

The process of isolating (3R)-hydroxybutyl (3R)-hydroxybutyrate can include distillation of a (3R)-hydroxybutyl (3R)-hydroxybutyrate product. The distillation can be carried out with a distillation system to produce a purified (3R)-hydroxybutyl (3R)-hydroxybutyrate product. The purified (3R)-hydroxybutyl (3R)-hydroxybutyrate product can be greater than 90%, 92%, 94%, 96%, 97%, 98%, 99%, 99.5%, 99.7% or 99.9% (3R)-hydroxybutyl (3R)-hydroxybutyrate on a weight/weight basis. The distillation system can be composed of one or more distillation columns that can be used to remove materials that have a higher or lower boiling point than (3R)-hydroxybutyl (3R)-hydroxybutyrate by generating streams of materials with boiling points higher or lower than (3R)-hydroxybutyl (3R)-hydroxybutyrate. The distillation columns can contain, for example, random-packing, structured-packing, plates, random- and structured-packing, random-packing and plates, or structured-packing and plates. As is known in the art, many types and configurations of distillation columns are available. The recovery of (3R)-hydroxybutyl (3R)-hydroxybutyrate in the purified (3R)-hydroxybutyl (3R)-hydroxybutyrate product can be calculated as a percentage of the amount of (3R)-hydroxybutyl (3R)-hydroxybutyrate in the purified (3R)-hydroxybutyl (3R)-hydroxybutyrate product divided by the amount of (3R)-hydroxybutyl (3R)-hydroxybutyrate in the (3R)-hydroxybutyl (3R)-hydroxybutyrate product that was purified.

A consideration in distillation is to minimize the amount of heating that a (3R)-hydroxybutyl (3R)-hydroxybutyrate product must undergo through the distillation process. Impurities or even the (3R)-hydroxybutyl (3R)-hydroxybutyrate can undergo thermal or chemical decomposition while being heated during distillation. Operating the distillation columns under reduced pressure (less than atmospheric pressure) or vacuum lowers the boiling temperature of the mixture in the distillation column and allows for operating the distillation column at lower temperatures. Any of the columns described in the various embodiments of the invention can be operated under reduced pressure. A common vacuum system can be used with all distillation columns to achieve a reduced pressure, or each column can have its own vacuum system. All combinations and permutations of the above exemplary vacuum configurations are included within the invention as described herein. The pressure of a distillation column can be measured at the top or condenser, the bottom or base, or anywhere in between. The pressure at the top of a distillation column can be different than the pressure in the base of the distillation column, and this pressure difference denotes the pressure drop across the distillation column. Different distillation columns of the same embodiment can be operated at different pressures. Pressures in a column can be ambient, less than ambient, or less than 500 mmHg, 200 mmHg, 100 mmHg, 50 mmHg, 40 mmHg, 30 mmHg, 20 mmHg, 15 mmHg, 10 mmHg, or 5 mmHg, for example.

It should be understood, that a step of removing higher or lowing boiling materials with a distillation column by distillation is not expected to be 100% effective, and that residual amounts of higher or lower boiling materials can still be present in the product stream after a distillation procedure. When it is described that a material is removed by a distillation procedure, it is to be understood that the removal can mean greater that 50%, 60%, 70%, 80%, 90%, 95%, 96%, 97%, 98%, 99%, 99.5% or 99.9% of the material removed from the feed to a distillation column.

The mixture to be purified can be fed to a distillation column and, depending on the operating conditions, the higher boiling or lower boiling materials can be removed from the mixture. For example, if lower boiling materials are removed, the lower boiling materials are boiled up and removed from the top of the distillation column, and the product-containing stream with the lower boiling materials removed exits from the bottom of the distillation column. This bottom stream can be fed to a next distillation column where the high boiling materials are removed from the product-containing stream. In the next distillation column, the product containing stream boils up and exits the distillation column from the top, and the higher boiling materials are removed from the bottom of the distillation column, thus providing a more pure product-containing stream. In another example, both the higher boiling and lower boiling materials can be removed from the product-containing stream, where in that case the lower boiling materials are boiled up and removed through the top of the column, the higher boiling materials are removed from the bottom of the column, and a product exits through a side-draw, which allows material to leave the column at an intermediate position between the top and bottom of the distillation column.

One embodiment of a distillation of a (3R)-hydroxybutyl (3R)-hydroxybutyrate product includes subjecting the (3R)-hydroxybutyl (3R)-hydroxybutyrate product to a first distillation column procedure to remove materials with boiling points lower than (3R)-hydroxybutyl (3R)-hydroxybutyrate from the (3R)-hydroxybutyl (3R)-hydroxybutyrate product to produce a first (3R)-hydroxybutyl (3R)-hydroxybutyrate product stream, and subjecting the first (3R)-hydroxybutyl (3R)-hydroxybutyrate-containing product stream to a second column distillation procedure to remove materials with boiling points higher than (3R)-hydroxybutyl (3R)-hydroxybutyrate as a first high-boilers stream, to produce a (3R)-hydroxybutyl (3R)-hydroxybutyrate product as a distillate.

In certain embodiments, materials with boiling points lower than (3R)-hydroxybutyl (3R)-hydroxybutyrate from a first distillation column procedure are a majority water. In certain embodiments, materials with boiling points lower than (3R)-hydroxybutyl (3R)-hydroxybutyrate from a first distillation column procedure are greater than 70%, 80%, 90%, 91%, 92%, 93%, 94%, 95%, 96%, 97%, 98% or 99% water by weight.

One embodiment of a distillation includes subjecting a (3R)-hydroxybutyl (3R)-hydroxybutyrate product to a first distillation column procedure to remove materials with boiling points higher than (3R)-hydroxybutyl (3R)-hydroxybutyrate as a first high-boilers stream, from the (3R)-hydroxybutyl (3R)-hydroxybutyrate product to produce a first (3R)-hydroxybutyl (3R)-hydroxybutyrate-containing product stream, and subjecting the first (3R)-hydroxybutyl (3R)-hydroxybutyrate containing product stream to a second column distillation procedure to remove materials with boiling points higher than (3R)-hydroxybutyl (3R)-hydroxybutyrate as a second high boilers stream and to remove materials with boiling points lower than (3R)-hydroxybutyl (3R)-hydroxybutyrate, to produce a purified (3R)-hydroxybutyl (3R)-hydroxybutyrate product, where the purified (3R)-hydroxybutyl (3R)-hydroxybutyrate product is collected from a side-draw of the second column distillation procedure.

In certain embodiments, the distillation includes subjecting the (3R)-hydroxybutyl (3R)-hydroxybutyrate product to 3 distillation column procedures, for instance, including an intermediate distillation procedure between the first distillation column procedure and second distillation column procedure. The intermediate distillation procedure can be operated to either remove materials with boiling points higher than (3R)-hydroxybutyl (3R)-hydroxybutyrate or boiling points lower than (3R)-hydroxybutyl (3R)-hydroxybutyrate.

For example, in certain embodiments the distillation includes subjecting a (3R)-hydroxybutyl (3R)-hydroxybutyrate product to a first distillation column procedure to produce a first (3R)-hydroxybutyl (3R)-hydroxybutyrate product stream, subjecting the first (3R)-hydroxybutyl (3R)-hydroxybutyrate product stream produced from the first distillation column procedure to an intermediate column distillation procedure to remove materials with boiling points lower than (3R)-hydroxybutyl (3R)-hydroxybutyrate; and subjecting the (3R)-hydroxybutyl (3R)-hydroxybutyrate product stream of the intermediate column distillation procedure to a second column distillation procedure, where (3R)-hydroxybutyl (3R)-hydroxybutyrate product is collected as a distillate from the second distillation procedure.

In certain embodiments, the (3R)-hydroxybutyl (3R)-hydroxybutyrate distillate product is greater than 90%, 91%, 92%, 93%, 94%, 95%, 96%, 97%, 98%, 99%, 99.5%, 99.6%, 99.7%, 99.8% or 99.9% (3R)-hydroxybutyl (3R)-hydroxybutyrate on a weight/weight basis. In certain embodiments, the (3R)-hydroxybutyl (3R)-hydroxybutyrate distillate product is greater than 99% (3R)-hydroxybutyl (3R)-hydroxybutyrate.

An adsorption procedure can be used to selectively adsorb impurities in a product compound. Various types of absorptive material or absorbents are known to those of skill in the art, and can be used with the present disclosure. Non-limiting examples of adsorptive material or adsorbent can be a resin, a silica gel, a clay, an activated alumina, a zeolites or an activated carbon. In certain embodiments, the (3R)-hydroxybutyl (3R)-hydroxybutyrate product can be subjected to an adsorption procedure. In certain embodiments, the adsorption procedure can include exposing the (3R)-hydroxybutyl (3R)-hydroxybutyrate product to an adsorptive material or adsorbent In certain embodiments, the adsorptive material can be activated carbon. In certain embodiments, the adsorption procedure includes passing the (3R)-hydroxybutyl (3R)-hydroxybutyrate product through a bed of adsorptive material. In certain embodiments, the adsorption procedure includes passing the (3R)-hydroxybutyl (3R)-hydroxybutyrate product through a bed of activated carbon to produce the isolated (3R)-hydroxybutyl (3R)-hydroxybutyrate. The adsorption procedure can be at ambient temperature, or can be at elevated temperatures from 30° C. to 90° C., 30° C. to 60° C., 30° C. to 50° C., 30° C. to 40° C., 40° C. to 80° C., 40° C. to 70° C., 40° C. to 60° C., 40° C. to 50° C., or 50° C. to 80° C.

In certain embodiments, the isolated (3R)-hydroxybutyl (3R)-hydroxybutyrate is greater than 90%, 91%, 92%, 93%, 94%, 95%, 96%, 97%, 98%, 99%, 99.5%, 99.6%, 99.7%, 99.8% or 99.9% (3R)-hydroxybutyl (3R)-hydroxybutyrate on a weight/weight basis. In certain embodiments, the isolated (3R)-hydroxybutyl (3R)-hydroxybutyrate is greater than 99% (3R)-hydroxybutyl (3R)-hydroxybutyrate.

An example of the process for isolating (3R)-hydroxybutyl (3R)-hydroxybutyrate derived from fermentation can include the steps of culturing a non naturally occurring microbial organism to produce a (3R)-hydroxybutyl (3R)-hydroxybutyrate in a culture medium, and subjecting the culture medium to one or more of the following isolation procedures: biomass deactivation, centrifugation, microfiltration, ultrafiltration, nanofiltration, ion exchange, reverse osmosis, evaporation, crystallization, esterification reaction, liquid-liquid extraction, chromatography, reactive distillation, distillation; and adsorption.

In one embodiment, a (3R)-hydroxybutyl (3R)-hydroxybutyrate product can be obtained by subjecting a culture medium containing (3R)-hydroxybutyl (3R)-hydroxybutyrate to: a separation, an evaporation, a salt removal, a reactive distillation, a distillation; and an adsorption. In certain embodiments, the separation procedure is filtration. In certain embodiments, the salt removal is by ion exchange. In certain embodiments, the reactive distillation is catalyzed by an acid catalyst. In certain embodiments, the acid catalyst is a mineral acid, and the mineral acid can be sulfuric acid or phosphoric acid. In certain embodiment, the reactive distillation removes water with a distillation column. In certain embodiments, the distillation includes a first column distillation procedure to remove water, an intermediate column distillation procedure to remove materials with a boiling point lower than (3R)-hydroxybutyl (3R)-hydroxybutyrate and a second column distillation procedure to remove materials with boiling points high than (3R)-hydroxybutyl (3R)-hydroxybutyrate. In certain embodiments, the adsorption uses activated carbon.

In one embodiment, a (3R)-hydroxybutyl (3R)-hydroxybutyrate product can be obtained by subjecting a culture medium as described herein to: an esterification reaction in the presence of a catalyst; liquid-liquid extraction, a distillation; and an adsorption. In certain embodiments, the catalyst is an acid catalyst. In certain embodiments, the catalyst is an enzyme. In certain embodiments, the liquid-liquid extraction occurs simultaneously or nearly simultaneously with the esterification reaction. In certain embodiments, the liquid-liquid extraction occurs after the esterification reaction. In certain embodiments the liquid-liquid extraction further includes a solvent evaporation. In certain embodiments, the distillation includes a first column distillation procedure to remove materials with a boiling point lower than (3R)-hydroxybutyl (3R)-hydroxybutyrate, and a second column distillation procedure to remove materials with boiling points high than (3R)-hydroxybutyl (3R)-hydroxybutyrate. In certain embodiments, the adsorption uses activated carbon.

In one embodiment, a (3R)-hydroxybutyl (3R)-hydroxybutyrate product can be obtained by subjecting a culture medium as described herein to: an esterification reaction in the presence of a catalyst; a chromatography, a distillation; and an adsorption. In certain embodiments, the catalyst is an acid catalyst. In certain embodiments, the catalyst is an enzyme. In certain embodiments the chromatography uses column chromatography. In certain embodiments, the column chromatography uses one or more columns. In certain embodiments, the distillation includes a first column distillation procedure to remove water, an intermediate column distillation procedure to remove materials with a boiling point lower than (3R)-hydroxybutyl (3R)-hydroxybutyrate and a second column distillation procedure to remove materials with boiling points high than (3R)-hydroxybutyl (3R)-hydroxybutyrate. In certain embodiments, the adsorption uses activated carbon.

The process of isolating (3R)-hydroxybutyl (3R)-hydroxybutyrate can further include subjecting a culture medium containing (3R)-hydroxybutyl (3R)-hydroxybutyrate to filtration. The filtration is microfiltration, ultrafiltration or nanofiltration, or any combination of microfiltration, ultrafiltration or nanofiltration, as described above, in combination with any or all of the embodiments of the invention.

The process of isolating (3R)-hydroxybutyl (3R)-hydroxybutyrate can further include subjecting a culture medium containing (3R)-hydroxybutyl (3R)-hydroxybutyrate to salt removal. The salt removal is ion exchange, as described above, in combination with any or all of the embodiments of the invention.

The process of isolating (3R)-hydroxybutyl (3R)-hydroxybutyrate can further include subjecting the a culture medium containing (3R)-hydroxybutyl (3R)-hydroxybutyrate to water removal. The water removal is by evaporation, as described above, in combination with any or all of the embodiments of the invention.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of (3R)-hydroxybutyl (3R)-hydroxybutyrate and/or (R)-1,3-butanediol and/or (R)-3-hydroxybutyric acid.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SIMPHENY®. This computational method and system is described in, for example, U.S. publication 2003/0233218, filed Jun. 14, 2002, and in International Patent Application No. PCT/US03/18838, filed Jun. 13, 2003. SIMPHENY® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SIMPHENY® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SIMPHENY®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SIMPHENY®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a (3R)-hydroxybutyl (3R)-hydroxybutyrate pathway can be introduced into a host organism. In some cases, it can be desirable to modify an activity of a (3R)-hydroxybutyl (3R)-hydroxybutyrate pathway enzyme or protein to increase production of (3R)-hydroxybutyl (3R)-hydroxybutyrate. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a (3R)-hydroxybutyl (3R)-hydroxybutyrate pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al., *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); GENE SITE SATURATION MUTAGENESIS™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional ts mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

In some embodiments, the carbon feedstock and other cellular uptake sources such as phosphate, ammonia, sulfate, chloride and other halogens can be chosen to alter the isotopic distribution of the atoms present in (3R)-hydroxybutyl (3R)-hydroxybutyrate or any (3R)-hydroxybutyl (3R)-hydroxybutyrate pathway intermediate. The various carbon feedstock and other uptake sources enumerated above will be referred to herein, collectively, as "uptake sources." Uptake sources can provide isotopic enrichment for any atom present in the product (3R)-hydroxybutyl (3R)-hydroxybutyrate or (3R)-hydroxybutyl (3R)-hydroxybutyrate pathway intermediate, or for side products generated in reactions diverging away from a (3R)-hydroxybutyl (3R)-hydroxybutyrate pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard.* in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950)$^{14}C/^{12}C$ ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides (3R)-hydroxybutyl (3R)-hydroxybutyrate or a (3R)-hydroxybutyl (3R)-hydroxybutyrate pathway intermediate that has a carbon-12, carbon-13, and carbon-14 ratio that reflects an atmospheric carbon, also referred to as environmental carbon, uptake source. For example, in some aspects the (3R)-hydroxybutyl (3R)-hydroxybutyrate or a (3R)-hydroxybutyl (3R)-hydroxybutyrate pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides (3R)-hydroxybutyl (3R)-hydroxybutyrate or a (3R)-hydroxybutyl (3R)-hydroxybutyrate pathway intermediate that has a carbon-12, carbon-13, and carbon-14 ratio that reflects petroleum-based carbon uptake source. In this aspect, the (3R)-hydroxybutyl (3R)-hydroxybutyrate or a (3R)-hydroxybutyl (3R)-hydroxybutyrate pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides (3R)-hydroxybutyl (3R)-hydroxybutyrate or a (3R)-hydroxybutyl (3R)-hydroxybutyrate pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced (3R)-hydroxybutyl (3R)-hydroxybutyrate or (3R)-hydroxybutyl (3R)-hydroxybutyrate pathway intermediate as disclosed herein, and to the products derived therefrom, wherein the (3R)-hydroxybutyl (3R)-hydroxybutyrate or a (3R)-hydroxybutyl (3R)-hydroxybutyrate pathway intermediate has a carbon-12, carbon-13, and carbon-14 isotope ratio of about the same value as the $CO_2$ that occurs in the environment. For example, in some aspects the invention provides bioderived (3R)-hydroxybutyl (3R)-hydroxybutyrate or a bioderived (3R)-hydroxybutyl (3R)-hydroxybutyrate intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived (3R)-hydroxybutyl (3R)-hydroxybutyrate or a bioderived (3R)-hydroxybutyl (3R)-hydroxybutyrate pathway intermediate as disclosed herein, wherein the bioderived product is chemically modified to generate a final product. Methods of chemically modifying a bioderived product of (3R)-hydroxybutyl (3R)-hydroxybutyrate, or an intermediate thereof, to generate a desired product are well known to those skilled in the art, as described herein. The invention further provides compositions having a carbon-12 versus carbon-13 versus carbon-14 isotope ratio of about the same value as the $CO_2$ that occurs in the environment, wherein the compositions are generated directly from or in combination with bioderived (3R)-hydroxybutyl (3R)-hydroxybutyrate or a bioderived (3R)-hydroxybutyl (3R)-hydroxybutyrate pathway intermediate as disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides compositions disclosed herein comprising bioderived (3R)-hydroxybutyl (3R)-hydroxybutyrate or bioderived (3R)-hydroxybutyl (3R)-hydroxybutyrate pathway intermediate, wherein the bioderived (3R)-hydroxybutyl (3R)-hydroxybutyrate or bioderived (3R)-hydroxybutyl (3R)-hydroxybutyrate pathway intermediate includes all or part of the (3R)-hydroxybutyl (3R)-hydroxybutyrate or (3R)-hydroxybutyl (3R)-hydroxybutyrate pathway intermediate used in the production of the composition. For example, the final composition can contain the bioderived (3R)-hydroxybutyl (3R)-hydroxybutyrate, (3R)-hydroxybutyl (3R)-hydroxybutyrate pathway intermediate, or a portion thereof that is the result of the manufacturing of compositions disclosed herein. Such manufacturing can include chemically reacting the bioderived (3R)-hydroxybutyl (3R)-hydroxybutyrate or bioderived (3R)-hydroxybutyl (3R)-hydroxybutyrate pathway intermediate (e.g. chemical conversion, chemical functionalization, chemical coupling, oxidation, reduction, polymerization, copolymerization and the like) into the final composition. Thus, in some aspects, the invention provides a biobased composition comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived (3R)-hydroxybutyl (3R)-hydroxybutyrate or bioderived (3R)-hydroxybutyl (3R)-hydroxybutyrate pathway intermediate as disclosed herein.

The bioderived (3R)-hydroxybutyl (3R)-hydroxybutyrate of the invention can be formulated into a composition as described herein, which can be ingestible. The compositions of the invention can further comprises a dietetically or pharmaceutically acceptable carrier. The compositions may be food products, beverages, drinks, dietary supplements, functional foods, nutraceuticals or pharmaceutical compositions.

The concentration of the compound of the invention in the composition depends on a variety of factors, including the particular format of the composition, the intended use of the composition and the target population. Generally the composition will contain the compound of the invention in an amount effective to reduce plasma levels of free fatty acids. Typically the amount is that required to achieve a circulating concentration of 3-hydroxybutyrate of from 10 µM to 20 mM, preferably from 50 µM to 10 mM, more preferably from 100 µM to 5 mM, in a subject who ingests the composition. In one embodiment, an amount is used to achieve a circulating concentration of from 0.7 mM to 5 mM, for example from 1 mM to 5 mM.

The bioderived (3R)-hydroxybutyl (3R)-hydroxybutyrate of the present invention is hydrolysed rapidly into two natural products, 3-hydroxybutyrate and (R)-1,3-butanediol, and is therefore a natural calorie source which can be classified as a food and can form part of a food product.

In accordance with the present invention a nutraceutical or functional food product can contain the bioderived (3R)-hydroxybutyl (3R)-hydroxybutyrate of the invention as defined herein in an amount effective to lower plasma levels of free fatty acids in a subject. Additionally, the nutraceutical or functional food product can contain the bioderived (3R)-hydroxybutyl (3R)-hydroxybutyrate in an amount effective to suppress appetite, treat obesity or promote weight loss in a subject.

The bioderived (3R)-hydroxybutyl (3R)-hydroxybutyrate of the invention can be formulated into a pharmaceutical composition or a dietary supplement by mixing with a acceptable carrier or excipient. Such a carrier or excipient can be a solvent, dispersion medium, coating, isotonic or absorption delaying agent, sweetener or the like. These include any and all solvents, dispersion media, coatings, isotonic and absorption delaying agents, sweeteners and the like. Suitable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular dosage form. The use of such media and agents for pharmaceutically active substances is well known in the art.

As non-limiting examples, the solid oral forms can contain, together with the bioderived (3R)-hydroxybutyl (3R)-hydroxybutyrate, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations can be manufactured in known manners, for example by means of mixing, granulating, tabletting, sugar coating, or film-coating processes.

Liquid dispersions for oral administration can be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolize to glucose or which only metabolize a very small amount to glucose. The suspensions and the emulsions may contain as carrier, for example, a natural gum, agar, sodium alginate, pectin, methylcellulose, carboxymethylcellulose or polyvinyl alcohol.

The bioderived (3R)-hydroxybutyl (3R)-hydroxybutyrate of the invention can also be formulated into granules or a powder. In this form it can be readily dispersed in water or other liquid such as tea or a soft drink for human subjects to drink, for instance a beverage or drink as described herein. It may also be encapsulated, tabletted or formulated with a physiologically acceptable vehicle into unit dosage forms. A unit dosage can comprise a therapeutically effective amount of the extract for a single daily administration, or it can be formulated into smaller quantities to provide for multiple doses in a day. The composition may thus, for instance, be formulated into tablets, capsules, syrups, elixirs, enteral formulations or any other orally administrable form.

Accordingly, in certain embodiments, provided herein is a composition comprising said bioderived (3R)-hydroxybutyl (3R)-hydroxybutyrate of the invention and a compound other than said bioderived (3R)-hydroxybutyl (3R)-hydroxybutyrate. In certain aspects the compound other than said bioderived (3R)-hydroxybutyl (3R)-hydroxybutyrate is a trace amount of a cellular portion of a non-naturally occurring microbial organism having a (3R)-hydroxybutyl (3R)-hydroxybutyrate pathway. In another aspects, the compound other than said bioderived (3R)-hydroxybutyl (3R)-hydroxybutyrate is a pharmaceutically acceptable carrier. In certain embodiments, a composition of the invention can comprise the bioderived (3R)-hydroxybutyl (3R)-hydroxybutyrate described herein, or a cell lysate or culture supernatant thereof. In certain embodiments, a composition of the invention includes the (3R)-hydroxybutyl (3R)-hydroxybutyrate being present at a level of up to 5%, 10%, 25%, 50%, 75%, 95%, 98% or 99% by weight of the composition. In certain aspects, the composition is in sold form or a gel. In other aspects, the composition is in a liquid form. In still further aspects, the composition comprises a flavoring. In certain embodiments, a composition of the invention includes a protein, a carbohydrate, a sugar, a sweetener, a fat, a fiber, a vitamin or a mineral.

Utilizing the compositions of the invention described herein, in certain aspects, the invention still further provides a method of treating or preventing a disease, a disorder or a condition in a subject comprising administering to a subject in need thereof a therapeutically effective amount of a bioderived (3R)-hydroxybutyl (3R)-hydroxybutyrate described herein or a composition of the invention, thereby treating said subject. In certain aspects, the disease, disorder or condition is exacerbated by or associated with elevated plasma levels of free fatty acids. For instance, non-limiting examples of diseases, disorders or conditions that can be treated or prevented include cognitive dysfunction, a cardiac condition, a neurodegenerative disorder, stroke, muscle impairment, muscle fatigue, obesity, diabetes, hyperthyroidism, metabolic syndrome, insulin resistance, Alzheimer's disease, Parkinson's disease, amyotrophic lateral sclerosis, epilepsy, astrocytoma, glioblastoma, Huntington's disease, cardiovascular disease, free radical toxicity, a hypoxic condition, and hyperglycemia.

In certain embodiments, provided herein is a method for suppressing appetite, treating obesity, promoting weight loss, maintaining a healthy weight, decreasing the ratio of fat to lean muscle, promoting alertness or improving cognitive function comprising administering to a subject in need thereof an effective amount of a bioderived (3R)-hydroxybutyl (3R)-hydroxybutyrate of the invention or a composition described herein.

It is understood that modifications which do not substantially affect the activity of the various embodiments of this invention are also provided within the definition of the invention provided herein. Accordingly, the following examples are intended to illustrate but not limit the present invention.

Example I

Production of (3R)-Hydroxybutyl (3R)-Hydroxybutyrate

Pathways that produce (3R)-hydroxybutyl (3R)-hydroxybutyrate from (R)-1,3-butanediol and (3R)-hydroxybutyryl-CoA, (3R)-hydroxybutyrate, (3R)-hydroxybutyl-ACP, acetoacetate, acetoacetyl-CoA or acetoacetyl-ACP are shown in FIG. 1. In one pathway, (3R)-hydroxybutyrate and (R)-1,3-butanediol are condensed to form (3R)-hydroxybutyl (3R)-hydroxybutyrate by an ester forming enzyme (step A). In another pathway the ester is formed from (3R)-hydroxybutyryl-CoA and (R)-1,3-butanediol by an alcohol transferase (step B). In yet another pathway, the ester is formed from (3R)-hydroxybutyl-ACP and (R)-1,3-butanediol by an (3R)-hydroxybutyryl-ACP:(R)-1,3-butanediol ester synthase (step F). The ester intermediate (3R)-hydroxybutyl 3-oxobutyrate is formed from acetoacetate, acetoacetyl-CoA or acetoacetyl-ACP and (R)-1,3-butanediol by an ester-forming enzyme, an alcohol transferase or acetoacetyl-ACP:(R)-1,3-butanediol ester synthase, respectively (steps C, D or G). Enantioselective reduction of (3R)-hydroxybutyl 3-oxobutyrate by a ketone reductase yields (3R)-hydroxybutyl (3R)-hydroxybutyrate (step E).

Conversion of (3R)-hydroxybutyrate and (R)-1,3-butanediol to the (3R)-hydroxybutyl (3R)-hydroxybutyrate product (step A) can also occur non-enzymatically, for example, by heating (3R)-hydroxybutyrate and (R)-1,3-butanediol in the presence of a dehydrating agent such as an acid catalyst. Similarly, conversion of acetoacetate and (R)-1,3-butanediol to (3R)-hydroxybutyl 3-oxobutyrate (step C) can also occur non-enzymatically.

Enzymes with (3R)-hydroxybutyl (3R)-hydroxybutyrate ester-forming activity can also be applied to form (3R)-hydroxybutyl (3R)-hydroxybutyrate esters directly from (3R)-hydroxybutyrate and (R)-1,3-butanediol, in an intracellular environment or in a solution such as a fermentation broth. The (3R)-hydroxybutyrate and (R)-1,3-butanediol can be produced by a microorganism comprising biosynthetic pathways known in the art, such as those described in U.S. Publication No. 2010/0330635 (published Dec. 30, 2010) and U.S. Publication No. 2012/0276606 (published Nov. 1, 2012), which are incorporated herein by reference. Exemplary pathways for producing the (3R)-hydroxybutyl (3R)-hydroxybutyrate pathway precursors from the central metabolic intermediate acetyl-CoA are shown in FIG. 2 and FIG. 3, and suitable enzymes for catalyzing each transformation are described in Example 2.

The (3R)-hydroxybutyl (3R)-hydroxybutyrate ester-forming enzymes can be targeted to the cytosol to enable intracellular conversion of (3R)-hydroxybutyrate and (R)-1,3-butanediol to their corresponding ester. Alternatively, the (3R)-hydroxybutyl (3R)-hydroxybutyrate ester-forming enzymes can be secreted into the fermentation medium to enable extracellular ester formation. A still further option is to add ester-forming enzymes to a solution containing (3R)-hydroxybutyrate and (R)-1,3-butanediol at conditions suitable for esterification. For example, the ester forming enzyme, (3R)-hydroxybutyrate and (R)-1,3-butanediol can be combined in a rotary evaporator flask and placed on an evaporator as described in U.S. Publication No. 2011/

0237666 (published Sep. 29, 2011), which is herein incorporated by reference. Evacuation of the flask with rotation at 40-45° C. proceeds until the diol is consumed.

Enzyme candidates for steps A-G are described below.

Alcohol Transferase (FIG. 1, Steps B and D)—(3R)-hydroxybutyryl-CoA:(R)-1,3-butanediol alcohol transferase or acetoacetyl-CoA:(R)-1,3-butanediol alcohol transferase Formation of (3R)-hydroxybutyryl or 3-oxobutyryl butanediol esters from (3R)-hydroxybutyryl-CoA or acetoacetyl-CoA and 1,3-butanediol can be catalyzed by enzymes having alcohol transferase (also known as ester synthase) activity. Several enzymes with alcohol transferase activity were demonstrated in Examples 1-10 of U.S. Pat. No. 7,901,915 (issued Mar. 8, 2011), which are herein incorporated by reference. These include Novozyme 435 (immobilized lipase B from *Candida antarctica*, Sigma), Lipase C2 from *Candida cylindracea* (Alphamerix Ltd), lipase from *Pseudomonas fluorescens* (Alphamerix Ltd), L-aminoacylase ex *Aspergillus* spp., and protease ex *Aspergillus oryzae*. Such enzymes were shown to form methyl and ethyl esters of acrylyl-CoA and methanol or ethanol, respectively. Such transferase enzymes can therefore be used to form esters with 1,3-butanediol.

Other suitable enzymes include the lipase encoded by calB from *Candida antarctica* (Efe et al., *Biotechnol. Bioeng.* 99:1392-1406 (2008)) and the EstF1 esterase from *Pseudomonas fluorescens* (Khalameyzer et al., *Appl. Environ. Microbiol.* 65:477-482 (1999)). Lipase enzymes encoded by lipB from Pseudomonasfluorescens and estA from *Bacillus subtilis* can also catalyze this transformation. The *B. subtilis* and *P. fluorescens* genes encode triacylglycerol lipase enzymes which have been cloned and characterized in *E. coli* (Dartois et al., *Biochim. Biophys. Acta* 1131:253-260 (1992); Tan et al., *Appl. Environ. Microbiol.* 58:1402-1407 (1992)).

| Gene | Accession No. | GI No. | Organism |
| --- | --- | --- | --- |
| calB | P41365.1 | 1170790 | *Candida antarctica* |
| EstF1 | AAC36352.1 | 3641341 | *Pseudomonas fluorescens* |
| lipB | P41773.1 | 1170792 | *Pseudomonas fluorescens* |
| estA | P37957.1 | 7676155 | *Bacillus subtilis* |

Additional candidate genes that encode enzymes for forming esters from acyl-CoA and alcohols include the *Acinetobacter* sp. ADP1 atfA encoding a bifunctional enzyme with both wax ester synthase (WS) and acyl-CoA: diacylglycerol acyltransferase (DGAT) activities (Kalscheuer et al., *J. Biol. Chem.* 278(10):8075-8082 (2003)); the *Simmondsia chinensis* gene AAD38041 encoding a enzyme required for the accumulation of waxes in jojoba seeds (Lardizabal et al., *Plant Physiology* 122:645-655 (2000)); the *Alcanivorax borkumensis* atfA1 and atfA2 encoding bifunctional WS/DGAT enzymes (Kalscheuer et al., *J. Bacteriol.* 189:918-928 (2007)); ths *Fragaria x ananassa* AAT encoding an alcohol acetyltransferasae (Noichinda et al., *FoodSci. Technol. Res.,* 5:239-242 (1999)); the Rosa hybrid cultivar AA TI encoding an alcohol acetyltransferase (Guterman et al., *Plant Mol. Biol.* 60:555-563 (2006)); the *Saccharomyces cerevisiae* ATF1 and ATF2 encoding alcohol acetyltransferases (Mason et al., *Yeast* 16:1287-1298 (2000)); and Ws1 and Ws2 from *Marinobacter hydrocarbonoclasticus* (Holtzapple, E. and Schmidt-Dannert, C., *J. Bacteriol.* 189(10):3804-3812 (2007). The carboxylesterase from *Lactococcus lactis*, encoded by estA, catalyzes the formation of esters from acetyl-CoA and alcohols such as ethanol and methanethiol (Nardi et al., *J. Appl. Microbiol.* 93:994-1002 (2002)). The alcohol O-acetyltransferase from *Saccharomyces uvarum* converts a wide range of alcohol substrates including branched-chain alcohols to their corresponding acetate esters (Yoshioka and Hashimoto, *Agricul. and Biol. Chem.* 45:2183-2191 (1981)). The gene associated with this activity has not been identified to date. The protein sequences of the enzymes encoded by these genes are provided below.

| Gene | GenBank ID | GI Number | Organism |
| --- | --- | --- | --- |
| atfA | Q8GGG1 | 81478805 | *Acinetobacter* sp. ADP1 |
| AF149919.1: 13 . . . 1071 | AAD38041 | 5020219 | *Simmondsia chinensis* |
| atfA1 | YP694462 | 110835603 | *Alcanivorax borkumensis* SK2 |
| atfA2 | YP693524 | 110834665 | *Alcanivorax borkumensis* SK2 |
| AAT | AAG13130.1 | 10121328 | *Fragaria x ananassa* |
| AAT1 | Q5I6B5 | 75105208 | *Rosa hybrid cultivar* |
| ATF1 | P40353 | 2506980 | *Saccharomyces cerevisiae* |
| ATF2 | P53296 | 1723729 | *Saccharomyces cerevisiae* |
| Ws2 | ABO21021.1 | 126567232 | *Marinobacter hydrocarbonoclasticus* |
| Ws1 | ABO21020.1 | 126567230 | *Marinobacter hydrocarbonoclasticus* |
| EstA | AAF62859.1 | 7453516 | *Lactococcus lactis* |

Ester Forming Enzymes (FIG. 1, Steps A and C)—3-hydroxybutyryl butanediol ester forming enzyme or 3-oxobutyryl butanediol ester forming enzyme Enzymes that catalyze the intra- or interconversion of esters to acids and alcohols can also catalyze the formation of 1,3-butanediol esters. Enzymes with this activity include paraoxonase, lipase, esterase, amidase, epoxide hydrolase, wax ester synthase and alcohol transferase enzymes.

The *Homo sapiens* paraoxonase enzymes PON1, PON1 (G3C9), and PON3 (EC 3.1.8.1) possess both arylesterase and organophosphatase activities and also may possess (3R)-hydroxybutyl (3R)-hydroxybutyrate ester-forming activity. PON1 has a common polymorphic site at residue 192, glutamine (R) or arginine (Q), that results in the formation of two isozymes (R and Q) with qualitative differences. For example, the R isozyme has a higher esterase activity on GBL than the Q isozyme (Billecke et al., *Drug Metab Dispos.* 28:1335-1342 (2000)). In *H. sapiens* cells, PON1 resides on high-density lipoprotein (HDL) particles, and its activity and stability require this environment. Wild type and recombinant PON1 enzymes have been functionally expressed in other organisms (Rochu et al., *Biochem. Soc. Trans.* 35:1616-1620 (2007); Martin et al., *Appl. Environ. Microbiol.* (2009)). A directed evolution study of PON1 yielded several mutant enzymes with improved solubility and catalytic properties in *E. coli* (nucleotide accession numbers AY499188-AY499199) (Aharoni et al., *Proc. Natl. Acad. Sci. U.S.A* 101:482-487 (2004)). One recombinant variant from this study, G3C9 (Aharoni et al., *Proc. Natl. Acad. Sci. U.S.A* 101:482-487 (2004)), was recently used in an integrated bioprocess for the pH-dependent production of 4-valerolactone from levulinate (Martin et al., *Appl. Environ. Microbiol.* (2009)). Human PON3 is yet another suitable enzyme that may possess the desired ester-forming activity (Draganov et al., *J. Lipid Res.* 46:1239-1247 (2005)). PGP-24T 1

| Gene | Accession No. | GI No. | Organism |
|---|---|---|---|
| PON1 | NP_000437.3 | 19923106 | *Acinetobacter* sp. ADP1 |
| PON1 (G3C9) | AAR95986.1 | 40850544 | *Simmondsia chinensis* |
| PON3 | NP_000931.1 | 29788996 | *Homo sapiens* |

Additional ester-forming enzymes include the *Candida antarctica* lipase B (Efe et al., *Biotechnol. Bioeng.* 99:1392-1406 (2008)) and the esterase from *Pseudomonas fluorescens*, encoded by EstF1 (Khalameyzer et al., *Appl. Environ. Microbiol.* 65:477-482 (1999)). Other lipase enzymes from organisms such as Pseudomonasfluorescens and *Bacillus subtilis* may also catalyze this transformation. The *B. subtilis* and *P. fluorescens* genes encode triacylglycerol lipase enzymes which have been cloned and characterized in *E. coli* (Dartois et al., *Biochim. Biophys. Acta* 1131:253-260 (1992); Tan et al., *Appl. Environ. Microbiol.* 58:1402-1407 (1992)).

| Gene | Accession No. | GI No. | Organism |
|---|---|---|---|
| calB | P41365.1 | 1170790 | *Acinetobacter* sp. ADP1 |
| EstF1 | AAC36352.1 | 3641341 | *Simmondsia chinensis* |
| lipB | P41773.1 | 1170792 | *Alcanivorax borkumensis* SK2 |
| estA | P37957.1 | 7676155 | *Alcanivorax borkumensis* SK2 |

The amidase from *Brevibacterium* sp. R312 (EC 3.5.1.4) hydrolyzes ethylacrylate (Thiery et al., *J. Gen. Microbiol.* 132:2205-8 (1986); Soubrier et al., *Gene* 116:99-104 (1992)). The microsomal epoxide hydrolase from *Rattus norvegicus* (EC 3.3.2.9) has activity on hydrolyzing glycidyl methacrylate and is another suitable enzyme (Guengerich et al., *Rev. Biochem. Toxicol.* 4:5-30 (1982)). The protein sequences of these genes are provided below.

| Gene | GenBank ID | GI Number | Organism |
|---|---|---|---|
| amiE | JC1174 | 98711 | *Acinetobacter* sp. ADP1 |
| Eph-1 | P07687.1 | 123928 | *Simmondsia chinensis* |

Formation of 1,3-BDO esters may also be catalyzed by enzymes in the 3.1.1 family that act on carboxylic ester bonds molecules for the interconversion between cyclic lactones and the open chain hydroxycarboxylic acids. The L-lactonase from *Fusarium proliferatum* ECU2002 exhibits lactonase and esterase activities on a variety of lactone substrates (Zhang et al., *Appl. Microbiol. Biotechnol.* 75:1087-1094 (2007)). The 1,4-lactone hydroxyacylhydrolase (EC 3.1.1.25), also known as 1,4-lactonase or gamma-lactonase, is specific for 1,4-lactones with 4-8 carbon atoms. The gamma lactonase in human blood and rat liver microsomes was purified (Fishbein et al., *J Biol Chem* 241:4835-4841 (1966)) and the lactonase activity was activated and stabilized by calcium ions (Fishbein et al., *J Biol Chem* 241:4842-4847 (1966)). The optimal lactonase activities were observed at pH 6.0, whereas high pH resulted in hydrolytic activities (Fishbein and Bessman, *J. Biol. Chem.* 241:4842-4847 (1966)). Genes from *Xanthomonas campestris*, *Aspergillus niger* and *Fusarium oxysporum* have been annotated as 1,4-lactonase and can be utilized to catalyze the transformation of 4-hydroxybutyrate to GBL (Zhang et al., *Appl. Microbiol. Biotechnol.* 75:1087-1094 (2007)).

| Gene | Accession No. | GI No. | Organism |
|---|---|---|---|
| EU596535.1:1...1206 | ACC61057.1 | 183238971 | *Fusarium proliferatum* |
| xccb100_2516 | YP_001903921.1 | 188991911 | *Xanthomonas campestris* |
| An16g06620 | CAK46996.1 | 134083519 | *Aspergillus niger* |
| BAA34062 | BAA34062.1 | 3810873 | *Fusarium oxysporum* |

Formation of (3R)-hydroxybutyl (3R)-hydroxybutyrate from ethyl (3R)-hydroxybutyrate and (R)-1,3-butanediol using solid-supported lipase B from *Candida antarctica* has also been shown (U.S. Publication No. 2011/0237666 (published Sep. 29, 2011); which is herein incorporated by reference). Briefly, the substrants were combined in a 20 litre rotary evaporator flask and placed on a large-scale Buchi evaporator. The system was evacuated to 8-10 torr with rotation at 40-45° C. until the diol was consumed. The crude material was then filtered to separate the enzyme and excess ethyl (3R)-hydroxybutyrate was removed by evaporation. Activated carbon was added, mixed on a rotary evaporator, and then the neat mixture was filtered through a CELITE plug. The CELITE plug was then washed with ether, the solvent removed from the washings in vacuo, and the residue added to the bulk for storage.

(3R)-Hydroxybutyl 3-oxobutyrate reductase (FIG. 1, Step E)

The enantio selective reduction of (3R)-hydroxybutyl 3-oxobutyrate to (3R)-hydroxybutyl (3R)-hydroxybutyrate can be catalyzed by (3R)-hydroxybutyl 3-oxobutyrate reductase. Enzymes with this activity are described in U.S. Publication No. 2012/0064611 (published Mar. 15, 2012), which is herein incorporated by reference. Selective (R)-enantiomer forming ketoreductase and alcohol dehydrogenase enzymes have been described (Moore et al., *Acc. Chem. Res.*, 40:1412-19 (2007)). Two commercially available ketoreductases, KRED-101 and KRED-107, catalyze the reduction of ethyl acetoacetate to ethyl(3R)-hydroxybutyrate. Other commercially available stereoselective ketoreductase and alcohol dehydrogenase enzymes described in the Moore et al., supra, include KRED-111, KRED-112, KRED-113, KRED-115, KRED-121, KRED-123, KRED-128, KRED-129, KRED-131, KRED-A1n, KRED-A1x, ADH-LB and ADH-LK. Enzymes with activity on 3-hydroxybutyl 3-oxobutyrate include ADH-LB, ADH-RS2, ADH-T and CDX-003. The ADH-LB enzyme is NADPH-dependent and exhibits high regioselectivity for forming the R enantiomer (Leuchs and Greiner, *Chem Biochem Eng Q* 25: 267-81 (2011)). The ADH-RS2 is encoded by RER_23910 of *Rhodococcus erythropolis*. International Publication No. WO 03/091423 (published Nov. 6, 2003).

| Gene | Accession No. | GI No. | Organism |
|---|---|---|---|
| ADH-LB | CAD66648.1 | 28400789 | *Lactobacillus brevis* |
| ADH-RS2 | BAH33099.1 | 226184995 | *Rhodococcus erythropolis* |

Ester Synthase (FIG. 1, Steps F and G)—(3R)-hydroxybutyryl-ACP:(R)-1,3-butanediol ester synthase and acetoacetyl-ACP:(R)-1,3-butanediol ester synthase Formation of (3R)-hydroxybutyryl or 3-oxobutyryl butanediol esters from (3R)-hydroxybutyryl-ACP or acetoacetyl-ACP and 1,3-butanediol (steps F and G) can be catalyzed by enzymes having ester synthase activity. Ester synthase enzymes that utilize acyl-ACP as the acyl-thioester substrate are known in the art (see for example WO/2013/048557). The acyl-ACP wax ester synthase enzymes from *Marinobacter hydrocarbonoclasticus* can use long-chain (C6-C24) or short-chain (C1-C5) alcohol substrates. The accession numbers of this enzyme and homologs are shown in the table below. Alternately, alcohol transferase or ester synthase enzymes that utilize acyl-CoA as the acyl-thioester substrate such as wax ester synthase may be engineered or evolved to accept acyl-ACP as the acyl-thioester substrate. Alcohol transferase enzymes are described above.

| Protein | GenBank ID | GI Number | Organism |
|---|---|---|---|
| MARHY0163 | YP_005428090.1 | 387812613 | *Marinobacter hydrocarbonoclasticus* |
| MARHY3006 | YP_005430893.1 | 387815403 | *Marinobacter hydrocarbonoclasticus* |
| Maqu_0168 | YP_957462.1 | 120553111 | *Marinobacter aquaeolei* |
| Maqu_3067 | YP_960328.1 | 120555977 | *Marinobacter aquaeolei* |
| MSNKSG1_15691 | ZP_23817545.1 | 471985756 | *Marinobacter santoriniensis* |
| HP15_3875 | YP_005887567.1 | 385333616 | *Marinobacter adhaerens* HP15 |
| HP15_2946 | YP_005886638.1 | 385332687 | *Marinobacter adhaerens* HP15 |
| ABO_2742 | YP_694462.1 | 110835603 | *Alcanivorax borkumensis* SK2 |
| HCH_05018 | YP_436128.1 | 83647693 | *Hahella chejuensis* |
| MELB17_04692 | ZP_01736818.1 | 126665837 | *Marinobacter sp.* ELB17 |
| MRBBS_3121 | YP_006559470.1 | 399546162 | *Marinobacter sp.* BSs20148 |

Example II

Production of (3R)-Hydroxybutyl (3R)-Hydroxybutyrate Precursors from Acetyl-CoA

The conversion of acetyl-CoA to (R)-1,3-butanediol and other (3R)-hydroxybutyl (3R)-hydroxybutyrate precursors can be accomplished by a number of pathways shown in FIG. 2. For production of acetoacetyl-CoA, in the first step of the pathway, acetyl-CoA can converted to acetoacetyl-CoA by acetoacetyl-CoA thiolase (Step A). Alternatively, acetyl-CoA can be converted to malonyl-CoA by acetyl-CoA carboxylase (Step E), and acetoacetyl-CoA can be synthesized from acetyl-CoA and malonyl-CoA by acetoacetyl-CoA synthase (Step F). Acetoacetyl-CoA can be stereoselectively reduced to (3R)- or (3S)-hydroxybutyryl-CoA (Steps B or J). Conversion of (3S)-hydroxybutyryl-CoA to (3R)-hydroxybutyryl-CoA can be catalyzed by an epimerase (Step K). (3R)-Hydroxybutyryl-CoA can then be converted to its corresponding aldehyde either directly by an acyl-CoA reductase or indirectly by a CoA hydrolase, transferase or synthetase in combination with a (3R)-hydroxybutyrate reductase. The aldehyde intermediate can then be further reduced to (R)-1,3-butanediol. Accordingly, 1,3-butanediol can be made via one or more of the following pathways depicted in FIG. 2:
  (i) A/B/C/D;
  (ii) A/B/H/I/D;
  (iii) A/J/K/C/D;
  (iv) A/J/K/H/I/D;
  (v) E/F/B/C/D;
  (vi) E/F/B/H/I/D;
  (vii) E/F/J/K/C/D; or
  (viii) E/F/J/K/H/I/D.

Other (3R)-hydroxybutyl (3R)-hydroxybutyrate precursors, such as (3R)-hydroxybutyrate and acetoacetate can be made via one or more of the following pathways depicted in FIG. 2. For (3R)-hydroxybutyrate, the pathways can include:
  (i) A/B/H
  (ii) A/B/C/I
  (iii) A/J/K/H
  (iv) A/J/K/C/I
  (v) E/F/B/H
  (vi) E/F/J/K/H
  (vii) E/F/B/C/I
  (viii) E/F/J/K/C/I For acetoacetate, the pathways can include:
  (i) A/G;
  (ii) E/F/G Enzyme activities required for the reactions shown in FIG. 2 are listed in the table below.

| Label | Function | Step |
|---|---|---|
| 1.1.1.a | Oxidoreductase (oxo to alcohol) | 2B, 2J, 2D |
| 1.2.1.a | Oxidoreductase or oxidase (aldehyde to acid) | 2I |
| 1.2.1.b | Oxidoreductase (acyl-CoA to aldehyde or alcohol) | 2C or C + D |
| 1.2.1.e | Oxidoreductase (acid to aldehyde) | 2I |
| 2.3.1.b | Beta-ketothioase | 2A |
| 2.3.1.e | Synthase | 2F |
| 2.8.3.a, 3.1.2.a, 6.2.1.a | CoA hydrolase, transferase or synthetase | 2G, 2H |
| 5.1.2 | Epimerase | 2K |
| 6.4.1.a | Acetyl-CoA carboxylase | 2E |

1.1.1.a Oxidoreductase (Oxo to Alcohol)

Acetoacetyl-CoA reductase enzymes (EC 1.1.1.35, EC 1.1.1.35, EC 1.1.1.-) catalyze the reduction of acetoacetyl-CoA to (3R)-hydroxybutyryl-CoA (FIG. 2, Step B) or (3S)-hydroxybutyryl-CoA (FIG. 2, Step J). Stereoselective enzymes catalyze the formation of the (R) or (S) isomer and can be either NADH or NADPH dependent (Tseng et al., *AEM* 75:3137-45 (2009)). (S)-isomer forming enzymes are generally NADH dependent and can be found in organisms that contain butanol fermentation pathways such as *Clostridium beijerinckii* (Colby and Chen, *AEM* 58:3297-302 (1992)). The (R)-isomer is formed as an intermediate of poly-hydroxybutyrate biosynthesis.

Acetoacetyl-CoA reductase enzymes selective for the (S) isomer of 3-hydroxybutyryl-CoA include the NADH-dependent Hbd of *Clostridium beijerinckii*, an NADH dependent enzyme (Colby and Chen, *AEM* 58: 3297-302 (1992)). Similar enzymes are found in other Clostridial organisms. The enzyme from *Clostridium acetobutylicum*, encoded by hbd, has been cloned and functionally expressed in *E. coli* (Youngleson et al., *J. Bacteriol.* 171:6800-6807 (1989)). Additionally, subunits of two fatty acid oxidation complexes in *E. coli*, encoded by fadB and fadJ, function as (3S)-hydroxyacyl-CoA dehydrogenases (Binstockand Schulz, *Methods Enzymol.* 71 Pt C:403-411 (1981)). Additional gene candidates include Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos Taurus* (Wakil et al., *J. Biol. Chem.* 207:631-638 (1954)). Similar enzymes have been found in *Metallosphaera sedula* and *Ralstonia eutropha* (Berg et al., *Science* 318:1782-1786 (2007)).

| Protein | Genbank ID | GI number | Organism |
|---|---|---|---|
| Hbd | NP_349314.1 | NP_349314.1 | Clostridium acetobutylicum |
| Hbd | AAM14586.1 | AAM14586.1 | Clostridium beijerinckii |
| Hbd2 | EDK34807.1 | 146348271 | Clostridium kluyveri |
| Hbd1 | EDK32512.1 | 146345976 | Clostridium kluyveri |
| fadB | P21177.2 | 119811 | Escherichia coli |
| fadJ | P77399.1 | 3334437 | Escherichia coli |
| Msed_1423 | YP_001191505 | YP_001191505 | Metallosphaera sedula |
| Msed_0399 | YP_001190500 | YP_001190500 | Metallosphaera sedula |
| Msed_0389 | YP_001190490 | YP_001190490 | Metallosphaera sedula |
| Msed_1993 | YP_001192057 | YP_001192057 | Metallosphaera sedula |
| paaH1 | YP_724801.1 | 113866312 | Ralstonia eutropha |

An exemplary (R) isomer-forming acetoacetyl-CoA reductase is the NADPH dependent phaB gene product of *Rhodobacter spaeroides* (Alber et al., *Mol. Micro.* 61:297-309 (2006)). Similar enzymes are found in *Ralstonia eutropha* H16 (Haywood et al., *FEMS Microbiol Lett* 52:259-64 (1988)). Yet another enzyme that converts acetoacetyl-CoA reductase to (3R)-hydroxybutyryl-CoA is phbB from *Zoogloea ramigera* (Ploux et al., *Eur. J. Biochem.* 174:177-182 (1988)).

| Protein | Genbank ID | GI number | Organism |
|---|---|---|---|
| phaB | YP_353825.1 | 77464321 | Rhodobacter sphaeroides |
| phbB | P23238.1 | 130017 | Zoogloea ramigera |
| phaB3 | YP_726636.1 | 113868147 | Ralstonia eutropha |
| phaB2 | YP_726470.1 | 113867981 | Ralstonia eutropha |
| phaB1 | YP_725942.1 | 113867453 | Ralstonia eutropha |

The reduction of acetoacetyl-CoA to (3R)-hydroxybutyryl-CoA is also catalyzed by acetoacetyl-ACP reductase or 3-oxoacyl-ACP reductase enzymes (EC 1.1.1.100). The *E. coli* 3-oxoacyl-ACP reductase is encoded by fabG. Key residues responsible for binding the acyl-ACP substrate to the enzyme have been elucidated (Zhang et al., *J. Biol. Chem.* 278:52935-43 (2003)). Additional enzymes with this activity have been characterized in *Bacillus anthracis* (Zaccai et all, *Prot. Struct. Funct. Gen.* 70:562-7 (2008)), *Mycobacterium tuberculosis* (Gurvitz, *Mol. Genet. Genomics* 282:407-16 (2009)) and *Geobacillus stearothermophilus* (U.S. Publication No. 2012/0276606 (published Nov. 1, 2012)). The beta-ketoacyl reductase (KR) domain of eukaryotic fatty acid synthase also catalyzes this activity (Smith, *FASEB J*, 8:1248-59 (1994)).

| Protein | GenBank ID | GI Number | Organism |
|---|---|---|---|
| fabG | P0AEK2.1 | 84028081 | Escherichia coli |
| fabG | AAP27717.1 | 30258498 | Bacillus anthracis |
| FabG1 | NP_215999.1 | 15608621 | Mycobacterium tuberculosis |
| FabG4 | YP_003030167.1 | 253797166 | Mycobacterium tuberculosis |

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.*, 66:5231-5235 (2000)), ADH2 from *Saccharomyces cerevisiae* (Atsumi et al., *Nature*, 451:86-89 (2008)), yqhD from *E. coli* which has preference for molecules longer than C3 (Sulzenbacher et al., *J. Molecular Biology*, 342:489-502 (2004)), and bdh I and bdh II from *C. acetobutylicum* which converts butyraldehyde into butanol (Walter et al., *J. Bacteriology*, 174:7149-7158 (1992)). The gene product of yqhD catalyzes the reduction of acetaldehyde, malondialdehyde, propionaldehyde, butyraldehyde, and acrolein using NADPH as the cofactor (Perez et al., *J. Biol. Chem.*, 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol*, 22:249-254 (1985)). Additional aldehyde reductase candidates are encoded by bdh in *C. saccharoperbutylacetonicum* and Cbei_1722, Cbei_2181 and Cbei_2421 in *C. beijerinckii*. The (R)-2-octanol dehydrogenase of *Ogataea wickerhamii* is active on (R)-hydroxybutyraldehyde (U.S. Publication No. 2012/0276606 (published Nov. 1, 2012)).

| Protein | GenBank ID | GI number | Organism |
|---|---|---|---|
| alrA | BAB12273.1 | 9967138 | Acinetobacter sp. strain M-1 |
| ADH2 | NP_014032.1 | 6323961 | Saccharomyces cerevisiae |
| yqhD | NP_417484.1 | 16130909 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |
| bdh | BAF45463.1 | 124221917 | Clostridium saccharoperbutylacetonicum |
| Cbei_1722 | YP_001308850 | 150016596 | Clostridium beijerinckii |
| Cbei_2181 | YP_001309304 | 150017050 | Clostridium beijerinckii |
| Cbei_2421 | YP_001309535 | 150017281 | Clostridium beijerinckii |
| odh | BAF36551.1 | 117580174 | Ogataea wickerhamii |

Enzymes exhibiting 4-hydroxybutyraldehyde reductase activity (EC 1.1.1.61) are also suitable for converting (3R)-hydroxybutyraldehyde to 1,3-BDO. Such enzymes have been characterized in *Ralstonia eutropha* (Bravo et al., *J. Forensic Sci.*, 49:379-387 (2004)), *Clostridium kluyveri* (Wolff et al., *Protein Expr. Purif.*, 6:206-212 (1995)) and *Arabidopsis thaliana* (Breitkreuz et al., *J. Biol. Chem.*, 278:41552-41556 (2003)). Yet another gene is the alcohol dehydrogenase; adhI from *Geobacillus thermoglucosidasius* (Jeon et al., *J. Biotechnol.*, 135:127-133 (2008)).

| Protein | GenBank ID | GI number | Organism |
|---|---|---|---|
| 4hbd | YP_726053.1 | 113867564 | Ralstonia eutropha H16 |
| 4hbd | L21902.1 | 146348486 | Clostridium kluyveri DSM 555 |
| 4hbd | Q94B07 | 75249805 | Arabidopsis thaliana |
| adhI | AAR91477.1 | 40795502 | Geobacillus thermoglucosidasius M10EXG |

Another exemplary aldehyde reductase is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J. Mol. Biol.*, 352:905-917 (2005)). The reversibility of the human 3-hydroxyisobutyrate dehydrogenase was demonstrated using isotopically-labeled substrate (Manning et al., *Biochem J.*, 231:481-484 (1985)). Additional genes encoding this enzyme include 3hidh in *Homo sapiens* (Hawes et al., *Methods Enzymol*, 324:218-228 (2000)) and *Oryctolagus cuniculus* (Hawes et al., supra; Chowdhury et al., *Biosci. Biotechnol Biochem.*, 60:2043-2047 (1996)), mmsB in *Pseudomonas aeruginosa* and *Pseudomonas putida* (Liao et al., US patent 20050221466), and dhat in *Pseudomonas putida* (Aberhart et al., *J. Chem. Soc.*, 6:1404-1406 (1979); Chowdhury et al., supra; Chowdhury et al., *Biosci. Biotechnol Biochem.*, 67:438-441 (2003)).

| Protein | GenBank ID | GI number | Organism |
|---|---|---|---|
| P84067 | P84067 | 75345323 | *Thermus thermophilus* |
| 3hidh | P31937.2 | 12643395 | *Homo sapiens* |
| 3hidh | P32185.1 | 416872 | *Oryctolagus cuniculus* |
| mmsB | P28811.1 | 127211 | *Pseudomonas aeruginosa* |
| mmsB | NP_746775.1 | 26991350 | *Pseudomonas putida* |
| dhat | Q59477.1 | 2842618 | *Pseudomonas putida* |

1.2.1.a. Oxidoreductase (Aldehyde to Acid)

Aldehyde dehydrogenase enzymes in EC class 1.2.1 catalyze the oxidation of 3-hydroxybutyraldehyde to 3-hydroxybutyrate (FIG. 2., Step I). Non-specific aldehyde dehydrogenase enzymes catalyze the oxidation of a broad range of substrates (EC 1.2.1.4). Non-specific NAD(P)H-dependent aldehyde dehydrogenases of *Saccharomyces cerevisiae* include ALD1(6)-5 (Navarro-Avino et al., *Yeast* 15:829-42 (1999); Quash et al., *Biochem Pharmacol* 64:1279-92 (2002)). Aldehyde dehydrogenase enzymes in *E. coli* include YdcW, BetB, FeaB and AldA (Gruez et al., *J. Mol. Biol.* 343:29-41 (2004); Yilmaz et al., *Biotechnol. Prog.* 18:1176-82 (2002); Rodriguez-Zavala et al., *Protein Sci.* 15:1387-96 (2006)). These and additional acid-forming aldehyde dehydrogenase enzymes are listed in the table below.

| Gene | GenBank Accession No | GI No. | Organism |
|---|---|---|---|
| ALD2 | NP_013893.1 | 6323822 | *Saccharomyces cerevisiae* s288c |
| ALD3 | NP_013892.1 | 6323821 | *Saccharomyces cerevisiae* s288c |
| ALD4 | NP_015019.1 | 6324950 | *Saccharomyces cerevisiae* s288c |
| ALD5 | NP_010996.2 | 330443526 | *Saccharomyces cerevisiae* s288c |
| ALD6 | NP_015264.1 | 6325196 | *Saccharomyces cerevisiae* s288c |
| ydcW | NP_415961.1 | 16129403 | *Escherichia coli* |
| betB | NP_414846.1 | 16128297 | *Escherichia coli* |
| feaB | AAC74467.2 | 87081896 | *Escherichia coli* |
| aldA | NP_415933.1 | 16129376 | *Escherichia coli* |
| sad | AAC74598.2 | 87081926 | *Escherichia coli* |
| gabD | AAC75708.1 | 1789015 | *Escherichia coli* |
| CaO19.8361 | XP_710976.1 | 68490403 | *Candida albicans* |
| CaO19.742 | XP_710989.1 | 68490378 | *Candida albicans* |
| YALI0C03025 | CAG81682.1 | 49647250 | *Yarrowia lipolytica* |
| ANI_1_1334164 | XP_001398871.1 | 145255133 | *Aspergillus niger* |
| ANI_1_2234074 | XP_001392964.2 | 317031176 | *Aspergillus niger* |
| ANI_1_226174 | XP_001402476.1 | 145256256 | *Aspergillus niger* |
| ALDH | P41751.1 | 1169291 | *Aspergillus niger* |
| KLLA0D09999 | CAH00602.1 | 49642640 | *Kluyveromyces lactis* |

The oxidation of 3-hydroxybutyraldehyde to 3-HB can also be catalyzed by an aldehyde oxidase with 3-hydroxybutyraldehde oxidase activity. Such enzymes can convert 3-HB-aldehyde, water and $O_2$ to 3-HB and hydrogen peroxide. Exemplary aldehyde oxidase enzymes can be found in *Bos taurus* and *Mus musculus* (Garattini et al., *Cell Mol. Life Sci.* 65:1019-48 (2008); Cabre et al., *Biochem. Soc. Trans.* 15:882-3 (1987)). Additional aldehyde oxidase gene candidates include the two flavin- and molybdenum-containing aldehyde oxidases of *Zea mays*, encoded by zmAO-1 and zmAO-2 (Sekimoto et al., *J. Biol. Chem.* 272:15280-85 (1997)).

| Gene | GenBank Accession No. | GI No. | Organism |
|---|---|---|---|
| zmAO-1 | NP_001105308.1 | 162458742 | *Zea mays* |
| zmAO-2 | BAA23227.1 | 2589164 | *Zea mays* |
| Aox1 | O54754.2 | 20978408 | *Mus musculus* |
| XDH | DAA24801.1 | 296482686 | *Bos taurus* |

1.2.1.b Acyl-CoA Reductase

The reduction of hydroxybutyryl-CoA to hydroxybutyraldehyde is catalyzed by an acylating aldehyde dehydrogenase or acyl-CoA reductase. Several acyl-CoA reductase enzymes are capable of reducing an acyl-CoA to its corresponding aldehyde (FIG. 2, Step C). Exemplary genes that encode such enzymes include the *Acinetobacter calcoaceticus* acr1 encoding a fatty acyl-CoA reductase (Reiser and Somerville, *J. Bacteriol.* 179:2969-2975 (1997), the *Acinetobacter* sp. M-1 fatty acyl-CoA reductase (Ishige et al., *Appl. Environ. Microbiol.* 68:1192-1195 (2002), and a CoA- and NADP-dependent succinate semialdehyde dehydrogenase encoded by the sucD gene in *Clostridium kluyveri* (Sohling and Gottschalk, *J. Bacteriol.* 178:871-880 (1996); Sohling and Gottschalk, *J. Bacteriol.* 1778:871-880 (1996)). SucD of *P. gingivalis* is another succinate semialdehyde dehydrogenase (Takahashi et al., *J. Bacteriol.* 182:4704-4710 (2000). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:45-55 (1972); Koo et al., *Biotechnol. Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.* 71:58-68 (2007)). Additional aldehyde dehydrogenase enzyme candidates are found in *Desulfatibacillum alkenivorans*, *Citrobacter koseri*, *Salmonella enterica*, *Lactobacillus brevis* and *Bacillus selenitireducens*.

| Protein | GenBank ID | GI number | Organism |
|---|---|---|---|
| acr1 | YP_047869.1 | 50086355 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |

| Protein | GenBank ID | GI number | Organism |
|---|---|---|---|
| adhE | AAV66076.1 | 55818563 | Leuconostoc mesenteroides |
| Bld | AAP42563.1 | 31075383 | Clostridium saccharoperbutylacetonicum |
| Ald | ACL06658.1 | 218764192 | Desulfatibacillum alkenivorans AK-01 |
| Ald | YP_001452373 | 157145054 | Citrobacter koseri ATCC BAA-895 |
| pduP | NP_460996.1 | 16765381 | Salmonella enterica Typhimurium |
| pduP | ABJ64680.1 | 116099531 | Lactobacillus brevis ATCC 367 |
| BselDRAFT_1651 | ZP_02169447 | 163762382 | Bacillus selenitireducens MLS10 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., Science 318:1782-1786 (2007); Thauer, Science 318:1732-1733 (2007)). The enzyme utilizes NADPH as a cofactor and has been characterized in Metallosphaera and Sulfolobus spp (Alber et al., J. Bacteriol. 188:8551-8559 (2006); Hugler et al., J. Bacteriol. 184:2404-2410 (2002)). The enzyme is encoded by Msed_0709 in Metallosphaera sedula (Alber et al., supra (2006); Berg et al., supra). A gene encoding a malonyl-CoA reductase from Sulfolobus tokodaii was cloned and heterologously expressed in E. coli (Alber et al., J. Bacteriol. 188:8551-8559 (2006)). This enzyme has also been shown to catalyze the conversion of methylmalonyl-CoA to its corresponding aldehyde (International Publication No. WO 2007/141208 (published Dec. 13, 2007)). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius and have been listed below. Yet another candidate for CoA-acylating aldehyde dehydrogenase is the ald gene from Clostridium beijerinckii (Toth et al., Appl. Environ. Microbiol. 65:4973-4980 (1999). This enzyme has been reported to reduce acetyl-CoA and butyryl-CoA to their corresponding aldehydes. This gene is very similar to eutE that encodes acetaldehyde dehydrogenase of Salmonella typhimurium and E. coli (Toth et al., supra).

| Protein | GenBank ID | GI number | Organism |
|---|---|---|---|
| Msed_0709 | YP_001190808.1 | 146303492 | Metallosphaera sedula |
| Mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 9473535 | Clostridium beijerinckii |
| eutE | AAA80209 | 687645 | Salmonella typhimurium |
| eutE | P77445 | 2498347 | Escherichia coli |

Exemplary two-step oxidoreductases that convert an acyl-CoA to alcohol (e.g., steps C and D of FIG. 2) include those that transform substrates such as acetyl-CoA to ethanol (e.g., adhE from E. coli (Kessler et al., FEBS Lett. 281:59-63 (1991)) and butyryl-CoA to butanol (e.g. adhE2 from C. acetobutylicum (Fontaine et al., J. Bacteriol. 184:821-830 (2002)). In addition to reducing acetyl-CoA to ethanol, the enzyme encoded by adhE in Leuconostoc mesenteroides has been shown to oxidize the branched chain compound isobutyraldehyde to isobutyryl-CoA (Kazahaya et al., J. Gen. Appl. Microbiol. 18:43-55 (1972); Koo et al., Biotechnol. Lett. 27:505-510 (2005)).

| Protein | GenBank ID | GI number | Organism |
|---|---|---|---|
| adhE | NP_415757.1 | 16129202 | Escherichia coli |
| adhE2 | AAK09379.1 | 12958626 | Clostridium acetobutylicum |
| adhE | AAV66076.1 | 55818563 | Leuconostoc mesenteroides |

Another exemplary bifunctional aldehyde/alcohol dehydrogenase enzyme can convert malonyl-CoA to 3-HP. An NADPH-dependent enzyme with this activity has characterized in Chloroflexus aurantiacus where it participates in the 3-hydroxypropionate cycle (Hugler et al., J. Bacteriol. 184:2404-2410 (2002); Strauss and Fuchs, Eur. J. Biochem. 215:633-643 (1993). This enzyme, with a mass of 300 kDa, is highly substrate-specific and shows little sequence similarity to other known oxidoreductases (Hugler, supra (2002)). No enzymes in other organisms have been shown to catalyze this specific reaction; however there is bioinformatic evidence that other organisms can have similar pathways (Klatt et al., Environ. Microbiol. 9:2067-2078 (2007)). Enzyme candidates in other organisms including Roseiflexus castenholzii, Erythrobacter sp. NAP1 and marine gamma proteobacterium HTCC2080 can be inferred by sequence similarity. Longer chain acyl-CoA molecules can be reduced by enzymes such as the jojoba (Simmondsia chinensis) FAR which encodes an alcohol-forming fatty acyl-CoA reductase. Its overexpression in E. coli resulted in FAR activity and the accumulation of fatty alcohol (Metz et al., Plant Physiol. 122:635-644 (2000)).

| Protein | GenBank ID | GI number | Organism |
|---|---|---|---|
| Rcas_2929 | YP_001433009.1 | 156742880 | Roseiflexus castenholzii |
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |
| FAR | AAD38039.1 | 5020215 | Simmondsia chinensis |

1.2.1.e CAR

The conversion of (3R)-hydroxybutyrate to (3R)-hydroxybutyraldehyde can be carried out by a (3R)-hydroxybutyrate reductase (Step 2I). A suitable enzyme for these transformations is the aryl-aldehyde dehydrogenase, or equivalently a carboxylic acid reductase, from *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)). This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industries*, ed. R. N. Patel, Chapter 15, pp. 425-440, CRC Press LLC, Boca Raton, Fla. (2006)). Information related to these proteins and genes is shown below. Additional car and npt genes can be identified based on sequence homology.

60(6):380-387 (2007)). Co-expression of griC and griD with SGR_665, an enzyme similar in sequence to the *Nocardia iowensis* npt, can be beneficial. Information related to these proteins and genes is shown below.

| Protein | GenBank ID    | GI number | Organism |
|---------|---------------|-----------|----------|
| griC    | YP_001825755.1 | 182438036 | *Streptomyces griseus* subsp. *griseus* NBRC 13350 |
| griD    | YP_001825756.1 | 182438037 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then

| Protein | GenBank ID | GI number | Organism |
|---------|------------|-----------|----------|
| Car | AAR91681.1 | 40796035 | *Nocardia iowensis* (sp. NRRL 5646) |
| Npt | ABI83656.1 | 114848891 | *Nocardia iowensis* (sp. NRRL 5646) |
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr.*

*Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date. Information related to these proteins and genes is shown below.

| Protein | GenBank ID | GI number | Organism |
| --- | --- | --- | --- |
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

Any of these CAR or CAR-like enzymes can exhibit 3-hydroxybutyrate reductase activity or can be engineered to do so.

2.3.1.b Thiolase

Beta-ketothiolase enzymes in the EC class 2.3.1 catalyze the condensation of acetyl-CoA substrates to acetoacetyl-CoA (FIG. 2, Step A). Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000)), and ERG10 from *S. cerevisiae* (Hiser et al., *J. Biol. Chem.* 269:31383-31389 (1994)). The acetoacetyl-CoA thiolase from *Zoogloea ramigera* is irreversible in the biosynthetic direction and a crystal structure is available (Merilainen et al., *Biochem* 48: 11011-25 (2009)). *Ralstonia eutropha* also has a number of thiolase enzymes, shown in the table below.

| Protein | GenBank ID | GI Number | Organism |
| --- | --- | --- | --- |
| atoB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |
| phbA | P07097.4 | 135759 | *Zoogloea ramigera* |
| bktB | YP_002005382.1 | 194289475 | *Cupriavidus taiwanensis* |
| phaA | YP_725941.1 | 113867452 | *Ralstonia eutropha* |
| h16_A1713 | YP_726205.1 | 113867716 | *Ralstonia eutropha* |
| pcaF | YP_728366.1 | 116694155 | *Ralstonia eutropha* |
| h16_B1369 | YP_840888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |

2.3.1.e Synthase

Acetoacetyl-CoA is synthesized from acetyl-CoA and malonyl-CoA by acetoacetyl-CoA synthase (EC 2.3.1.194) (FIG. 2, Step F). This enzyme (FhsA) has been characterized in the soil bacterium *Streptomyces* sp. CL 190 where it participates in mevalonate biosynthesis (Okamura et al., *PNAS USA* 107:11265-70 (2010)). As this enzyme catalyzes an essentially irreversible reaction, it is particularly useful for metabolic engineering applications for overproducing metabolites, fuels or chemicals derived from acetoacetyl-CoA. For example, the enzyme has been heterologously expressed in organisms that biosynthesize butanol (Lan et al., *PNAS USA* (2012)) and poly-(3-hydroxybutyrate) (Matsumoto et al., *Biosci Biotech Biochem*, 75:364-366 (2011). Other relevant products of interest include 1,4-butanediol and isopropanol. Other acetoacetyl-CoA synthase genes can be identified by sequence homology to fhsA.

| Protein | GenBank ID | GI Number | Organism |
| --- | --- | --- | --- |
| fhsA | BAJ83474.1 | 325302227 | *Streptomyces* sp CL190 |
| AB183750.1: 11991 . . . 12971 | BAD86806.1 | 57753876 | *Streptomyces* sp. KO-3988 |
| epzT | ADQ43379.1 | 312190954 | *Streptomyces cinnamonensis* |
| ppzT | CAX48662.1 | 238623523 | *Streptomyces anulatus* |
| O3I_22085 | ZP_09840373.1 | 378817444 | *Nocardia brasiliensis* |

2.8.3.a, 3.1.2.a, 6.2.1.a CoA Transferase, Hydrolase, Synthetase

Acetoacetyl-CoA:acetyl-CoA transferase (FIG. 2, step G) naturally converts acetoacetyl-CoA and acetate to acetoacetate and acetyl-CoA. This enzyme can also accept 3-hydroxybutyryl-CoA as a substrate or could be engineered to do so (FIG. 2, step H,). Exemplary enzymes include the gene products of atoAD from *E. coli* (Hanai et al., *Appl Environ Microbiol* 73:7814-7818 (2007)), ctfAB from *C. acetobutylicum* (Jojima et al., *Appl Microbiol Biotechnol* 77:1219-1224 (2008)), and ctfAB from *Clostridium saccharoperbutylacetonicum* (Kosaka et al., *Biosci. Biotechnol Biochem.* 71:58-68 (2007)). Information related to these proteins and genes is shown below.

| Protein | GenBank ID | GI number | Organism |
| --- | --- | --- | --- |
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3-ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics* 68:144-151 (2000); Tanaka et al., *Mol. Hum. Reprod.* 8:16-23 (2002)). Information related to these proteins and genes is shown below.

| Protein | GenBank ID | GI number | Organism |
| --- | --- | --- | --- |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |

| Protein | GenBank ID | GI number | Organism |
| --- | --- | --- | --- |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Additional suitable acetoacetyl-CoA and 3-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA acetyltransferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA:acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyromonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below.

| Protein | GenBank ID | GI number | Organism |
| --- | --- | --- | --- |
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Acetoacetyl-CoA can be hydrolyzed to acetoacetate by acetoacetyl-CoA hydrolase (FIG. 2, Step G). Similarly, 3-hydroxybutyryl-CoA can be hydrolyzed to 3-hydroxybutyate by 3-hydroxybutyryl-CoA hydrolase (FIG. 2, Step H). Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, *J. Biol. Chem.* 258(8):4725-4733 (1983)). Additionally, an enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., *Eur. J. Biochem.* 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, *Plant. Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding succinyl-CoA:3-ketoacid-CoA transferases and acetoacetyl-CoA:acetyl-CoA transferases can also be used as hydrolases with certain mutations to change their function. The acetyl-CoA hydrolase, ACH1, from *S. cerevisiae* represents another candidate hydrolase (Buu et al., *J. Biol. Chem.* 278:17203-17209 (2003)). Information related to these proteins and genes is shown below.

| Protein | GenBank ID | GI number | Organism |
| --- | --- | --- | --- |
| Acot12 | NP_570103.1 | 18543355 | *Rattus norvegicus* |
| GctA | CAA57199 | 559392 | *Acidaminococcus fermentans* |
| GctB | CAA57200 | 559393 | *Acidaminococcus fermentans* |
| ACH1 | NP_009538 | 6319456 | *Saccharomyces cerevisiae* |

Another CoA hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)) and the closest *E. coli* homolog, tesB, which can also hydrolyze a broad range of CoA thioesters (Naggert et al., *J. Biol. Chem.* 266:11044-11050 (1991)) including 3-hydroxybutyryl-CoA (Tseng et al., *Appl. Environ. Microbiol.* 75(10):3137-3145 (2009)). A similar enzyme has also been characterized in the rat liver (Deana, *Biochem. Int.* 26:767-773 (1992)). Other potential *E. coli* thioester hydrolases include the gene products of tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). Information related to these proteins and genes is shown below.

| Protein | GenBank ID | GI number | Organism |
|---|---|---|---|
| Acot8 | CAA15502 | 3191970 | *Homo sapiens* |
| TesB | NP_414986 | 16128437 | *Escherichia coli* |
| Acot8 | NP_570112 | 51036669 | *Rattus norvegicus* |
| TesA | NP_415027 | 16128478 | *Escherichia coli* |
| YbgC | NP_415264 | 16128711 | *Escherichia coli* |
| PaaI | NP_415914 | 16129357 | *Escherichia coli* |
| YbdB | NP_415129 | 16128580 | *Escherichia coli* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J. Biol. Chem.* 269:14248-14253 (1994)). Genes encoding this enzyme include hibch of *Rattus norvegicus* (Shimomura et al., supra (1994); Shimomura et al., *Methods Enzymol.* 324:229-240 (2000)) and *Homo sapiens* (Shimomura et al., supra (1994). Candidate genes by sequence homology include hibch of *Saccharomyces cerevisiae* and BC_2292 of *Bacillus cereus*. BC_2292 was shown to demonstrate 3-hydroxybutyryl-CoA hydrolase activity and function as part of a pathway for 3-hydroxybutyrate synthesis when engineered into *Escherichia coli* (Lee et al., *Appl. Microbiol. Biotechnol.* 79:633-641 (2008)). Information related to these proteins and genes is shown below.

| Protein | GenBank ID | GI number | Organism |
|---|---|---|---|
| Hibch | Q5XIE6.2 | 146324906 | *Rattus norvegicus* |
| Hibch | Q6NVY1.2 | 146324905 | *Homo sapiens* |
| Hibch | P28817.2 | 2506374 | *Saccharomyces cerevisiae* |
| BC_2292 | AP09256 | 29895975 | *Bacillus cereus* ATCC 14579 |

An alternative method for removing the CoA moiety from acetoacetyl-CoA or 3-hydroxybutyryl-CoA (FIG. 2, Steps G and H) is to apply a pair of enzymes such as a phosphate-transferring acyltransferase and a kinase to impart acetoacetyl-CoA or 3-hydroxybutyryl-CoA synthetase activity. This activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10):3137-3145 (2009)). Specifically, the ptb gene from *C. acetobutylicum* encodes an enzyme that can convert an acyl-CoA into an acyl-phosphate (Walter et al. *Gene* 134(1): 107-11 (1993)); Huang et al. *J Mol Microbiol Biotechnol* 2(1):33-38 (2000). Additional ptb genes can be found in butyrate-producing bacterium L2-50 (Louis et al. *J. Bacteriol.* 186:2099-2106 (2004)) and *Bacillus megaterium* (Vazquez et al. *Curr. Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Information related to these proteins and genes is shown below.

| Protein | GenBank ID | GI number | Organism |
|---|---|---|---|
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 (Walter et al. *Gene* 134(1):107-111 (1993); Huang et al. *J Mol Microbiol Biotechnol* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)). Information related to these proteins and genes is shown below.

| Protein | GenBank ID | GI number | Organism |
|---|---|---|---|
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

The hydrolysis of acetoacetyl-CoA or 3-hydroxybutyryl-CoA can alternatively be carried out by a single enzyme or enzyme complex that exhibits acetoacetyl-CoA or 3-hydroxybutyryl-CoA synthetase activity (FIG. 2, Steps G and H). This activity enables the net hydrolysis of the CoA-ester of either molecule, and in some cases, results in the simultaneous generation of ATP. For example, the product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (U.S. Pat. No. 5,958,745 (issued Sep. 28, 1999)). Information related to these proteins and genes is shown below.

| Protein | GenBank ID | GI number | Organism |
|---|---|---|---|
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178(14):4122-4130 (1996)).

Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318:1782-1786 (2007)). This function has been tentatively assigned to the Msed_1422 gene. Information related to these proteins and genes is shown below.

| Protein | GenBank ID | GI number | Organism |
| --- | --- | --- | --- |
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed_1422 | YP_001191504 | 146304188 | *Metallosphaera sedula* |

ADP-forming acetyl-CoA synthetase (ACD, EC 6.2.1.13) is another candidate enzyme that can couple the conversion of acyl-CoA esters to their corresponding acids with the concurrent synthesis of ATP (FIG. 2, Steps G and H). Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus, H. marismortui* and *P. aerophilum* have all been cloned, functionally expressed, and characterized in *E. coli* (Musfeldt et al., supra; Brasen et al., supra (2004)). Information related to these proteins and genes is shown below.

| Protein | GenBank ID | GI number | Organism |
| --- | --- | --- | --- |
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

5.1.2. Epimerase

The interconversion of (3R)-hydroxybutyryl-CoA and (3S)-hydroxyisobutyryl-CoA is catalyzed by 3-hydroxybutyryl-CoA epimerase (FIG. 2, Step K). Hydroxyacyl-CoA epimerases (EC 5.1.2.3) are suitable enzymes for catalyzing this transformation. Exemplary 3-hydroxyacyl-CoA epimerases are found in *E. coli* (fadB, fadJ) and *Cucumis sativus* (MFPa) (Snell et al., *J. Bacteriol.* 184:5696-705 (2002); Yang et al., *J. Biol. Chem.* 268:6588-92 (1993); Preisig-Muller et al., *J. Biol. Chem.* 269:20475-81 (1994)). Epimerization typically occurs via a dehydration/hydration mechanism that proceeds through a crotonyl-CoA intermediate. Distinct (3S)-hydroxybutyryl-CoA dehydratase and crotonase (R-forming) enzymes, or a single multifunctional epimerase enzyme, can catalyze this reaction.

| Protein | GenBank ID | GI number | Organism |
| --- | --- | --- | --- |
| fadJ | NP_416843.1 | 16130274 | *Escherichia coli* |
| fadB | NP_418288.1 | 16131692 | *Escherichia coli* |
| MFP-a | Q39659.1 | 34922495 | *Cucumis sativus* |

6.4.1.a Carboxylase

Acetyl-CoA carboxylase (EC 6.4.1.2) catalyzes the ATP-dependent carboxylation of acetyl-CoA to malonyl-CoA (FIG. 2, Step E). This enzyme is biotin dependent and is the first reaction of fatty acid biosynthesis initiation in several organisms. Exemplary enzymes are encoded by accABCD of *E. coli* (Davis et al., *J. Biol. Chem.* 275:28593-8 (2000)), ACC1 of *Saccharomyces cerevisiae* and homologs (Sumper et al., *Methods Enzym.* 71:34-7 (1981)). The mitochondrial acetyl-CoA carboxylase of *S. cerevisiae* is encoded by HFA1. Acetyl-CoA carboxylase holoenzyme formation requires attachment of biotin by a biotin:apoprotein ligase such as BPL1 of *S. cerevisiae*. These and additional ACC enzymes are listed in the table below.

| Protein | GenBank ID | GI Number | Organism |
| --- | --- | --- | --- |
| ACC1 | CAA96294.1 | 1302498 | *Saccharomyces cerevisiae* |
| KLLA0F06072g | XP_455355.1 | 50310667 | *Kluyveromyces lactis* |
| ACC1 | XP_718624.1 | 68474502 | *Candida albicans* |
| YALI0C11407p | XP_501721.1 | 50548503 | *Yarrowia lipolytica* |
| ANI_1_1724104 | XP_001395476.1 | 145246454 | *Aspergillus niger* |
| accA | AAC73296.1 | 1786382 | *Escherichia coli* |
| accB | AAC76287.1 | 1789653 | *Escherichia coli* |
| accC | AAC76288.1 | 1789654 | *Escherichia coli* |
| accD | AAC75376.1 | 1788655 | *Escherichia coli* |
| accA | CAD08690.1 | 16501513 | *Salmonella enterica* |
| accB | CAD07894.1 | 16504441 | *Salmonella enterica* |
| accC | CAD07895.1 | 16504442 | *Salmonella enterica* |
| accD | CAD07598.1 | 16503590 | *Salmonella enterica* |
| HFA1 | NP_013934.1 | 6323863 | *Saccharomyces cerevisiae* |
| BPL1 | NP_010140.1 | 6320060 | *Saccharomyces cerevisiae* |

Example III

Formation of Acetoacetyl-ACP and Other (3R)-Hydroxybutyl (3R)-hydroxybutyrate Precursors via Malonyl-ACP (3R)-Hydroxybutyl (3R)-hydroxybutyrate precursors acetoacetyl-CoA, (3R)-hydroxybutyryl-CoA, (3R)-hydroxybutyrate, (3R)-hydroxybutyraldehyde and (R)-1,3-butanediol can be formed from acyl-ACP intermediates as shown in FIG. 3. These pathways begin with the initiation of fatty acid biosynthesis in which malonyl-ACP is condensed with acetyl-CoA or acetyl-ACP to form acetoacetyl-ACP (step A). Acetoacetyl-ACP is converted to acetoacetyl-CoA (step C) or reduced to (3R)-hydroxybutyryl-ACP (step B). The (3R)-hydroxybutyryl-ACP intermediate can be further converted to its corresponding acyl-CoA, acid, aldehyde or alcohol. Enzymes for each step of FIG. 3 are described below.

Enzyme activities required for the reactions shown in FIG. 3 are listed in the table below.

| Label | Function | Step |
|---|---|---|
| 1.1.1.a | Oxidoreductase (oxo to alcohol) | 3B |
| 1.2.1.f | Oxidoreductase (acyl-ACP to aldehyde) | 3F |
|  | Oxidoreductase (acyl-ACP to alcohol) | 3E |
| 2.3.1.e | Acyl-ACP C-acyltransferase (decarboxylating) | 3A |
| 2.3.1.f | CoA-ACP acyltransferase | 3C, 3D |
| 2.3.1.g | Fatty-acid synthase | 3A, 7B |
| 3.1.2.b | Acyl-ACP thioesterase | 3G |

1.1.1.a Oxidoreductase (Oxo to Alcohol)

The reduction of acetoacetyl-ACP to (3R)-hydroxyacetyl-ACP is catalyzed by acetoacetyl-ACP reductase or 3-oxoacyl-ACP reductase (EC 1.1.1.100). The *E. coli* 3-oxoacyl-ACP reductase is encoded by fabG (Zhang et al., *J. Biol. Chem.* 278:52935-43 (2003)). Additional enzymes with this activity have been characterized in *Bacillus anthracis* (Zaccai et al., *Prot. Struct. Funct. Gen.* 70:562-7 (2008)) and *Mycobacterium tuberculosis* (Gurvitz, *Mol. Genet. Genomics* 282:407-16 (2009)). The beta-ketoacyl reductase (KR) domain of eukaryotic fatty acid synthase also catalyzes this activity (Smith, *FASEB J*, 8:1248-59 (1994)).

| Protein | GenBank ID | GI Number | Organism |
|---|---|---|---|
| fabG | P0AEK2.1 | 84028081 | *Escherichia coli* |
| fabG | AAP27717.1 | 30258498 | *Bacillus anthracis* |
| FabG1 | NP_215999.1 | 15608621 | *Mycobacterium tuberculosis* |
| FabG4 | YP_003030167.1 | 253797166 | *Mycobacterium tuberculosis* |

1.2.1.f Oxidoreductase (Acyl-ACP to Aldehyde)

The reduction of an acyl-ACP to its corresponding aldehyde is catalyzed by an acyl-ACP reductase (AAR). Such a transformation is depicted in step F of FIG. 3. Suitable enzyme candidates include the orf1594 gene product of *Synechococcus elongatus* PCC7942 and homologs thereof (Schirmer et al., *Science*, 329: 559-62 (2010)). The *S. elongates* PCC7942 acyl-ACP reductase is coexpressed with an aldehyde decarbonylase in an operon that appears to be conserved in a majority of cyanobacterial organisms. This enzyme, expressed in *E. coli* together with the aldehyde decarbonylase, conferred the ability to produce alkanes. The *P. marinus* AAR was also cloned and functionally expressed in *E. coli* (U.S. Publication No. 2011/0207203 (published Aug. 25, 2011).

| Protein | GenBank ID | GI Number | Organism |
|---|---|---|---|
| orf1594 | YP_400611.1 | 81300403 | *Synechococcus elongatus* PCC7942 |
| PMT9312_0533 | YP_397030.1 | 78778918 | *Prochlorococcus marinus* MIT 9312 |
| syc0051_d | YP_170761.1 | 56750060 | *Synechococcus elongatus* PCC 6301 |
| Ava_2534 | YP_323044.1 | 75908748 | *Anabaena variabilis* ATCC 29413 |
| alr5284 | NP_489324.1 | 17232776 | *Nostoc* sp. PCC 7120 |
| Aazo_3370 | YP_003722151.1 | 298491974 | *Nostoc azollae* |
| Cyan7425_0399 | YP_002481152.1 | 220905841 | *Cyanothece* sp. PCC 7425 |
| N9414_21225 | ZP_01628095.1 | 119508943 | *Nodularia spumigena* CCY9414 |
| L8106_07064 | ZP_01619574.1 | 119485189 | *Lyngbya* sp. PCC 8106 |

1.2.1.g Oxidoreductase (Acyl-ACP to Alcohol)

The reduction of an acyl-ACP to its corresponding alcohol is catalyzed by an acyl-ACP reductase (alcohol forming). Such a transformation is depicted in step E of FIG. 3. Fatty acyl reductase enzymes that use acyl-ACP substrates to produce alcohols are known in the art. Alcohol forming acyl-ACP reductases include Maqu_2220 of *Marinobacter aquaeolei* VT8 and Hch_05075 of *Hahella chejuensis* KCTC2396 (see International Publication No. WO 2013/048557 (published Apr. 4, 2013)). These enzymes convert both acyl-ACP substrates and acyl-CoA substrates to their corresponding alcohols. The *M. aquaeolei* AAR was previously characterized as an aldehyde reductase (Wahlen et al., *AEM* 75:2758-2764 (2009)) and U.S. Publication No. 2010/0203614 (published Aug. 12, 2010)). Alcohol forming acyl-ACP reductase enzymes are shown in the table below.

| Protein | GenBank ID | GI Number | Organism |
|---|---|---|---|
| Maqu_2220 | ABM19299 | 120324984 | *Marinobacter aquaeolei* |
| Hch_05075 | YP_436183 | 83647748 | *Hahella chejuensis* |
| MDG893_11561 | ZP_01892457.1 | 149374683 | *Marinobacter algicola* DG893 |
| HP15_810 | ADP96574.1 | 311693701 | *Marinobacter adhaerens* HP15 |
| RED65_09894 | ZP_01305629.1 | 94499091 | *Oceanobacter* sp. RED65 |

2.3.1.e Acyl-ACP C-Acyltransferase (Decarboxylating)

In step A of FIG. 3, acetoacetyl-ACP is formed from malonyl-ACP and either acetyl-CoA or acetyl-ACP. Both reactions are catalyzed by acyl-ACP C-acyltransferase enzymes in EC class 2.3.1. The condensation of malonyl-ACP and acetyl-CoA is catalyzed by beta-ketoacyl-ACP synthase (KAS, EC 2.3.1.180). *E. coli* has three KAS enzymes encoded by fabB, fabF andfabH. FabH (KAS III), the key enzyme of initiation of fatty acid biosynthesis in *E. coli*, is selective for the formation of acetoacetyl-ACP. FabB and FabF catalyze the condensation of malonyl-ACP with a range of acyl-ACP substrates and function primarily in fatty acid elongation although they can also react with acetyl-ACP and thereby participate in fatty acid initittation. For example, the *Bacillus subtilis* KAS enzymes are similar to FabH but are less selective, accepting branched acyl-CoA substrates (Choi et al., *J Bacteriol* 182:365-70 (2000)).

| Protein | GenBank ID | GI Number | Organism |
| --- | --- | --- | --- |
| fabB | AAC75383.1 | 1788663 | *Escherichia coli* |
| fabF | AAC74179.1 | 1787337 | *Escherichia coli* |
| fabH | AAC74175.1 | 1787333 | *Escherichia coli* |
| FabHA | NP_389015.1 | 16078198 | *Bacillus subtilis* |
| FabHB | NP_388898.1 | 16078081 | *Bacillus subtilis* |

Alternately, acetyl-CoA can first be activated to acetyl-ACP and subsequently condensed to acetoacetyl-ACP by two enzymes, acetyl-CoA:ACP transacylase (EC 2.3.1.38) and acetoacetyl-ACP synthase (EC 2.3.1.41). Acetyl-CoA:ACP transacylase converts acetyl-CoA and an acyl carrier protein to acetyl-ACP, releasing CoA. Enzyme candidates for acetyl-CoA:ACP transacylase are described in section EC 2.3.1.f below. Acetoacetyl-ACP synthase enzymes catalyze the condensation of acetyl-ACP and malonyl-ACP. This activity is catalyzed by FabF and FabB of *E. coli*, as well as the multifunctional eukaryotic fatty acid synthase enzyme complexes described below in EC 2.3.1.g.

2.3.1.f CoA-ACP Acyltransferase

The exchange of an ACP moiety for a CoA is catalyzed by enzymes in EC class 2.3.1. This reaction is shown in steps C and D of FIG. 3. Activation of acetyl-CoA to acetyl-ACP is also catalyzed by a CoA:ACP acyltransferase (step A). Enzymes with CoA-ACP acyltransferase activity include acetyl-CoA:ACP transacylase (EC 2.3.1.38) and malonyl-CoA:ACP transacylase (EC 2.3.1.39).

The FabH (KASIII) enzyme of *E. coli* functions as an acyl-CoA:ACP transacylase, in addition to its primary activity of forming acetoacetyl-ACP. Butyryl-ACP is accepted as an alternate substrate of FabH (Prescott et al., *Adv. Enzymol. Relat. Areas Mol*, 36:269-311 (1972)). Acetyl-CoA:ACP transacylase enzymes from *Plasmodium falciparum* and *Streptomyces avermitillis* have been heterologously expressed in *E. coli* (Lobo et al., *Biochem* 40:11955-64 (2001)). A synthetic KASIII (FabH) from *P. falciparum* expressed in a fabH-deficient *Lactococcus lactis* host was able to complement the native fadH activity (Du et al., *AEM* 76:3959-66 (2010)). The acetyl-CoA:ACP transacylase enzyme from *Spinacia oleracea* accepts other acyl-ACP molecules as substrates, including butyryl-ACP (Shimakata et al., *Methods Enzym* 122:53-9 (1986)). The sequence of this enzyme has not been determined to date. Malonyl-CoA:ACP transacylase enzymes include FabD of *E. coli* and *Brassica napsus* (Verwoert et al., *J Bacteriol*, 174:2851-7 (1992); Simon et al., *FEBS Lett* 435:204-6 (1998)). FabD of *B. napsus* was able to complement fabD-deficient *E. coli*. The multifunctional eukaryotic fatty acid synthase enzyme complexes (described in EC 2.3.1.g) also catalyze this activity.

| Protein | GenBank ID | GI Number | Organism |
| --- | --- | --- | --- |
| fabH | AAC74175.1 | 1787333 | *Escherichia coli* |
| fadA | NP_824032.1 | 29829398 | *Streptomyces avermitillis* |
| fabH | AAC63960.1 | 3746429 | *Plasmodium falciparum* |
| Synthetic construct | ACX34097.1 | 260178848 | *Plasmodium falciparum* |
| fabH | CAL98359.1 | 124493385 | *Lactococcus lactis* |
| fabD | AAC74176.1 | 1787334 | *Escherichia coli* |
| fabD | CAB45522.1 | 5139348 | *Brassica napsus* |

2.3.1.g Fatty Acid Synthase

Steps A and B of FIG. 3 can together be catalyzed fatty acid synthase or fatty-acyl-CoA synthase, multifunctional enzyme complexes composed of multiple copies of one or more subunits. The fatty acid synthase of *Saccharomyces cerevisiae* is a dodecamer composed of two multifunctional subunits FAS1 and FAS2 that together catalyze all the reactions required for fatty acid synthesis: activation, priming, elongation and termination (Lomakin et al., *Cell* 129:319-32 (2007)). This enzyme complex catalyzes the formation of long chain fatty acids from acetyl-CoA and malonyl-CoA. The favored product of eukaryotic FAS systems is palmitic acid (C16). Similar fatty acid synthase complexes are found in *Candida parapsilosis* and *Thermomyces lanuginosus* (Nguyen et al., *PLoS One* 22:e8421 (2009); Jenni et al., *Science* 316:254-61 (2007)). The multifunctional Fas enzymes of *Mycobacterium tuberculosis* and mammals such as *Homo sapiens* are also suitable candidates (Fernandes and Kolattukudy, *Gene* 170:95-99 (1996) and Smith et al., *Prog Lipid Res* 42:289-317 (2003)).

| Protein | GenBank ID | GI Number | Organism |
| --- | --- | --- | --- |
| FAS1 | CAA82025.1 | 486321 | *Saccharomyces cerevisiae* |
| FAS2 | CAA97948.1 | 1370478 | *Saccharomyces cerevisiae* |
| Fas1 | ABO37973.1 | 133751597 | *Thermomyces lanuginosus* |
| Fas2 | ABO37974.1 | 133751599 | *Thermomyces lanuginosus* |
| Fas | AAB03809.1 | 1036835 | *Mycobacterium tuberculosis* |
| Fas | NP_004095.4 | 41872631 | *Homo sapiens* |

3.1.2.b Acyl-ACP Thioesterase

Acyl-ACP thioesterase enzymes convert an acyl-ACP to its corresponding acid. Such a transformation is required in step G of FIG. 3. Exemplary enzymes include the FatA and FatB isoforms of *Arabidopsis thaliana* (Salas et al., Arch Biochem Biophys 403:25-34 (2002)). The activities of these two proteins vary with carbon chain length, with FatA preferring oleyl-ACP and FatB preferring palmitoyl-ACP. See 3.1.2.14. A number of thioesterases with different chain length specificities are listed in WO 2008/113041 and are included in the table below [see p 126 Table 2A of patent]. For example, it has been shown previously that expression of medium chain plant thioesterases like FatB from *Umbellularia californica* in *E. coli* results in accumulation of high levels of medium chain fatty acids, primarily laurate (C12:0). Similarly, expression of *Cuphea palustris* FatB1 thioesterase in *E. coli* led to accumulation of C8-10:0 acyl-ACPs (Dehesh et al., *Plant Physiol* 110:203-10 (1996)). Similarly, *Carthamus tinctorius* thioesterase, when expressed in *E. coli* leads to >50 fold elevation in C 18:1 chain termination and release as free fatty acid (Knutzon et al., *Plant Physiol* 100:1751-58 (1992)). Methods for altering the substrate specificity of acyl-ACP thioesterases are also known in the art (for example, European Patent Application EP1605048 (published Dec. 14, 2005)).

| Protein | GenBank ID | GI Number | Organism |
| --- | --- | --- | --- |
| fatA | AEE76980.1 | 332643459 | *Arabidopsis thaliana* |
| fatB | AEE28300.1 | 332190179 | *Arabidopsis thaliana* |
| fatB2 | AAC49269.1 | 1292906 | *Cuphea hookeriana* |
| fatB1 | AAC49179.1 | 1215718 | *Cuphea palustris* |
| M96568.1: | AAA33019.1 | 404026 | *Carthamus tinctorius* |

| Protein | GenBank ID | GI Number | Organism |
|---|---|---|---|
| 94 . . . 1251 | | | |
| fatB1 | Q41635.1 | 8469218 | *Umbellularia californica* |
| tesA | AAC73596.1 | 1786702 | *Escherichia coli* |

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, said microbial organism having a (3R)-hydroxybutyl (3R)-hydroxybutyrate pathway,
    wherein said (3R)-hydroxybutyl (3R)-hydroxybutyrate pathway comprises one or more (3R)-hydroxybutyl (3R)-hydroxybutyrate pathway enzymes selected from:
    (1) 1A;
    (2) 1B;
    (3) 1C and 1E;
    (4) 1D and 1E;
    (5) 1F; and
    (6) 1G and 1E,
    wherein 1A is a (3R)-hydroxybutyl (3R)-hydroxybutyrate ester forming enzyme, wherein 1B is a (3R)-hydroxybutyryl-CoA:(R)-1,3-butanediol alcohol transferase, wherein 1C is a (3R)-hydroxybutyl 3-oxobutyrate ester forming enzyme, wherein 1D is an acetoacetyl-CoA:(R)-1,3-butanediol alcohol transferase, wherein 1E is a (3R)-hydroxybutyl 3-oxobutyrate reductase, wherein 1F is a (3R)-hydroxybutyryl-ACP:(R)-1,3-butanediol ester synthase, wherein 1G is an acetoacetyl-ACP:(R)-1,3-butanediol ester synthase,
    wherein the (3R)-hydroxybutyl (3R)-hydroxybutyrate pathway enzyme is encoded by at least one exogenous nucleic acid and is expressed in a sufficient amount to produce (3R)-hydroxybutyl (3R)-hydroxybutyrate.

2. The non-naturally occurring microbial organism of claim 1, wherein said microbial organism comprises exogenous nucleic acids encoding each of the enzymes of at least one of the pathways selected from (1)-(6).

3. The non-naturally occurring microbial organism of claim 1, wherein said at least one exogenous nucleic acid is a heterologous nucleic acid.

4. The non-naturally occurring microbial organism of claim 1, wherein said microbial organism is a species of bacteria, yeast, or fungus.

5. A method for producing (3R)-hydroxybutyl (3R)-hydroxybutyrate, comprising culturing the non-naturally occurring microbial organism of claim 1 under conditions and for a sufficient period of time to produce (3R)-hydroxybutyl (3R)-hydroxybutyrate.

6. A non-naturally occurring microbial organism, said microbial organism having a (3R)-hydroxybutyl (3R)-hydroxybutyrate pathway,
    wherein said (3R)-hydroxybutyl (3R)-hydroxybutyrate pathway comprises one or more (3R)-hydroxybutyl (3R)-hydroxybutyrate pathway enzymes selected from:
    (1) 1A;
    (2) 1B;
    (3) 1C and 1E;
    (4) 1D and 1E;
    (5) 1F; and
    (6) 1G and 1E,
    wherein 1A is a (3R)-hydroxybutyl (3R)-hydroxybutyrate ester forming enzyme, wherein 1B is a (3R)-hydroxybutyryl-CoA:(R)-1,3-butanediol alcohol transferase, wherein 1C is a (3R)-hydroxybutyl 3-oxobutyrate ester forming enzyme, wherein 1D is an acetoacetyl-CoA:(R)-1,3-butanediol alcohol transferase, wherein 1E is a (3R)-hydroxybutyl 3-oxobutyrate reductase, wherein 1F is a (3R)-hydroxybutyryl-ACP:(R)-1,3-butanediol ester synthase, wherein 1G is an acetoacetyl-ACP:(R)-1,3-butanediol ester synthase,
    wherein the (3R)-hydroxybutyl (3R)-hydroxybutyrate pathway enzyme is encoded by at least one exogenous nucleic acid.

* * * * *